United States Patent
Taniguchi et al.

(10) Patent No.: US 10,813,950 B2
(45) Date of Patent: Oct. 27, 2020

(54) IMMUNOTHERAPY USING ALLO-NKT CELLS, CELLS FOR IMMUNOTHERAPY IN WHICH ALPHA CHAIN OF T-CELL RECEPTOR (TCR) GENE HAS BEEN REARRANGED TO UNIFORM Vα-Jα, AND BANKING OF NKT CELLS DERIVED FROM SAID CELLS

(75) Inventors: Masaru Taniguchi, Yokohama (JP); Haruhiko Koseki, Yokohama (JP); Hiroshi Watarai, Yokohama (JP); Shin-ichiro Fujii, Yokohama (JP)

(73) Assignee: RIKEN, Wako (JP)

(*) Notice: Subject to any disclaimer, the term of this patent is extended or adjusted under 35 U.S.C. 154(b) by 1087 days.

(21) Appl. No.: 13/991,059

(22) PCT Filed: Dec. 2, 2011

(86) PCT No.: PCT/JP2011/077990
§ 371 (c)(1),
(2), (4) Date: Jul. 29, 2013

(87) PCT Pub. No.: WO2012/074116
PCT Pub. Date: Jun. 7, 2012

(65) Prior Publication Data
US 2013/0295142 A1 Nov. 7, 2013

Related U.S. Application Data

(60) Provisional application No. 61/419,064, filed on Dec. 2, 2010.

(51) Int. Cl.
| | |
|---|---|
| A61K 35/17 | (2015.01) |
| C12N 5/0783 | (2010.01) |
| C07K 14/725 | (2006.01) |
| A61K 45/06 | (2006.01) |
| A61K 31/7028 | (2006.01) |
| C12N 15/85 | (2006.01) |

(52) U.S. Cl.
CPC .......... *A61K 35/17* (2013.01); *A61K 31/7028* (2013.01); *A61K 45/06* (2013.01); *C07K 14/7051* (2013.01); *C12N 5/0646* (2013.01); *C12N 15/85* (2013.01)

(58) Field of Classification Search
None
See application file for complete search history.

(56) References Cited

U.S. PATENT DOCUMENTS

| 9,101,558 B2 | 8/2015 | Taniguchi et al. |
| 2011/0020932 A1 | 1/2011 | Wakao et al. |
| 2011/0236362 A1 | 9/2011 | Watarai et al. |

FOREIGN PATENT DOCUMENTS

| WO | WO 2008/038579 A1 | 4/2008 |
| WO | WO 2009/041573 A1 | 4/2009 |
| WO | WO 2010/027094 A1 | 3/2010 |

OTHER PUBLICATIONS

Akbari et al (Nature Med. 2003, 9(5): 582-588).*
Diana and Lehuen (Eur. J. Immunol. 2009, 39: 3283-3291).*
Terabe and Berzofsky (Adv. Canc. Res. 2008, 101: 277-348).*
Subleski et al (Immunother., 2011, 3(10): 1167-1184).*
Tedeschi and Asero (Expert Rev. Clin. Immunol., 2008, 4(6)) 767-776, abstract).*
Schrieber et al (Seminar. Immunol. 22: 105-112, 2010).*
Klebanoff et al (Immunol. Rev. 2011, 239: 27-44).*
Berger et al (Int. J. Cancer. 111: 229-237, 2004).*
Oregja-Guervara et al (BMC Neurology, 2012, 12:95, pp. 1-6).*
Illiopoulou et al (Canc. Innumol. Immunother. 2010, 59: 1781-1789) (Year: 2010).*
Watari et al (Blood, Jan. 2010, 115: 230-237) (Year: 2010).*
Yamada et al (Stem Cells, 2016, 34: 2852-2860) (Year: 2016).*
Guckman et al., *Current Opinion in Immunology*, 18(5): 565-570 (2006).
Klingemann et al., *Blood*, 116(21): 4299 (2010).
Kopp et al., *Blood*, 114(22): 2664 (2009).
Zeis et al., *British Journal of Haematology*, 96(4): 757-761 (1997).
Haraguchi et al., *Journal of Immunology*, 175: 1320-1328 (2005).
Hashimoto et al., *Journal of Immunology*, 174: 551-556 (2005).
Ichikawa et al., *Clinical Immunology & Allergology*, 54(4): 472-476 (2010).
Kim et al., *Journal of Immunology*, 178(10): 6579-6587 (2007).
Leveson-Gower et al., *Blood*, 117(11): 3220-3229 (2011).
Pillai et al., *Journal of Immunology*, 178: 6242-6251 (2007).

(Continued)

*Primary Examiner* — G. R. Ewoldt
*Assistant Examiner* — Marianne DiBrino
(74) *Attorney, Agent, or Firm* — Leydig, Voit & Mayer, Ltd.

(57) ABSTRACT

The present invention provides an agent for an immunocyte therapy, comprising an NKT cell obtained by differentiating in vitro a cell having the α-chain region of the T cell receptor gene rearranged to uniform Vα-Jα in an NKT cell receptor-specific way, wherein an administration subject is an allogenic individual having MHC gene loci including at least one locus having a genotype different from that of the NKT cell. In addition, the present invention provides a bank of a human cell or an NKT cell derived from said cell, wherein the α-chain region of a T cell receptor (TCR) gene has been rearranged to uniform Vα-Jα. The agent and cell bank of the present invention are useful for the prophylaxis and/or treatment of cancer, infection, an allergic disease or an autoimmune disease.

9 Claims, 30 Drawing Sheets
Specification includes a Sequence Listing.

(56) References Cited

OTHER PUBLICATIONS

Watarai et al., *The Journal of Clinical Investigation*, 120(7): 2610-2618 (2010).
Japanese Patent Office, International Search Report in International Patent Application No. PCT/JP2011/077990 (dated Jan. 31, 2012).
Cui et al., "Requirement for $V_\alpha 14$ NKT Cells in IL-12-Mediated Rejection of Tumors," *Science*, 278(5343): 1623-1626 (1997).
Godfrey et al., "Going both ways: immune regulation via CD1d-dependent NKT cells," *J. Clin. Invest.*, 144(10): 1379-1388 (2004).
Taniguchi et al., "The NKT cell system: bridging innate and acquired immunity," *Nat. Immunol.*, 4(12): 1164-1165 (2003).
Slavin et al., "Immunotherapy in high-risk chemotherapy-resistant patients with metastatic solid tumors and hematological malignancies using intentionally mismatched donor lymphocytes activated with rIL-2: a phase I study," *Cancer Immunol. Immunother.*, 59: 1511-1519 (2010).

\* cited by examiner

Fig 11
(A)
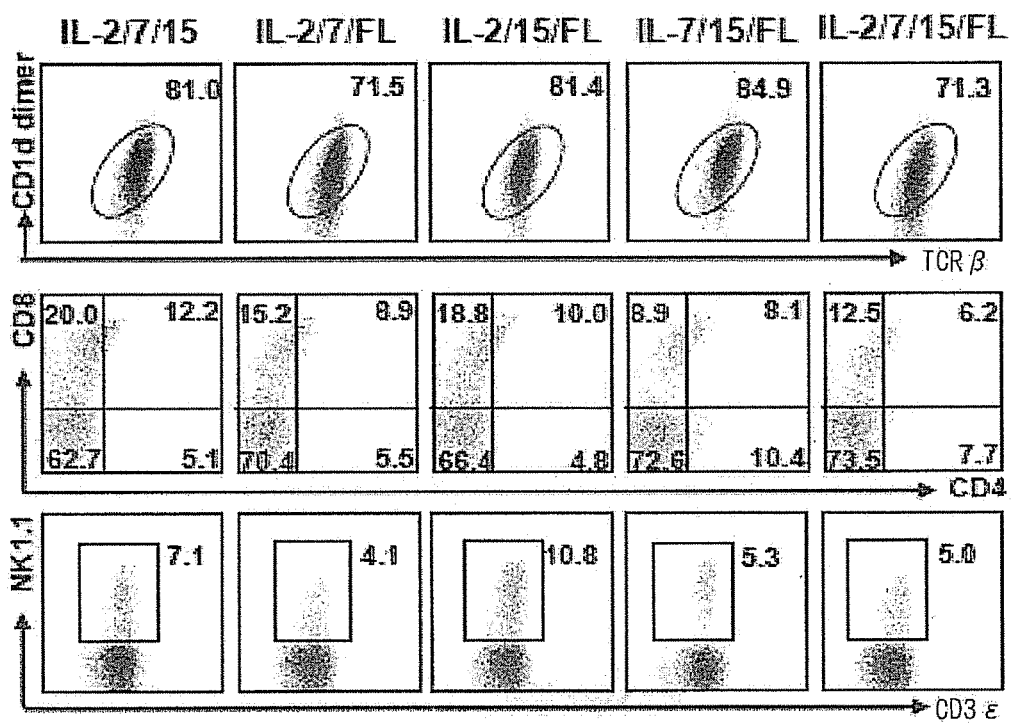
(B)
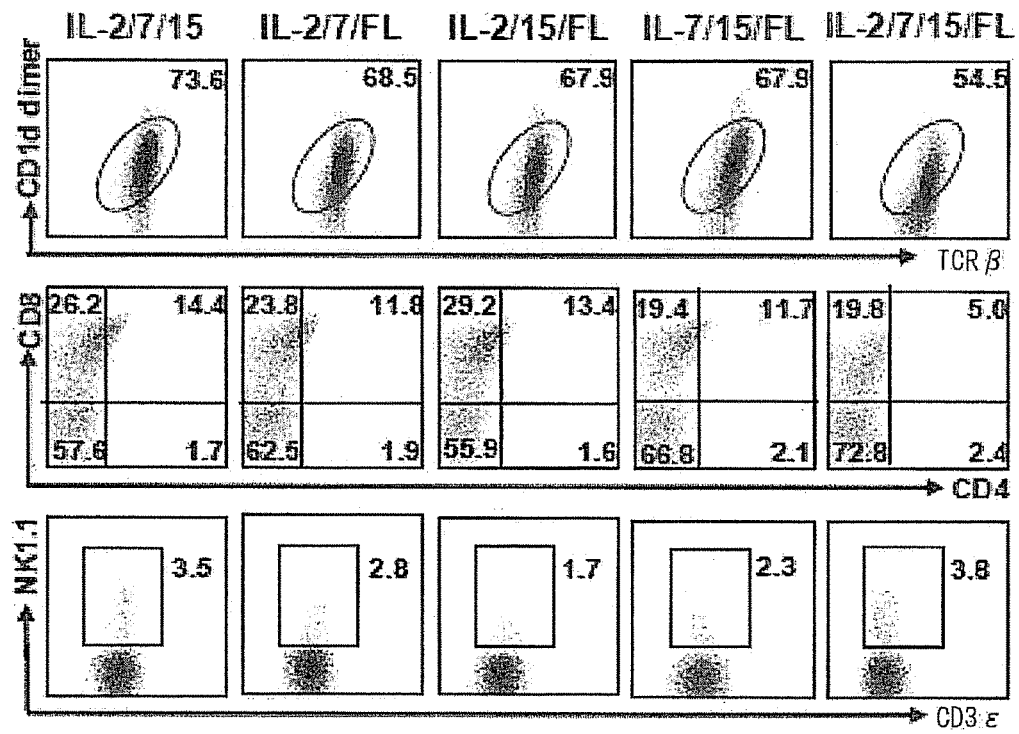

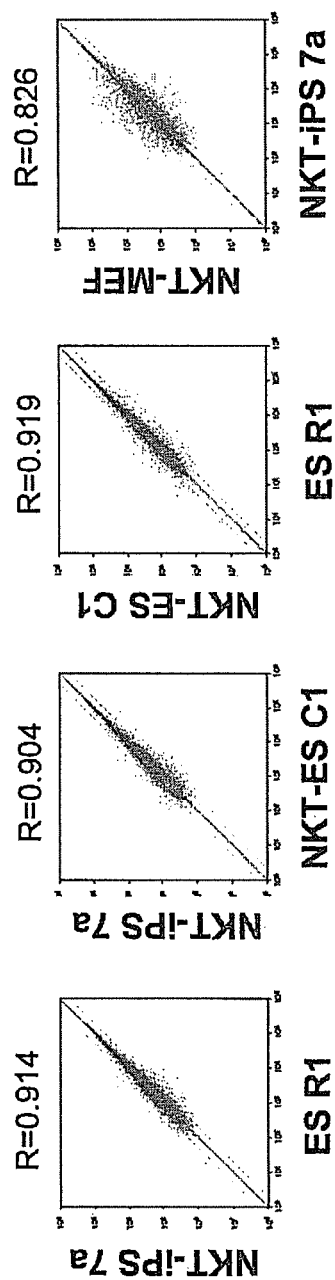
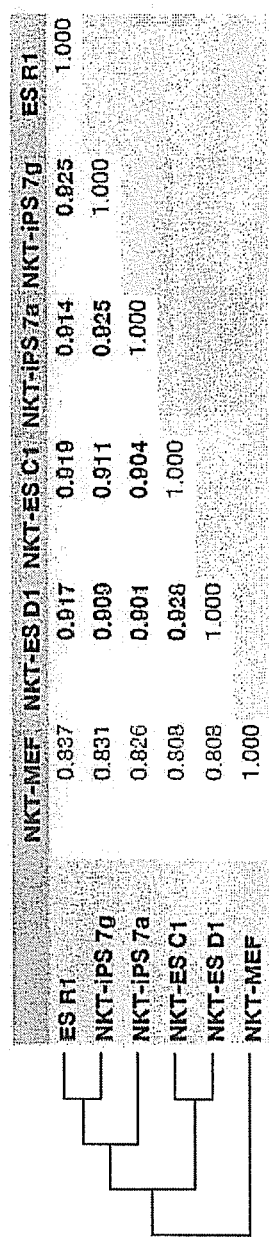
Fig. 19

Fig. 29
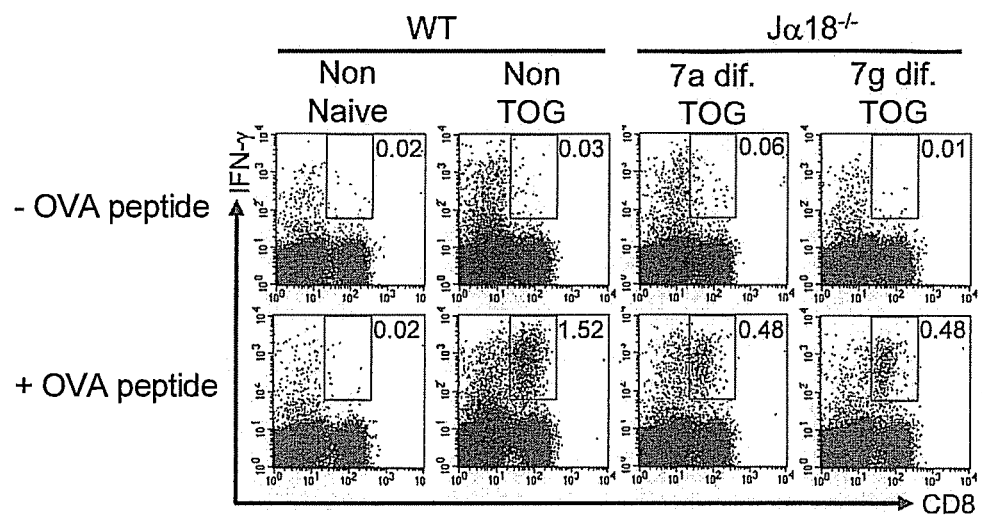
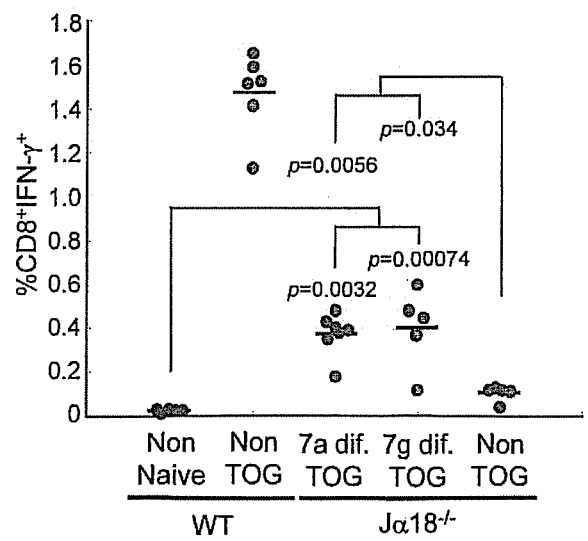

Fig. 33
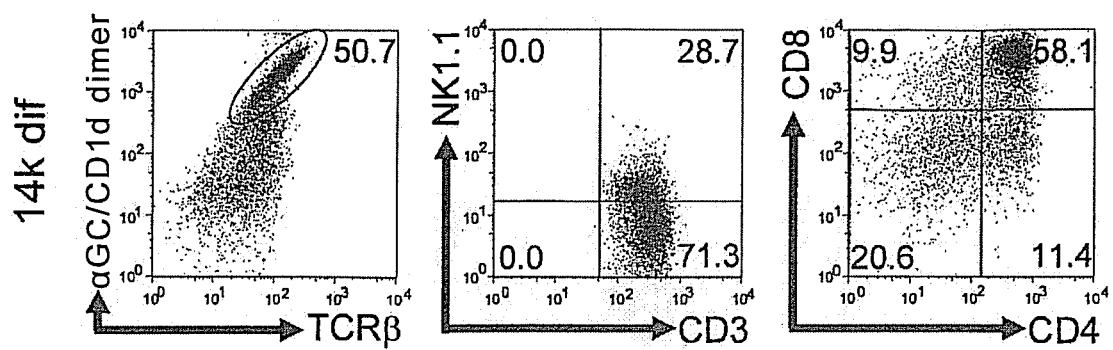
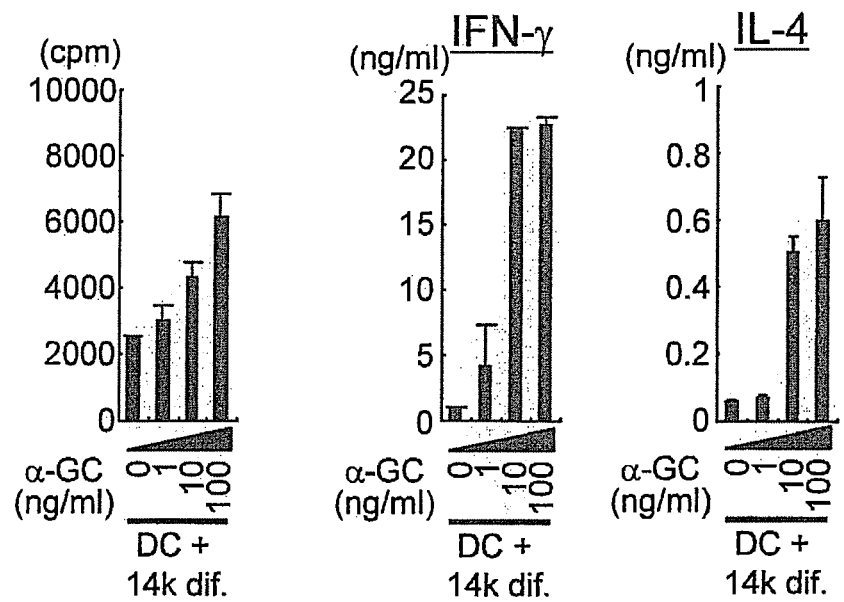

days after transplantation

SEQUENCE LISTING

<160> NUMBER OF SEQ ID NOS: 29

<210> SEQ ID NO 1
<211> LENGTH: 22
<212> TYPE: DNA
<213> ORGANISM: Artificial Sequence
<220> FEATURE:
<223> OTHER INFORMATION: primer for mouse TCR alpha

<400> SEQUENCE: 1
gacccaagtg gagcagagtc ct                                          22

<210> SEQ ID NO 2
<211> LENGTH: 24
<212> TYPE: DNA
<213> ORGANISM: Artificial Sequence
<220> FEATURE:
<223> OTHER INFORMATION: primer for human TCR alpha

<400> SEQUENCE: 2
tcacctatgt ctcctggaag cctc                                        24

<210> SEQ ID NO 3
<211> LENGTH: 25
<212> TYPE: DNA
<213> ORGANISM: Artificial Sequence
<220> FEATURE:
<223> OTHER INFORMATION: primer for mouse TCR alpha

<400> SEQUENCE: 3
cagctccaaa atgcagcctc cctaa                                       25

<210> SEQ ID NO 4
<211> LENGTH: 23
<212> TYPE: DNA
<213> ORGANISM: Artificial Sequence
<220> FEATURE:
<223> OTHER INFORMATION: primer for mouse Oct3/4

<400> SEQUENCE: 4
tctttccacc aggcccccgg ctc                                         23

<210> SEQ ID NO 5
<211> LENGTH: 23
<212> TYPE: DNA
<213> ORGANISM: Artificial Sequence
<220> FEATURE:
<223> OTHER INFORMATION: primer for mouse Oct3/4

<400> SEQUENCE: 5
tgcgggcgga catggggaga tcc                                         23

<210> SEQ ID NO 6
<211> LENGTH: 23
<212> TYPE: DNA
<213> ORGANISM: Artificial Sequence
<220> FEATURE:
<223> OTHER INFORMATION: primer for mouse Sox2

<400> SEQUENCE: 6
tagagctaga ctccgggcga tga                                         23

<210> SEQ ID NO 7
<211> LENGTH: 23
<212> TYPE: DNA
<213> ORGANISM: Artificial Sequence

```
<220> FEATURE:
<223> OTHER INFORMATION: primer for mouse Sox2

<400> SEQUENCE: 7
ttgccttaaa caagaccacg aaa                                               23

<210> SEQ ID NO 8
<211> LENGTH: 24
<212> TYPE: DNA
<213> ORGANISM: Artificial Sequence
<220> FEATURE:
<223> OTHER INFORMATION: primer for mouse Klf4

<400> SEQUENCE: 8
gcgaactcac acaggcgaga aacc                                              24

<210> SEQ ID NO 9
<211> LENGTH: 23
<212> TYPE: DNA
<213> ORGANISM: Artificial Sequence
<220> FEATURE:
<223> OTHER INFORMATION: primer for mouse Klf4

<400> SEQUENCE: 9
tcgcttcctc ttcctccgac aca                                               23

<210> SEQ ID NO 10
<211> LENGTH: 28
<212> TYPE: DNA
<213> ORGANISM: Artificial Sequence
<220> FEATURE:
<223> OTHER INFORMATION: primer for mouse c-Myc

<400> SEQUENCE: 10
tgacctaact cgaggaggag ctggaatc                                          28

<210> SEQ ID NO 11
<211> LENGTH: 32
<212> TYPE: DNA
<213> ORGANISM: Artificial Sequence
<220> FEATURE:
<223> OTHER INFORMATION: primer for mouse c-Myc

<400> SEQUENCE: 11
aagtttgagg cagttaaaat tatggctgaa gc                                     32

<210> SEQ ID NO 12
<211> LENGTH: 28
<212> TYPE: DNA
<213> ORGANISM: Artificial Sequence
<220> FEATURE:
<223> OTHER INFORMATION: primer for mouse Ecat1

<400> SEQUENCE: 12
tgtggggccc tgaaaggcga gctgagat                                          28

<210> SEQ ID NO 13
<211> LENGTH: 28
<212> TYPE: DNA
<213> ORGANISM: Artificial Sequence
<220> FEATURE:
<223> OTHER INFORMATION: primer for mouse Ecat1

<400> SEQUENCE: 13
atgggccgcc atacgacgac gctcaact                                          28
```

```
<210> SEQ ID NO 14
<211> LENGTH: 20
<212> TYPE: DNA
<213> ORGANISM: Artificial Sequence
<220> FEATURE:
<223> OTHER INFORMATION: primer for mouse Nanog

<400> SEQUENCE: 14
caggtgtttg agggtagctc                                                  20

<210> SEQ ID NO 15
<211> LENGTH: 20
<212> TYPE: DNA
<213> ORGANISM: Artificial Sequence
<220> FEATURE:
<223> OTHER INFORMATION: primer for mouse Nanog

<400> SEQUENCE: 15
cggttcatca tggtacagtc                                                  20

<210> SEQ ID NO 16
<211> LENGTH: 24
<212> TYPE: DNA
<213> ORGANISM: Artificial Sequence
<220> FEATURE:
<223> OTHER INFORMATION: primer for mouse Gdf3

<400> SEQUENCE: 16
gttccaacct gtgcctcgcg tctt                                             24

<210> SEQ ID NO 17
<211> LENGTH: 26
<212> TYPE: DNA
<213> ORGANISM: Artificial Sequence
<220> FEATURE:
<223> OTHER INFORMATION: primer for mouse Gdf3

<400> SEQUENCE: 17
agcgaggcat ggagagagcg gagcag                                           26

<210> SEQ ID NO 18
<211> LENGTH: 24
<212> TYPE: DNA
<213> ORGANISM: Artificial Sequence
<220> FEATURE:
<223> OTHER INFORMATION: primer for mouse Rex1

<400> SEQUENCE: 18
acgagtggca gtttcttctt ggga                                             24

<210> SEQ ID NO 19
<211> LENGTH: 24
<212> TYPE: DNA
<213> ORGANISM: Artificial Sequence
<220> FEATURE:
<223> OTHER INFORMATION: primer for mouse Rex1

<400> SEQUENCE: 19
tatgactcac ttccaggggg cact                                             24

<210> SEQ ID NO 20
<211> LENGTH: 24
<212> TYPE: DNA
<213> ORGANISM: Artificial Sequence
<220> FEATURE:
<223> OTHER INFORMATION: primer for mouse Zfp296
```

```
<400> SEQUENCE: 20
ccattagggg ccatcatcgc tttc                                          24

<210> SEQ ID NO 21
<211> LENGTH: 24
<212> TYPE: DNA
<213> ORGANISM: Artificial Sequence
<220> FEATURE:
<223> OTHER INFORMATION: primer for mouse Zfp296

<400> SEQUENCE: 21
cactgctcac tggagggggc ttgc                                          24

<210> SEQ ID NO 22
<211> LENGTH: 20
<212> TYPE: DNA
<213> ORGANISM: Artificial Sequence
<220> FEATURE:
<223> OTHER INFORMATION: primer for mouse HPRT

<400> SEQUENCE: 22
ctgtgtgctc aaggggggct                                               20

<210> SEQ ID NO 23
<211> LENGTH: 29
<212> TYPE: DNA
<213> ORGANISM: Artificial Sequence
<220> FEATURE:
<223> OTHER INFORMATION: primer for mouse HPRT

<400> SEQUENCE: 23
ggactcctcg tatttgcaga ttcaacttg                                     29

<210> SEQ ID NO 24
<211> LENGTH: 75
<212> TYPE: DNA
<213> ORGANISM: Mus musculus
<220> FEATURE:
<221> NAME/KEY: CDS
<222> LOCATION: (1)..(75)

<400> SEQUENCE: 24 gtg ggg gat aga ggt tca gcc tta ggg agg ctg cat ttt gga gct ggg    48
Val Gly Asp Arg Gly Ser Ala Leu Gly Arg Leu His Phe Gly Ala Gly
 1               5                  10                  15 act cag ctg att gtc ata cct gac atc                                75
Thr Gln Leu Ile Val Ile Pro Asp Ile
             20                  25

<210> SEQ ID NO 25
<211> LENGTH: 25
<212> TYPE: PRT
<213> ORGANISM: Mus musculus

<400> SEQUENCE: 25

Val Gly Asp Arg Gly Ser Ala Leu Gly Arg Leu His Phe Gly Ala Gly
 1               5                  10                  15

Thr Gln Leu Ile Val Ile Pro Asp Ile
             20                  25

<210> SEQ ID NO 26
<211> LENGTH: 69
<212> TYPE: DNA
<213> ORGANISM: Mus musculus
```

```
<220> FEATURE:
<221> NAME/KEY: CDS
<222> LOCATION: (1)..(69)

<400> SEQUENCE: 26 agc agt gag cca gca aac tcc gac tac acc ttc ggc tca ggg acc agg        48
Ser Ser Glu Pro Ala Asn Ser Asp Tyr Thr Phe Gly Ser Gly Thr Arg
1               5                   10                  15 ctt ttg gta ata gag gat ctg                                            69
Leu Leu Val Ile Glu Asp Leu
            20

<210> SEQ ID NO 27
<211> LENGTH: 23
<212> TYPE: PRT
<213> ORGANISM: Mus musculus

<400> SEQUENCE: 27

Ser Ser Glu Pro Ala Asn Ser Asp Tyr Thr Phe Gly Ser Gly Thr Arg
1               5                   10                  15

Leu Leu Val Ile Glu Asp Leu
            20

<210> SEQ ID NO 28
<211> LENGTH: 60
<212> TYPE: DNA
<213> ORGANISM: Mus musculus
<220> FEATURE:
<221> NAME/KEY: CDS
<222> LOCATION: (1)..(60)

<400> SEQUENCE: 28 gat tcc ggg aca gca gaa gtc ttc ttt ggt aaa gga acc aga ctc aca        48
Asp Ser Gly Thr Ala Glu Val Phe Phe Gly Lys Gly Thr Arg Leu Thr
1               5                   10                  15 gtt gta gag gat                                                        60
Val Val Glu Asp
            20

<210> SEQ ID NO 29
<211> LENGTH: 20
<212> TYPE: PRT
<213> ORGANISM: Mus musculus

<400> SEQUENCE: 29

Asp Ser Gly Thr Ala Glu Val Phe Phe Gly Lys Gly Thr Arg Leu Thr
1               5                   10                  15

Val Val Glu Asp
            20
```

IMMUNOTHERAPY USING ALLO-NKT CELLS, CELLS FOR IMMUNOTHERAPY IN WHICH ALPHA CHAIN OF T-CELL RECEPTOR (TCR) GENE HAS BEEN REARRANGED TO UNIFORM Vα-Jα, AND BANKING OF NKT CELLS DERIVED FROM SAID CELLS

CROSS-REFERENCE TO RELATED APPLICATIONS

This patent application is the U.S. national phase of International Patent Application No. PCT/JP2011/077990, filed Dec. 2, 2011, which claims the benefit of U.S. Patent Application No. 61/419,064, filed on Dec. 2, 2010.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 7,473 bytes ASCII (Text) file named "ReplacementSequenceListing.txt," created on May 23, 2017.

TECHNICAL FIELD

The present invention relates to immunotherapy using allo-NKT cells derived from cells wherein the α-chain (TCRα) region of the T cell antigen receptor (TCR) gene have been rearranged to uniform Vα-Jα in an NKT cell receptor-specific manner, and banking of cells therefor wherein the α-chain region of the T cell antigen receptor (TCR) gene has been rearranged to uniform Vα-Jα in an NKT cell receptor-specific manner and NKT cells derived from said cells.

BACKGROUND ART

In Japan, the number of deaths due to cancer is more than 340,000 people per year, and cancer is the No. 1 cause of death ("Annual Estimation of Population Survey Report", 2009, Ministry of Health, Labour and Welfare). As for the number of deaths by cancer site, lung cancer is the highest (48,610) in male and the second highest (18,239) in female (survey by National Cancer Center, Center for Cancer Control and Information Services in 2008). It is considered that the cancer cells have already spread throughout the body before a lung cancer surgery, as a result of which 50% of the patients suffer from recurrence after the surgery, thereby increasing the number of deaths for each cancer site.

At present, the "advanced medical treatment of cancer" using immunocyte includes an auto-lymphocyte transfer therapy wherein lymphocytes of patient are activated ex vivo and returned to the patient's body, a cancer peptide vaccine therapy and the like; however, the effects are still insufficient. When an antitumor effect is expected, an adjuvant action is indispensable. Unlike pathogens, cancer cells do not show an adjuvant effect by themselves, and therefore, general immunotherapy sometimes cannot provide a sufficient treatment effect. In addition, cancer tissue includes "two kinds of cancer cells": "cancer cells expressing MHC molecules" and "cancer cells that have lost MHC molecules". Unless these "two kinds of cancer cells" are simultaneously eradicated, cancer cannot be treated drastically. In addition, the development of a treatment method capable of targeting any cancer and usable for any kind of cancer is desired.

The present inventors have clarified that a lymphocyte, Natural Killer T cell (NKT cell), shows an adjuvant action and has a superior anticancer effect, and further developed a new treatment method that attacks cancer cells via activation of NKT cells. That is, NKT cells exert a strong immunopotentiating action by an adjuvant action, and recruit other cells (NK cells, CTLs etc.) in the immune system to kill cancer cells. They have recently clarified that, in this case, an "adjuvant immunocyte therapy" is effective, which includes administration of dendritic cells pulsed with synthetic glycolipid α-galactosylceramide (α-GalCer), that activates NKT cells, to cancer patients.

Heretofore, phase I and phase II clinical trials of the aforementioned adjuvant immunocyte therapy have been completed for 17 cases of advanced lung cancer or recurrent lung cancer. As a result, prolongation of the survival time for 19 months on average was observed in all cases by an initial treatment alone, whereby significant prolongation of survival time was found as compared to that of the treatment with molecule targeting drugs currently in use (about 10 months on average). The median value of the survival time of patients who responded well to this treatment method (60% of all cases) was 31.9 months, which was not less than 3 times that by the molecule targeting drug treatment. In other cases, the average survival time was 9.6 months, which was equivalent to the effect of the molecule targeting drug treatment (non-patent document 1).

However, about ⅔ of the patients with advanced lung cancer or recurrent lung cancer show a decreased number of NKT cells, and do not satisfy the entry criteria of this therapy. Therefore, only about ⅓ of the patients can be the target of this therapy.

Once a technique for increasing in vitro the NKT cells collected from the patients themselves is developed, the adjuvant immunocyte therapy is expected to be an effective treatment method targeting a broader range of patients. However, NKT cells are normally present in a trace amount of not more than 0.1% of the peripheral blood lymphocytes, and the function itself of NKT cells may have decreased in cancer patients. In addition, a technique for efficiently expanding NKT cells in vitro in a number sufficient for the treatment has not been established yet.

Provided that an NKT cell clone can be obtained in large amounts by reprogramming the NKT cells collected, and the like, expanding them into a large amount and then allowing them to differentiate and mature again, it is expected that the therapeutic effect of NKT cell immunotherapy can be improved.

The present inventors have succeeded in producing NKT cells in a large amount by differentiating ES cells transplanted with the nucleus of a NKT cell into NKT cells in vitro (patent document 1).

In addition, the present inventors have introduced 4 factors of Oct3/4, Sox2, Klf4 and c-Myc into mouse spleen-derived NKT cells and successfully established cells having properties characteristic of iPS cells, wherein the α-chain region of the T cell antigen receptor (TCR) gene has been rearranged to Vα14-Jα18 (hereinafter to be referred to as "NKT-iPS cells"), and further, differentiated the iPS cells into functionally matured NKT cells (hereinafter to be referred to as "iPS-NKT cells") for the first time in the world (patent document 2, non-patent document 2). Generally, finally differentiated cells are less easy to be reprogrammed than undifferentiated cells. As for B cells and T cells, it has been reported that iPS cells cannot be induced with the four factors or three factors (Oct3/4, Sox2, Klf4) only, and require the use of another gene as a nuclear reprogramming factor (non-patent document 3) and p53 inhibition (non-patent document 4). Therefore, a successful establishment of iPS cells from NKT cells by using 4 factors alone is an unexpected finding. Since increasing the number of introduced gene and inhibiting p53, which is a tumor suppressor gene, are problematic in terms of safety, since they increase the tumorigenesis risk of the cells differentiated from iPS cells and the like, the achievement by the present inventors enhances the expectation of the applicability of iPS cells in the immunocyte therapy.

Nevertheless, there are still piles of problems to be solved before using differentiated cells derived from iPS cells for a transplantation therapy. Among those, one of the most difficult problems is securing of safety such as elimination of the tumorigenic risk of the engrafted cells or tissue. In view thereof, improvement of a method using a non-integration vector such as plasmid, adenovirus, Hemagglutinating Virus of Japan and the like, and a reprogramming method using protein introduction and a low-molecular-weight compound, development of a method for selecting high quality iPS cells, or preventing contamination of undifferentiated cells, and the like are ongoing. However, all these studies stand on the major premise of "transplantation therapy=engraftment".

On the other hand, graft-versus-host disease (GVHD) is known as one of the complications in transplantation therapy. This is a generic term for symptoms caused by the organ of a donor (organ provider) that attacks organ(s) of the recipient by immune responses. GVHD occurs after various allogenic organ transplantations, and is particularly known to occur after hematopoietic stem cell transplantation (bone marrow transplantation) including direct transplantation of immune tissues and after blood transfusion. GVHD caused by blood transplantation includes acute and chronic ones. The onset mechanism of the former is presumed to involve lymphocyte and that of the latter is presumed to involve many more immune functions.

NKT cell is placed as one kind of lymphocyte, and classified as a subpopulation of αβ T cells defined by the cells expressing T cell receptor α chain and β chain, which is characterized by the expression of Vα24-Jα18 α chain and vβ11 β chain in human, and Vα14-Jα18 α chain and Vβ8/7/2 β chain in mouse as a T cell antigen receptor, and include CD4 positive and CD4 negative cells (non-patent document 5). Reports have heretofore documented that NKT cells at the recipient side suppressively act on the onset of GVHD (non-patent documents 6-8). While donor-derived allo-NKT cells have been reported to act suppressively depending on the conditions in a transplantation experiment using other allo-lymphocytes in combination (non-patent document 9), there is no report on whether GVHD occurs when allo-NKT cells alone are transplanted. According to the studies made by the present inventors, allo-NKT cells normally differentiated in the body and allo-NKT cells differentiated from pluripotent stem cells in vitro are elucidated to be different in their gene expression (non-patent document 2), and there is no report relating to the relationship between NKT cells differentiated from such pluripotent stem cell and GVHD.

DOCUMENT LIST

Patent Documents patent document 1: WO2008/038579 (published on Apr. 3, 2008)
patent document 2: WO2010/027094 (published on Mar. 11, 2010)

Non-Patent Documents non-patent document 1: Motohashi S. et al., J. Immunol., 2009; 182: 2492-2501
non-patent document 2: Watarai, H. et al., J. Clin. Invest., 2010 Jun. 1; 120(7): 2610-2618
non-patent document 3: Hanna, J. et al., Cell, 2008 Apr. 18; 133(2): 250-264. Erratum in: Cell. 2008 Jul. 25; 134(2): 365
non-patent document 4: Hong, H. et al., Nature, 2009 Aug. 27; 460(7259): 1085-1086
non-patent document 5: Taniguchi M et al., Int. Immunol., 2010; 22: 1-6
non-patent document 6: Hashimoto, D. et al., The Journal of Immunology, 2005; 174; 551-556
non-patent document 7: Haraguchi, K. et al., The Journal of Immunology, 2005; 175; 1320-1328
non-patent document 8: Pillai, A. B. et al., The Journal of Immunology, 2007; 178; 6242-6251
non-patent document 9: Leveson-Gower, D. B. et al., blood, 2011 117: 3220-3229

SUMMARY OF THE INVENTION

Problems to be Solved by the Invention

An object of the present invention is to provide banking of cells derived from human NKT cells, wherein the α-chain region of the T cell antigen receptor gene (TCR) is rearranged to uniform Vα-Jα in an NKT cell receptor-specific manner and NKT cells derived from the cells, the cell-derived NKT cell, and a method of a transplantation treatment utilizing the same, which utilize the features of an immunocyte therapy and are under a completely novel conception.

Means of Solving the Problems

In an attempt to solve the above-mentioned problems, the present inventors made a novel treatment strategy of using immunocyte in a similar way to general medicaments. Since general pharmaceutical products are foreign substances to the body, they adversely influence the body when they stay in the body for too long. Therefore, it is desirable to excrete them from the body or metabolically catabolize them rapidly after exertion of a desired treatment effect. Also in the case of the immunocyte therapy, once the transplanted cells have supplemented and/or activated the immunocytes and the effect has been achieved by attacking the target disease cells, the transplanted cells do not entirely need to be engrafted to remain in the body of the patient, different from other transplantation therapies such as organ transplantation. In late stage cancer patients, since recovery of a necessary number of patients' own lymphocytes is not easy, use of allogenic cells is more realistic. Based on the preconceived concept, however, transplantation from a donor showing substantially the same type of major histocompatibility antigen (MHC) is the expected action to ensure complete engraftment. In other words, since allo-transplanted cells are rejected by the immune system of the patient, it is a common practice to transplant the cells derived from a donor having the same type of MHC with the patient, thereby ensuring long-term engraftment.

The present inventors have taken note of the fact that the transplantation of allo-NKT cells having different type of MHC from that of the recipient causes rejection of the transferred cells by immunoreaction against allo cells, whereby the side effects potentially caused by the long-term retention of the transferred cells can be avoided. To be precise, since, after the lapse of a certain period, the transferred NKT cells are excluded from the body by an immunoreaction against allo cells in the host immune system, they do not stay in the body of the host for a long time and are expected to exhibit the effect of a temporary medicament.

In the meantime, when allo-NKT cells are transplanted, whether GVHD occurs or not is highly important for the safety of the cells. As described above, there has been no report heretofore as to the presence or absence of the onset of GVHD when only the allo-NKT cells differentiated from pluripotent stem cells in vitro are transplanted, not to mention the presence or absence of the onset of GVHD when only the allo-NKT cells normally differentiated in the body are transplanted. Therefore, the safety of a transplantation therapy using only the allo-NKT cells differentiated from cells having uniform α-chain region of the T cell antigen receptor (TCR) gene needs to be verified.

To verify the above-mentioned hypothesis, therefore, the present inventors applied a technique established by the present inventors themselves, for establishing iPS cells from NKT cells that underwent a receptor gene rearrangement, and inducing differentiation of the iPS cell into mature NKT cells, and collected NKT cells from an individual having different MHC type from the recipient, established iPS cells therefrom, and further differentiated the cells into mature NKT cells. The obtained iPS-NKT cells were transplanted to the recipient, stimulated with α-GalCer, and an adjuvant effect and an antitumor effect of the transferred cells were examined. As a result, a strong adjuvant effect and a tumor growth suppressive effect were observed. Furthermore, the transplanted iPS-derived NKT cells remained in the body of the recipient for a period sufficient to show a remarkable treatment effect, and thereafter rejected and excluded by the immune system of the recipient. In addition, to verify the presence or absence of the onset of GVHD when only the allo-NKT cells differentiated from cells having uniform α-chain region of the T cell antigen receptor (TCR) gene are transplanted, NKT cells redifferentiated from the iPS cells established in vitro from NKT cells with C57BL/6 background was transplanted to a recipient free of cells of the immune system (RAG KO mouse, BALB/c background). As a result, GVHD was developed with allo CD4-positive helper T cells with C57BL/6 background isolated from the spleen used as a target group, but GVHD was not developed with allo-NKT cells prepared by redifferentiation from iPS cells established from NKT cells. According to this method, the donor can be easily obtained since MHC does not need to be matched between the donor and the recipient, and further, the safety problem of NKT cells derived from iPS cells can also be solved. Moreover, the method is safe since GVHD is not developed along with the transplantation. The present invention has been completed based on the above-mentioned findings.

Accordingly, the present invention relates to the following.

[1] An agent for an immunocyte therapy, comprising NKT cells obtained by differentiating in vitro cells having the α-chain region of the T cell antigen receptor gene rearranged to uniform Vα-Jα in an NKT cell receptor-specific manner, wherein an administration subject is an allogenic individual having MHC gene loci including at least one locus having a genotype different from that of the NKT cells.

[2] The agent of the above-mentioned [1], wherein said cells having the α-chain region of the T cell antigen receptor gene rearranged to uniform Vα-Jα in an NKT cell receptor-specific manner are pluripotent stem cells.

[3] The agent of the above-mentioned [2], wherein the pluripotent stem cells are ES cells.

[4] The agent of the above-mentioned [3], wherein the ES cells are human ES cells.

[5] The agent of the above-mentioned [4], wherein the administration subject is an allogenic individual having HLA gene loci including at least one locus having a genotype different from that of the human ES cells.

[6] The agent of the above-mentioned [2], wherein the pluripotent stem cells are iPS cells.

[7] The agent of the above-mentioned [6], wherein the iPS cells are human iPS cells.

[8] The agent of the above-mentioned [2], wherein the pluripotent stem cells are derived from an NKT cell.

[9] The agent of the above-mentioned [8], wherein the NKT cell is a human NKT cell.

[10] The agent of the above-mentioned [9], wherein an administration subject is an allogenic individual having HLA gene loci including at least one locus having a genotype different from that of the human NKT cell.

[11] The agent of the above-mentioned [5] or [10], wherein the HLA gene loci include HLA-A, HLA-B and HLA-C.

[12] The agent of any of the above-mentioned [1] to [11], which is combined with an NKT cell receptor ligand or dendritic cells pulsed with the NKT cell receptor ligand.

[13] The agent of the above-mentioned [12], wherein the NKT cell receptor ligand is α-galactosylceramide.

[14] The agent of any of the above-mentioned [1] to [13], which is for the prophylaxis and/or treatment of cancer, infection, an allergic disease or an autoimmune disease.

[15] An immunocyte therapy method for an allogenic individual having MHC gene loci including at least one locus having a genotype different from that of NKT cells, comprising administering, to the allogenic individual, an effective amount of NKT cells obtained by differentiating in vitro cells, wherein the α-chain region of a T cell antigen receptor gene have been rearranged to uniform Vα-Jα in an NKT cell receptor-specific manner.

[16] The method of the above-mentioned [15], wherein the cells wherein the α-chain region of the T cell receptor gene have been rearranged to uniform Vα-Jα in an NKT cell receptor-specific manner are pluripotent stem cells.

[17] The method of the above-mentioned [16], wherein the pluripotent stem cells are ES cells.

[18] The method of the above-mentioned [17], wherein the ES cells are human ES cells.

[19] The method of the above-mentioned [16], wherein the pluripotent stem cells are iPS cells.

[20] The method of the above-mentioned [19], wherein the iPS cells are human iPS cells.

[21] The method of the above-mentioned [16], wherein the pluripotent stem cells are derived from an NKT cell.

[22] The method of the above-mentioned [22], wherein the NKT cell is a human NKT cell.

[23] The method of the above-mentioned [22], wherein the administration subject is an allogenic individual wherein at least one of the HLA gene loci has a genotype different from that of the human NKT cell.

[24] The method of the above-mentioned [23], wherein the HLA gene locus includes HLA-A, HLA-B and HLA-C.

[25] The method of any of the above-mentioned [15] to [24], further comprising administering an effective amount of an NKT cell receptor ligand or dendritic cells pulsed with the NKT cell receptor ligand to the aforementioned individual.
[26] The method of the above-mentioned [25], wherein the NKT cell receptor ligand is α-galactosylceramide.
[27] The method of any of the above-mentioned [15] to [26], which is for the prophylaxis and/or treatment of cancer, infection, an allergic disease or an autoimmune disease.
[28] A bank of human NKT cell-derived cells wherein the α-chain region of the T cell receptor gene have been rearranged to uniform Vα-Jα in an NKT cell receptor-specific manner, or NKT cells obtained by differentiating said cells in vitro.
[29] A method of constructing the bank of the above-mentioned [28], comprising the following steps (1)-(4):
(1) determining the genotype of a particular HLA gene locus of a donor registrant;
(2) collecting NKT cells from the donor registrant;
(3) establishing, from said NKT cells, human cells having the α-chain region of the T cell receptor gene rearranged to uniform Vα-Jα in an NKT cell receptor-specific manner, and establishing, where necessary, human NKT cells from the established human cells; and
(4) evaluating the differentiation potency of the established human cells into NKT cells, and tumorigenicity after the differentiation, and successively banking human cell or NKT cell derived from said cells, which satisfy the criteria.
[30] An immunocyte therapy method comprising
(1) being furnished with cells wherein the α-chain region of a T cell receptor gene has been rearranged to uniform Vα-Jα in an NKT cell receptor-specific manner, which have been established from a human NKT cell wherein at least one of the HLA gene loci has a genotype different from that of a patient in need of the administration of human NKT cells, or an NKT cells derived from said cells, from the bank in the above-mentioned [28],
(2) when furnish with cells wherein the α-chain region of a T cell receptor gene has been rearranged to uniform Vα-Jα in an NKT cell receptor-specific manner, which has been established from a human NKT cell, in (1), inducing differentiation of the cells into mature NKT cells,
(3) administering an effective amount of the human NKT cells obtained in the above-mentioned (1) or (2) to the patient.
[31] The method of the above-mentioned [30], further comprising administering an effective amount of an NKT cell receptor ligand or dendritic cells pulsed with the NKT cell receptor ligand to the aforementioned patient.
[32] The method of the above-mentioned [31], wherein the NKT cell receptor ligand is α-galactosylceramide.
[33] The method of any of the above-mentioned [30] to [32], which is for the prophylaxis and/or treatment of cancer, infection, an allergic disease or an autoimmune disease.

Effect of the Invention

The present invention is based on a completely new idea of utilizing transplanted cells in a manner similar to that of general medicaments, in which the cells disappear after exerting efficacy in the body for an appropriate period. The property that the transferred cells are excluded by the host immune system when HLA is different between a donor and the recipient is utilized. For example, iPS cells are established from a human (donor) NKT cells wherein A, B and C gene loci are completely mismatched, maintained and expanded, the iPS cells are induced to differentiate into NKT cells when in use, and the obtained NKT cells are transplanted to the patient (recipient). Since the transplanted NKT cells have A, B and C haplotypes different from those of the recipient, is the NKT cells are not engrafted but excluded by the host immune system, during which the NKT cells are expected to be able to exert a sufficient adjuvant effect.

According to the present invention, the treatment can be performed also for patients with advanced cancer or recurrence cancer who conventionally could not satisfy the entry criteria of adjuvant immunocyte therapy due to a decreased number of NKT cells.

Since NKT cells are rejected by an immunoreaction against allo cells even when transferred into a normal allo individual, an immunocyte therapy can be performed safely.

Since NKT cells differentiated from cells wherein the α-chain region of a T cell antigen receptor (TCR) gene has been rearranged to uniform Vα-Jα in an NKT cell receptor-specific manner do not cause GVHD when transfected into an allo individual, side effects caused by GVHD can be avoided.

NKT cells are selectively induced from cells wherein the TCR α-chain region on the chromosome has been rearranged uniformly in an NKT cell-specific manner. Thus, when NKT cells induced from said cells are used for the immunocyte therapy of the present invention, the possibility of contamination with conventional allo-T cells can be avoided, and the risk of developing severe GVH reaction can be suppressed.

In the immunocyte therapy of the present invention, since HLA of a donor and the recipient does not need to be matched, a donor can be easily obtained. Therefore, NKT cells can be stably supplied by banking cells, such as iPS cells, wherein the α-chain (TCRα) region of the T cell antigen receptor (TCR) gene has been rearranged to uniform Vα-Jα in an NKT cell-specific manner induced from NKT cells provided by a donor, and the like, or NKT cells derived from said cells. Since the same effect can be expected from any HLA type of cells derived from a human NKT cell wherein the α-chain (TCRα) region of a T cell receptor (TCR) gene has been rearranged to uniform Vα-Jα, and NKT cells derived from said cells, it is possible to immediately prepare allo-NKT cells effective for patients of any HLA type and use the cells for the treatment.

BRIEF DESCRIPTION OF THE DRAWINGS

FIG. 11 is a drawing showing the expression of invariant TCRα, the expression of CD4/CD8, and the expression of NK1.1 in cells obtained by co-culturing DP-NKT cells with stromal cells that (A) do not express/(B) express a Notch ligand using various combinations of cytokines.

FIG. 19 is a drawing showing a DNA microarray analysis and correlation analysis of NKT-iPS cell clones 7a and 7g.

FIG. 29 is a drawing showing the induction of antigen specific CD8-positive T cells by cells 7a dif. and 7g dif. differentiation-induced in vitro.

FIG. 33 is a drawing showing an in vitro functional evaluation of cells differentiation-induced from NKT-iPS clone 14k.

DESCRIPTION OF EMBODIMENTS

Figure 1:
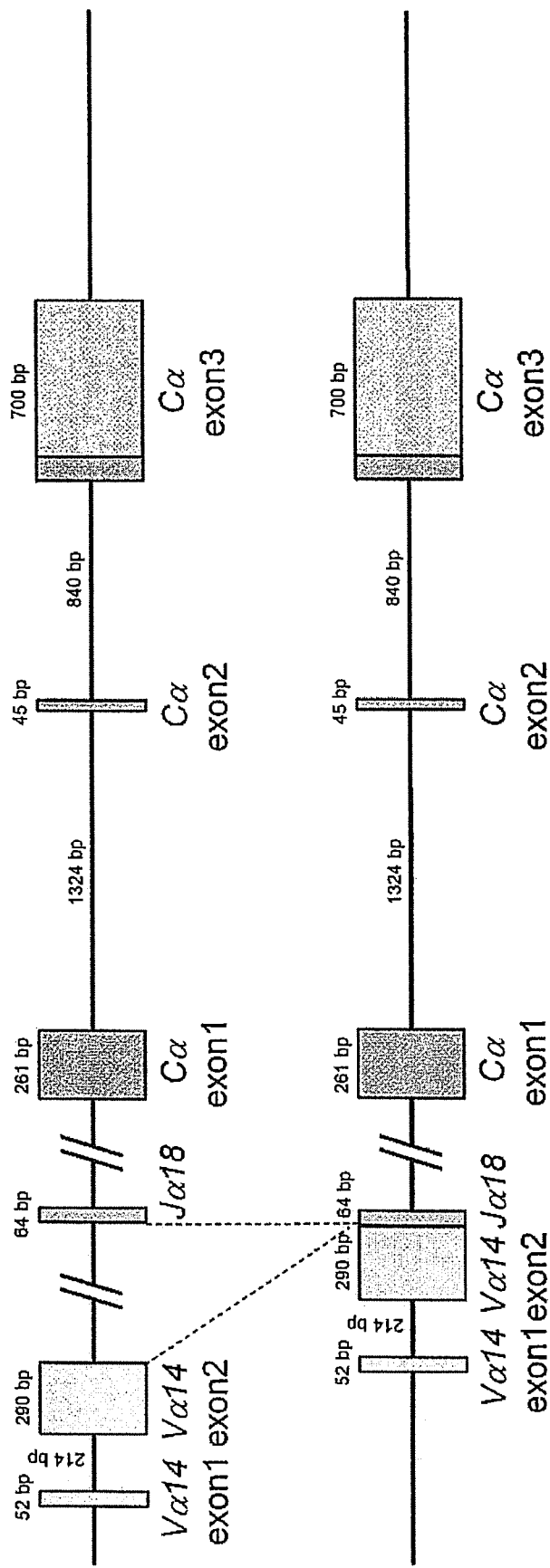
FIG. 1 is a schematic diagram of the TCRα gene loci of wild type and NKT cell.

The agent for an immunocyte therapy of the present invention contains, as an active ingredient, NKT cells obtained by differentiating in vitro cells (excluding NKT cells) having self-renewal capacity and capacity to differentiate into NKT cells, and having the α-chain region (TCRα) of the TCR gene rearranged to uniform Vα-Jα in an NKT cell receptor-specific manner. While such cells are not particularly limited as long as the α-chain (TCRα) region of the TCR gene is rearranged to uniform Vα-Jα in an NKT cell receptor-specific manner, examples thereof include iPS cells established from an NKT cell wherein the rearrangement has been completed (i.e., cells wherein the α-chain (TCRα) region of a TCR gene has been rearranged to uniform Vα-Jα in an NKT cell receptor-specific manner, which possess properties characteristic of iPS cell such as self-renewal property and pluripotency, an ES cell-like gene expression pattern and the like (NKT-iPS cell)), pluripotent stem cells wherein the α-chain (TCRα) region of a TCR gene has been rearranged to uniform Vα-Jα in an NKT cell receptor-specific manner or wherein uniform Vα-Jα of an NKT cell receptor-specific manner has been inserted into a particular region on the genome to enable expression thereof, by inserting a gene into pluripotent stem cells to enable expression of the α chain and β chain of an NKT cell-specific TCR gene, pluripotent stem cells established from an NKT cell nuclear transferred embryo, cells established from an NKT cell wherein the rearrangement has been completed, and having at least redifferentiation capacity into an NKT cell (e.g., hematopoietic stem cell) and the like.

In the present specification, the "pluripotent stem cell" means a stem cell that can be cultivated in vitro, and having an ability to differentiate into any cell constituting the body (tissues derived from three germ layers (ectoderm, mesoderm, endoderm)) except placenta (pluripotency). The pluripotent stem cell includes iPS cell, embryonic stem cell (ES cell), embryonic germ cell (EG cell) and the like.

In the present invention, cells of mammals are generally used. Examples of the mammal include experiment animals such as rodents (e.g., mouse, rat, hamster, guinea pig and the like), rabbit and the like, domestic animals such as swine, bovine, goat, horse, sheep and the like, companion animals such as dog, cat and the like, and primates such as human, monkey, orangutan, chimpanzee and the like. The mammals are preferably rodents (mouse etc.) or primates (human etc.), more preferably mouse or human.

As used herein, "an iPS cell" refers to a cell that has acquired pluripotency and self-renewal competence conferred artificially by contacting nuclear reprogramming factors with a somatic cell, and that is similar to ES cells in terms of gene expression profile. Here, "pluripotency" means the ability to differentiate into a plurality of series of immunohepatopoietic cells such as NKT cells, T cells, B cells, erythrocytes, macrophages and progenitor cells thereof, as well as into one or more cell series other than the hematopoietic-immune system, and is distinguished from multipotency in hematopoietic stem cells and multipotent progenitor cells. "self-renewal competence" means the ability for a cell to continue to expand in a particular environment (e.g., conditions suitable for culturing ES cells) while retaining the above-described "pluripotency". Furthermore, "similar to ES cells in terms of gene expression profile" means that the correlation coefficient (r) between the data set of gene expression in the subject cells and the data set of gene expression in ES cells is 0.9 or more. ES cells for the comparison include ES cells generated from a fertilized egg derived from the same species, preferably from the same strain, ES cells generated from an NKT cell nuclear transferred embryo, and the like.

The NKT-iPS cells of the present invention can be cells having the α chain region of the TCR gene (TCRα) rearranged to uniform Vα-Jα in an NKT cell receptor-specific manner, and possessing properties characteristic of iPS cells, such as self-renewal competence, pluripotency, and an ES cell-like gene expression pattern. The term "an NKT cell receptor-specific manner" will be described below.

The NKT-iPS cell of the present invention can be established by contacting somatic cells having the α chain region of the TCR gene (TCRα) rearranged to uniform Vα-Jα in an NKT cell receptor-specific manner, such as NKT cells, with nuclear reprogramming factors. Herein, the "NKT cell" is not particularly limited, as far as either TCRα region is rearranged to uniform Vα-Jα, and it is used with a meaning encompassing not only mature NKT cells (characterized by, for example, NK1.1$^+$/CD3ε$^+$), but also progenitor cells thereof (cells characterized by, for example, CD4$^+$/CD8$^+$ and the like). NKT cells can be isolated from the spleen, lymph node, peripheral blood, cord blood and the like by a method known per se, for example, flow cytometry using an antibody against the above-described cell surface markers or CD1d multimer (dimer, tetramer etc.) pulsed with α-galactosylceramide and a cell sorter. In the case of mice, it is preferable to collect NKT cells from the spleen or lymph node, wherein the abundance ratio of NKT cells is high; however, in the case of humans, it is desirable, from the viewpoint of low invasiveness and the ease of preparation, that the NKT cells be prepared from peripheral blood, cord blood and the like.

The NKT cell used for the production of an NKT-iPS cell in the present invention may be derived from any animal species that permits the establishment of NKT-iPS cells by contacting nuclear reprogramming factors with the NKT cell; specifically, those of human or mouse derivation can be mentioned, and human-derived NKT cells are preferred. Human or mouse, which is a collection source of NKT cells, is an allogenic individual wherein at least one of the major gene loci in MHC has a genotype different from that of a target of immunocyte therapy, preferably an allogenic individual wherein all loci have genotypes different from those of the target. Thus, since at least one of the MHC gene loci is mismatched in genotype between the two, the administered NKT cells are recognized by the immune system of the recipient and finally excluded. As the MHC gene loci in the case of general human organ transplantation, match or no-match of 3 gene loci of HLA-A, HLA-B and HLA-C is the criteria of the compatibility. Accordingly, an individual wherein at least one locus of these 3 gene loci is different from that of the recipient is generally selected as a donor. In mouse, similarly, the H-2K, H-2D and H-2L gene loci in class I region can be recited as the major gene loci in the present invention.

In one embodiment, NKT cells derived from an individual having a different genotype of at least 1 locus (preferably 2 loci, more preferably 3 loci), among the above-mentioned 3 gene loci, from that of the target individual of the immunocyte therapy are used. In this embodiment, since the administered NKT cells are excluded by an immunoreaction against allo cells of the recipient due to the mismatch of MHC gene locus, exclusion of the cells after effective exertion of the actions such as adjuvant effect is expected. Particularly, to exclude the transferred NKT cells by the allo recipient, NKT cells derived from an individual having different genotypes of all the above-mentioned 3 gene loci from those of the target individual of the immunocyte therapy are preferably used.

The NKT cells prepared from the peripheral blood, cord blood, spleen, lymph node and the like by the above-described method may be immediately contacted with nuclear reprogramming factors to induce NKT-iPS cells, or may also be preserved under freezing by a conventional method, thawed just before use, and cultured, and then contacted with nuclear reprogramming factors to induce NKT-iPS cells.

NKT cells are presumably functionally uniform immunocompetent cells characterized by rearrangement of either TCRα region to uniform Vα-Jα (Vα24-Jα18 in humans, Vα14-Jα18 in mice). In the NKT-iPS cell of the present invention, rearrangement to NKT-TCR is conserved.

Theoretically, the NKT-iPS cells of the present invention can be established by contacting somatic cells with nuclear reprogramming factors, even if the somatic cell is other than an NKT cell, by selecting cells derived from iPS cells obtained from said somatic cells, wherein the α-chain region of the T cell receptor gene is rearranged to uniform Vα-Jα in an NKT cell receptor-specific manner. However, since the emergency frequency of the NKT cell-specific receptor (Va24-Ja18) obtained by gene rearrangement is about 1/10$^6$, direct induction of an iPS cell from an NKT cell is the method for an efficient production of an NKT-iPS cell. Here, the NKT cell receptor is a T cell receptor that is expressed specifically in NKT cells, and that specifically recognizes α-galactosyl ceramide (α-GalCer) presented onto CD1d. The α-chain of the NKT cell receptor is normally rearranged to Vα24-Jα18 in humans, and to Vα14-Jα18 in mice. Therefore, rearrangement in an NKT cell receptor-specific manner means gene rearrangement in the α chain region such that the V-J combination in the α-chain region of the T cell receptor is Vα24-Jα18 in humans and Vα14-Jα18 in mice, and that the TCRα obtained is capable of constituting the NKT cell receptor. Such a somatic cell can be prepared by a method known per se. For example, such a somatic cell can be a somatic cell collected from an NKT cell clone animal prepared by transplanting the nucleus of an NKT cells to an enucleated cell (e.g., oocyte), and subjecting the cell to a specified operation. Generating a clone animal is described in, for example, WO2006/018998 and the like. In the case of human, a cloned human cannot be produced. However, it is theoretically possible to produce a human clone embryo by NKT cell nucleus transplantation and induce differentiation into any somatic cell in vitro.

In the present invention, "a nuclear reprogramming factor" may be composed of any substance such as a proteinous factor(s) or a nucleic acid that encodes the same (including forms incorporated in a vector) or a low molecular compound, as far as it is a substance (a group of substances) capable of inducing cells possessing pluripotency and self-renewal competence from a somatic cell such as an NKT cell. When the nuclear reprogramming factor is a proteinous factor or a nucleic acid that encodes the same, the following combinations, for example, are preferable (hereinafter, only the names for proteinous factors are shown).
(1) Oct3/4, Klf4, Sox2, c-Myc (Sox2 is replaceable with Sox1, Sox3, Sox15, Sox17 or Sox18; Klf4 is replaceable with Klf1, Klf2 or Klf5; c-Myc is replaceable with T58A (active mutant), N-Myc, or L-Myc)
(2) Oct3/4, Klf4, Sox2
(3) Oct3/4, Klf4, c-Myc
(4) Oct3/4, Sox2, Nanog, Lin28
(5) Oct3/4, Klf4, c-Myc, Sox2, Nanog, Lin28
(6) Oct3/4, Klf4, Sox2, bFGF
(7) Oct3/4, Klf4, Sox2, SCF
(8) Oct3/4, Klf4, c-Myc, Sox2, bFGF
(9) Oct3/4, Klf4, c-Myc, Sox2, SCF Since iPS-NKT cells obtained by induction of redifferentiation from NKT-iPS cells are used for an immunocyte therapy in the present invention, a combination of 3 factors of Oct3/4, Sox2 and Klf4 is more preferable among the above combinations. However, the present invention also aims at disappearance of the transferred NKT cells from the host body after the lapse of a given period, without allowing the engraftment of the cells. Therefore, as long as the NKT cells do not exert an adverse influence such as tumorigenesis and the like on the host during the period when the cells remain in the body, other reprogramming factors (e.g., c-Myc) that can be a risk factor in a normal organ transplantation may also be used. Therefore, 4 factors of Oct3/4, Klf4, Sox2 and c-Myc or N-Myc, and 5 factors including Lin28 or Nanog therein, are also preferable as nuclear reprogramming factors.

In the present invention, NKT-iPS cells can be acquired only with the above-described nuclear reprogramming factors in common use for reprogramming fibroblasts and the like, conventionally, thus obviating the use of other factors as reported in the case of T cells and B cells. This makes it possible to reduce the potential tumorigenesis in the cells and tissues differentiation-induced from an NKT-iPS cell.

Information on the mouse and human cDNA sequences of the aforementioned proteinous factors is available with reference to the NCBI accession numbers mentioned in WO 2007/069666 (in the publication, Nanog is described as ECAT4; mouse and human cDNA sequence information on Lin28 can be acquired by referring to the following NCBI accession numbers NM_145833 and NM_024674, and mouse and human cDNA sequence information on L-Myc can be acquired by referring to the following NCBI accession numbers NM_008506 and NM_001033081, respectively). Those skilled in the art are easily able to isolate these cDNAs. A proteinous factor for use as a nuclear reprogramming factor can be prepared by inserting the cDNA obtained into an appropriate expression vector, transferring the vector into a host cell, culturing the cell, and recovering the recombinant proteinous factor from the culture obtained. Meanwhile, when the nuclear reprogramming factor used is a nucleic acid that encodes a proteinous factor, the cDNA obtained is inserted into a viral, episomal or plasmid vector or the like to construct an expression vector, and the vector is subjected to the step of nuclear reprogramming.

Contact of a nuclear reprogramming factor with a somatic cell such as an NKT cell can be achieved using a method known per se for protein transfer into cells when the substance is a proteinous factor. Such methods include, for example, the method using a protein transfer reagent, the method using a protein transfer domain (PTD) or cell-penetrating peptide (CPP) fusion protein, the microinjection method and the like.

Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), and the like. The transfer can be achieved per the protocols attached to these reagents, a common procedure being as described below. A nuclear reprogramming factor is diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as *drosophila*-derived AntP, HIV-derived TAT, and HSV-derived VP22. A fusion protein expression vector incorporating a cDNA of a nuclear reprogramming factor and a PTD sequence is prepared to allow the recombinant expression of the fusion protein, and the fusion protein is recovered for use in for transfer. This transfer can be achieved as described above, except that no protein transfer reagent is added.

Examples of the CPP derived from PTD include polyarginine such as 11R (Cell Stem Cell, 4: 381-384 (2009)), 9R (Cell Stem Cell, 4: 472-476 (2009)) and the like.

Microinjection, a method of placing a protein solution in a glass needle having a tip diameter of about 1 μm, and injecting the solution into a cell, ensures the transfer of the protein into the cell.

A protein introduction operation can be performed one or more optional times (e.g., not less than once and not more than 10 times, or not less than once and not more than 5 times, etc.), and the introduction operation can be preferably repeated not less than twice (e.g., 3 or 4 times). An exemplary interval when repeating the introduction operation is 6-48 hr, preferably 12-24 hr.

When the efficiency of establishment of the iPS cell is important, the nuclear reprogramming factor is preferably used not as a protein but in the form of a nucleic acid encoding the same. The nucleic acid may be a DNA or an RNA, or a DNA/RNA chimera, and may be double-stranded or single-stranded. Preferably, the nucleic acid is a double-stranded DNA, particularly a cDNA.

A cDNA of a nuclear reprogramming factor is inserted into an appropriate expression vector comprising a promoter capable of functioning in a host somatic cell such as an NKT cell. Useful expression vectors include, for example, viral vectors such as retrovirus, lentivirus, adenovirus, adeno-associated virus, herpes virus and Hemagglutinating Virus of Japan, plasmids for the expression in animal cells (e.g., pA1-11, pXT1, pRc/CMV, pRc/RSV, pcDNAI/Neo) and the like.

A kind of vector used can be chosen as appropriate according to the intended use of the NKT-iPS cells obtained. For example, adenovirus vector, plasmid vector, adeno-associated virus vector, retrovirus vector, lentivirus vector, vector of Hemagglutinating Virus of Japan and the like can be used.

Examples of promoters used in expression vectors include the EF1α promoter, CAG promoter, SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF1α promoter, CAG promoter, MoMuLV LTR, the CMV promoter, the SRα promoter and the like.

The expression vector may contain as desired, in addition to a promoter, an enhancer, a polyA addition signal, a selection marker gene, a SV40 replication origin and the like. Examples of useful selection marker genes include the dihydrofolate reductase gene and the neomycin resistance gene.

An expression vector harboring a nucleic acid as a nuclear reprogramming factor can be transferred into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to the cell by a method suitable for the viral vector. Meanwhile, a plasmid vector can be transferred into a cell using the lipofection method, liposome method, electroporation method, calcium phosphate co-precipitation method, DEAE dextran method, microinjection method, gene gun method and the like.

When the nuclear reprogramming factor is a low-molecular compound, contact of the compound with somatic cells such as NKT cells can be achieved by dissolving the compound at an appropriate concentration in an aqueous or non-aqueous solvent, adding the compound solution to a medium suitable for cultivation of somatic cells such as NKT cells isolated from a human or mouse (e.g., a minimal essential medium (MEM), Dulbecco's modified Eagle medium (DMEM), RPMI1640 medium, 199 medium, and F12 medium containing cytokines such as IL-2, IL-7, SCF, and Flt3 ligands, and about 5 to 20% fetal bovine serum, and the like) so that the nuclear reprogramming factor concentration will fall in a range that is sufficient to cause nuclear reprogramming in somatic cells such as NKT cells and does not cause cytotoxicity, and culturing the cells for a given period. The nuclear reprogramming factor concentration varies depending on the kind of nuclear reprogramming factor used, and is chosen as appropriate over the range of about 0.1 nM to about 100 nM. Duration of contact is not particularly limited, as far as it is sufficient to achieve nuclear reprogramming of the cells; usually, the nuclear reprogramming factor may be allowed to be co-present in the medium until a positive colony emerges.

When generating the NKT-iPS cell of the present invention by contacting nuclear reprogramming factors with an NKT cell, the NKT cell to be contacted with the nuclear reprogramming factors may have been stimulated with an anti-CD3 antibody and an anti-CD28 antibody in the presence of IL-2 and IL-12. Stimulation of the NKT cell can be achieved by, for example, adding IL-2 and IL-12 to a medium suitable for culturing NKT cells as described above, and culturing the NKT cell on a culture dish with an anti-CD3 antibody and an anti-CD28 antibody bound to the surface thereof for a given time. The anti-CD3 antibody and the anti-CD28 antibody may be used in a mode dissolved in the medium, as far as they are able to stimulate the NKT cell. The concentration of each antibody as bound to the plate is 0.1-100 µg/ml; the concentration of each antibody as used in a mode dissolved in the medium is 0.1-100 µg/ml. The concentration of each of IL-2 and IL-12 added can be chosen as appropriate over the range of, for example, 0.1-100 ng/ml. The duration of cultivation is not particularly limited, as far as it is a sufficient time to ensure the proliferation of the NKT cell and stimulation with the anti-CD3 antibody and the anti-CD28 antibody; the duration is normally about 3 days to 1 month, for example, 1 week. The NKT cell stimulated through this step is contacted with the nuclear reprogramming factors.

In recent years, various substances that improve the efficiency of establishment of iPS cells, which has traditionally been low, have been proposed one after another. When brought into contact with somatic cell such as NKT cells together with the aforementioned nuclear reprogramming factors, these establishment efficiency improvers are expected to further raise the efficiency of establishment of NKT-iPS cells.

Examples of iPS cell establishment efficiency improvers include, but are not limited to, histone deacetylase (HDAC) inhibitors [for example, low-molecular inhibitors such as valproic acid (VPA) (Nat. Biotechnol., 26(7): 795-797 (2008)), trichostatin A, sodium butyrate, MC 1293, and M344; nucleic acid-based expression inhibiting agents such as siRNAs and shRNAs against HDAC (e.g., HDAC1 siRNA Smartpool° (registered trademark) (Millipore), HuSH 29mer shRNA Constructs against HDAC1 (OriGene) and the like); and the like], G9a histone methyltransferase inhibitors [e.g., low-molecular inhibitors such as BIX-01294 (Cell Stem Cell, 2: 525-528 (2008)); nucleic acid-based expression inhibitors such as siRNAs and shRNAs against G9a (e.g., G9a siRNA (human) (Santa Cruz Biotechnology) and the like; and the like], and the like. The nucleic acid-based expression inhibitors may be in the form of expression vectors harboring a DNA that encodes an siRNA or shRNA.

Contact of an iPS cell establishment efficiency improver with somatic cells such as NKT cells can be achieved as described above for each of three cases: (a) the improver is a proteinous factor, (b) the improver is a nucleic acid that encodes the proteinous factor, and (c) the improver is a low-molecular compound.

An iPS cell establishment efficiency improver may be brought into contact with somatic cells such as NKT cells simultaneously with a nuclear reprogramming factor, or either one may be contacted in advance, as far as the efficiency of establishment of NKT-iPS cells from somatic cells such as NKT cells is significantly improved, compared with the absence of the improver. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time after the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, when a nuclear reprogramming factor and an iPS cell establishment efficiency improver are both used in the form of a viral vector or plasmid vector, for example, both may be simultaneously transferred into the cell.

The somatic cells such as NKT cells separated from a human or mouse can also be pre-cultured using a medium known per se that is suitable for their cultivation (e.g., a minimal essential medium (MEM), Dulbecco's modified Eagle medium (DMEM), RPMI1640 medium, 199 medium, and F12 medium containing cytokines such as IL-2, IL-7, IL-15, SCF, and Flt3 ligands, and about 5 to about 20% fetal bovine serum, and the like).

When a transfection reagent such as a cationic liposome, for example, is used in contacting with nuclear reprogramming factors (and an iPS cell establishment efficiency improver), it is sometimes preferable that the medium be previously replaced with a serum-free medium to prevent a reduction in the transfer efficiency. After the nuclear reprogramming factors (and iPS cell establishment efficiency improver) are contacted, the cells can be cultured under conditions suitable for the cultivation of, for example, ES cells. In the case of human cells, it is preferable that the cultivation be carried out with the addition of basic fibroblast growth factor (bFGF) as a differentiation suppressor to an ordinary medium. Meanwhile, in the case of mouse cells, it is desirable that Leukemia Inhibitory Factor (LIF) be added in place of bFGF. Usually, the cells are cultured in the co-presence of fetal-mouse-derived fibroblasts (MEFs) treated with radiation or an antibiotic to terminate the cell division thereof, as feeder cells. Usually, STO cells and the like are commonly used as MEFs, but for inducing iPS cells, SNL cells [McMahon, A. P. & Bradley, A. Cell 62, 1073-1085 (1990)] and the like are commonly used.

A candidate colony of NKT-iPS cells can be selected by a method with drug resistance and reporter activity as indicators, and also by a method based on visual examination of morphology. As an example of the former, a colony positive for drug resistance and/or reporter activity is selected using a recombinant somatic cell such as a recombinant NKT cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Meanwhile, examples of the latter method based on visual examination of morphology include the method described by Takahashi et al. in Cell, 131, 861-872 (2007). Although the method using reporter cells is convenient and efficient, it is desirable, from the viewpoint of safety, that colonies be selected by visual examination, since the present invention aims to apply to human treatment; even by visual morphological examination, a candidate colony of NKT-iPS cells can be selected well efficiently.

Confirmation of the identity of the cells of the selected colony as NKT-iPS cells can be achieved by various testing methods known per se, for example, by measuring the expression of a group of genes including an ES cell-specific gene (e.g., Oct3/4, Sox2, Nanog, Cripto, Dax1, ERas, Fgf4, Esg1, Rex1, Zfp296 and the like) using RT-PCR or a DNA microarray and the like, and comparing the expression profile thereof with the gene expression profile in ES cells (e.g., fertilized egg-derived ES cells, ES cells derived from a clone embryo obtained by somatic cell nuclear transplantation from an NKT cell, and the like). To ensure higher accuracy, it is possible to induce differentiation and confirm formation of embrioid body or to transplant the selected cells to a mouse and confirm the formation of teratomas.

Confirmation of the fact that the NKT-iPS cells are derived from a somatic cell, such as an NKT cell, having the α chain region of the TCR gene (TCRα) is rearranged to uniform Vα-Jα in an NKT cell receptor-specific way can be achieved by examining the presence or absence of gene rearrangement to NKT-TCR by genomic PCR.

The detail of the production method of NKT-iPS cell is described in WO 2010/027094.

Pluripotent stem cells wherein the α-chain (TCRα) region of a TCR gene has been rearranged to uniform Vα-Jα in an NKT cell receptor-specific manner or wherein uniform Vα-Jα of an NKT cell receptor-specific manner has been inserted into a particular region on the genome to enable expression thereof, by inserting a gene into pluripotent stem cells to enable expression of the α chain and β chain of an NKT cell-specific TCR gene can be produced by, for example, according to the method described in JP-B-3030092, producing, from NKT cells, a microcell containing a chromosome fragment containing the α-chain (TCRα) region of the TCR gene rearranged to uniform Vα-Jα in an NKT cell receptor-specific manner, and transferring the aforementioned chromosome fragment to pluripotent stem cells by fusion with the microcell, or to a genome region capable of stable expression (human AAVS1 region and the like). The embodiment of NKT cells usable for the preparation of a chromosome fragment is as described above as the NKT cells usable for the production of NKT-iPS cells.

The pluripotent stem cell established from the nuclear transferred embryo of an NKT cell can be obtained by transplanting the nucleus of an NKT cell into an enucleated cell (e.g., oocyte), subjecting the cell to a predetermined operation to produce an NKT cell cloned animal, and cultivating an inner cell mass of an early embryo obtained by mating said cloned animals on a feeder cell to establish an ES cell. The production of a cloned animal is described in, for example, WO2006/018998 and the like. In the case of human, a cloned human cannot be produced. However, it is theoretically possible to produce an ES cell by producing a human clone embryo by NKT cell nuclear transplantation and cultivating the inner cell mass on a feeder cell in vitro.

A cell established from an NKT cell after completion of the rearrangement and having at least redifferentiation capacity into an NKT cell can be established by direct reprogramming. The direct reprogramming means establishment of a cell that can be more easily maintained and grown and the like than NKT cell, and can be redifferentiated into an NKT cell, by introducing a gene such as a transcription factor and the like into an NKT cell, adding a chemical substance that induces differentiation to a culture medium and the like. As an example of the direct reprogramming, there is a report on the obtainment of a neural stem cell by transferring Oct4, Sox2, Klf4 and c-Myc into a fibroblast and cultivating same under culture conditions suitable for the induction of a nerve cell (Kim et al., Proc Natl Acad Sci USA, 108, 7838-7843 (2011)). In addition, there is a report wherein NKT cell is subjected to a similar direct reprogramming and, when a cell obtained by the direct reprogramming and having at least redifferentiation capacity into an NKT cell has pluripotency, the cell is cultivated under conditions suitable for the induction of a T/NKT cell, whereby the NKT cell can also be obtained in a large amount (Watarai et al. J Clin Invest, 120, 2610-2618, 2010)).

Furthermore, examples of the cells having the α-chain (TCRα) region of a TCR gene rearranged to uniform Vα-Jα in an NKT cell receptor-specific manner, and having self renewal capacity and differentiation capacity into NKT cells include hematopoietic stem cells having the α-chain (TCRα) region of a TCR gene rearranged to uniform Vα-Jα in an NKT cell receptor-specific manner. The hematopoietic stem cells can be obtained by, for example, cultivating the above-mentioned NKT-iPS cells or NKT-PS cells under the conditions for differentiation into hematopoietic stem cells, or directly reprogramming NKT cells into hematopoietic stem cells. Examples of the conditions for differentiation of NKT-iPS cells or NKT-PS cells into hematopoietic stem cells include forced expression of Lhx2 (Kitajima et al., Blood, 117(14), 3748-3758 (2011)), differentiation induction in vivo (In vivo evaluation of putative hematopoietic stem cells derived from human pluripotent stem cells. Hexum M K, Tian X, Kaufman D S. Methods Mol. Biol. 2011; 767: 433-447.) and the like.

Among the thus-established cells having the α-chain region of a TCR gene rearranged to uniform Vα-Jα in an NKT cell receptor-specific manner (hereinafter to be abbreviated as NKT-derived cells), cells defined as pluripotent stem cells (hereinafter to be abbreviated as NKT-PS cells; e.g., NKT-iPS cells) can be differentiated into CD4/CD8-double positive NKT cells by cultivating in the presence of cytokines such as IL-7 and an Flt3 ligand, with stromal cells that express a Notch ligand as feeder cells, on the basis of a report on ES cells. Furthermore, the NKT-iPS cells can be differentiated into functional mature NKT cells in vitro using the method described below.

In a preferred embodiment, the NKT-derived cells (e.g., NKT-iPS cells) are differentiated into functional mature or immature NKT cells, which are activated by stimulation with an NKT cell receptor ligand such as α-GalCer and the like, ex vivo for utilization as, for example, a source of NKT cell immunotherapy agent.

For example, when NKT-PS cells (e.g., NKT-iPS cells) are used as NKT-derived cells, first, CD4/CD8-double positive NKT cells (hereinafter also referred to as "DP-NKT cells") can be generated by co-culturing NKT-PS cells (e.g., NKT-iPS cells) with stromal cells that express a Notch ligand. The stromal cells include, but are not limited to, OP9 cells, S17 cells and the like wherein a Notch ligand (e.g., Delta-like 1; hereinafter also referred to as "Dll-1") has been expressed forcedly. Examples of the medium for differentiation induction include, but are not limited to, a minimal essential medium (MEM), Dulbecco's modified Eagle medium (DMEM), RPMI1640 medium, 199 medium, and F12 medium containing cytokines such as interleukin-2 (IL-2), IL-7, IL-15, stem cell factor (SCF), and an Flt3 ligand (FL) (0.1-10 ng/mL each, preferably 1-5 ng/mL) and about 5 to 20% fetal bovine serum, and the like. NKT-iPS cells are seeded to obtain a cell density of, for example, about $1.0\times10^6$ to about $1.0\times10^7$ cells/mL, are cultured in a culture vessel known per se in an atmosphere of 5% $CO_2$/95% air, at about 30 to about 40° C., preferably at about 37° C., for about 1 to about 4 weeks, preferably for about 2 to about 3 weeks. Confirmation of their differentiation into DP-NKT cells can be achieved by, for example, analyzing the phenotype of a cell surface antigen by using an antibody against a cellular surface marker (e.g., each antibody against CD4 and CD8, antibody against CD3, TCRb and the like), a CD1d multimers (dimer, tetramer etc.) pulsed with α-galactosylceramide and a cell sorter. As required, it is also possible to examine the expression of still other various cell surface antigens, and compare the phenotype thereof with that of, for example, $CD4^+/CD8^+$ cells which are present in the thymus.

By co-culturing DP-NKT cells obtained as described above with stromal cells in the presence of several kinds of cytokines selected from among IL-2, IL-7, IL-15, IL-15 Ralpha and FL, NKT cells can be expanded in large amounts. Although the stromal cells used in this operation include, for example, the same as the above, such as OP9 cells and S17 cells, the cells may or may not be expressing a Notch ligand. Preferred media are the same as those shown above except for the combinations of cytokines. Specific combinations of cytokines include IL-7/FL, IL-2/IL-7/IL-15, IL-2/IL-7/IL-15/IL-15 Ralpha, IL-2/IL-7/FL, IL-2/IL-15/FL, IL-2/IL-15/IL-15 Ralpha/FL, IL-7/IL-15/FL, IL-7/IL-15/IL-15 Ralpha/FL, IL-2/IL-7/IL-15/FL, and IL-2/IL-7/IL-15/IL-15 Ralpha/FL, particularly preferably a combination of IL-7/FL, IL-2/IL-15/IL-15 Ralpha/FL and IL-2/IL-7/IL-15/IL-15 Ralpha/FL. The concentration of each cytokine can be chosen as appropriate over the range of 0.1-10 ng/mL, preferably 1-5 ng/mL. Still another cytokine (e.g., SCF and the like) may be added to the medium. While the cultivation may be adjusted as appropriate according to the animal species from which the cell is derived, it is performed, for example, under 5% $CO_2$/95% atmosphere, at about 30-about 40° C., preferably about 37° C., for about 3 days-about 6 weeks, preferably about 3 days-about 4 weeks, more preferably about 5 days-about 3 weeks. This cultivation allows the cell quantity to increase about 20 to about 30 times or more in 5 days.

The NKT cells obtained by the stimulation of the aforementioned combination of cytokines have an adjuvant effect since it produces IFN-γ by the stimulation with an NKT cell receptor ligand (e.g., α-galactosylceramide). To enhance the adjuvant effect, a preferable combination of cytokines is IL-7/FL or IL-7/IL-15/IL-15Ralpha/FL. The profile of the cytokine produced by the NKT cells induced by the combination of these cytokines is comparatively biased toward the Th1 type.

Meanwhile, by co-culturing DP-NKT cells obtained as described above with stromal cells that do not express a Notch ligand, NKT cells that are very similar to peripheral NKT cells can be generated. These NKT cells are characterized by NK marker (CD161 in human, NK1.1 in B6 mouse)-positive, and further by phenotypes such as $CD3\epsilon^+$, $Sca1^+$, $CD44^+$, $CD69^+$, $CD34^-$, and $Flt3^-$, with the expression of TCRα (Vα24 in human, Vα14 in mouse) decreased compared with DP-NKT cells, and showing expression levels equivalent to those in peripheral NKT cells. In other words, by switching the feeder cells from stromal cells that express a Notch ligand to stromal cells that do not express the ligand, in the midst of cultivation for differentiation induction from NKT-PS cells (e.g., NKT-iPS cells) to DP-NKT cells, the NKT-iPS cells can be differentiated and matured into NKT cells that are equivalent to peripheral NKT cells. Examples of stromal cells that do not express a Notch ligand include, but are not limited to, OP9 cells, S17 cells and the like. Although a medium for use for differentiation-induction from NKT-PS cells (e.g., NKT-iPS cells) to DP-NKT cells can be used likewise, it is preferable that the medium contain two or more cytokines selected from among IL-2, IL-7, IL-15 and FL, more preferably containing IL-15. The timing of switching the feeder cells from stromal cells that express a Notch ligand to stromal cells that do not express the ligand is not particularly limited, as far as NKT cells equivalent to peripheral NKT cells (e.g., NK1.1-positive cells) are finally obtained; for example, about 12 to about 20 days after, preferably about 14 to about 18 days after starting co-cultivation of NKT-PS cells (e.g., NKT-iPS cells) and stromal cells that express a Notch ligand, the feeder cells are switched to stromal cells that do not express the ligand. The duration of co-cultivation with the stromal cells that do not express the Notch ligand is also not particularly limited; for example, the duration is about 3 days to about 4 weeks, preferably about 5 days to about 3 weeks. By performing this cultivation using a medium containing three or more cytokines selected from among IL-2, IL-7, IL-15 and FL (preferably one thereof is IL-15), NKT cells that have differentiated and matured to the same extent as with peripheral NKT cells can be obtained in large amounts. In addition, an NKT cell that produces IFN-γ in a large amount can be produced by cultivating in the presence of several kinds of cytokines such as IL-7/FL and the like for 4 weeks or longer.

In an NKT-PS cell (e.g., NKT-iPS cell), the TCRα-chain region on the chromosome has been rearranged in an NKT cell-specific manner (Vα24-Jα18 in human, Vα14-Jα18 in mouse). Therefore, when the cells are induced to differentiate under the aforementioned conditions, almost all cells are differentiated into NKT cells and differentiation into conventional T cell does not occur substantially. In the present invention, therefore, when the administration subject is an individual allogenic to NKT cells, the possibility of contamination of allo conventional T cells can be avoided and the risk of developing a severe GVH reaction due to conventional T cells can be suppressed by using NKT cells induced from NKT-PS cells (e.g., NKT-iPS cells) as a sauce of the NKT cells. From the above-mentioned aspects, therefore, use of NKT cells induced from NKT-PS cells (e.g., NKT-iPS cells) is advantageous.

Since NKT cells derived from NKT-derived cells (e.g., NKT-iPS cells) obtained as mentioned above (hereinafter NKT cell derived from an NKT-derived cell is to be also referred to as "redifferentiated NKT cell", an NKT cell derived from an NKT-PS-derived cell as "PS-NKT cell", and NKT cell derived from an NKT-iPS cell as "iPS-NKT cell") are CD1d-restricted, redifferentiated NKT cells (e.g., PS-NKT cells, iPS-NKT cells) can be activated by contacting with dendritic cells (DCs) presenting an NKT cell receptor ligand such as α-GalCer and the like. While DC is preferably derived from a species identical to that of a derivation of redifferentiated cells (e.g., PS-NKT cells, iPS-NKT cells), DCs of different species may be used (e.g., mouse DCs are contacted with human redifferentiated NKT cells (e.g., human PS-NKT cells, human iPS-NKT cells)) as long as they can activate redifferentiated cells (e.g., PS-NKT cells, iPS-NKT cells). DCs are not particularly limited as long as they can activate redifferentiated NKT cells (e.g., PS-NKT cells, iPS-NKT cells) via a NKT cell receptor ligand, and may be myeloid lineage dendritic cells (DC1) or lymphoid dendritic cells (DC2), with preference given to DC1. The DCs may be generated by any method known per se, and can be separated from the bone marrow, peripheral non-lymphatic tissue, the T cell region of lymphatic tissue, afferent lymph, epidermis, dermis and the like; preferably, the DCs can be generated by separating monocytes, myelocytes and the like from bone marrow cells, peripheral blood and the like, for example, by density gradient centrifugation and the like, and culturing the cells in the presence of GM-CSF (and IL-4) for about 7 to about 10 days (Nature, 408, p. 740-745, 2000).

In the present invention, an NKT cell receptor ligand used for pulsing DC refers to a compound specifically recognized by a T cell receptor on the NKT cell when presented on a CD1d molecule, which can specifically activate the NKT cell. Examples of the NKT cell receptor ligand used in the present invention include α-glycosylceramide, isoglobotrihexosylceramide (Science, 306, p. 1786-1789, 2004), OCH (Nature 413:531, 2001) and the like. α-glycosylceramide is a sphingoglycolipid wherein saccharide such as galactose, glucose and the like is bonded to ceramide at the α configuration, and examples thereof include those disclosed in WO93/05055, WO94/02168, WO94/09020, WO94/24142, WO98/44928, Science, 278, p. 1626-1629, 1997 and the like. Of those, (2S,3S,4R)-1-O-(α-D-galactopyranosyl)-2-hexacosanoylamino-1,3,4-octadecanetriol (to be referred to as α-galactosylceramide or α-GalCer) is preferable.

In the present specification, the NKT cell receptor ligand is used as a meaning including even a salt thereof. As the salt of the NKT cell receptor ligand, a salt with a physiologically acceptable acid (e.g., inorganic acid, organic acid), base (e.g., alkali metal salt) and the like are used, and a physiologically acceptable acid addition salt is particularly preferable. Examples of such salt include a salt with an inorganic acid (e.g., hydrochloric acid, phosphoric acid, hydrobromic acid, sulfuric acid), a salt with an organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid), and the like.

In the present specification, moreover, the NKT cell receptor ligand is used as a meaning including even a solvate thereof (hydrate etc.).

Since the redifferentiated NKT cell of the present invention (e.g., PS-NKT cell, iPS-NKT cell) aims at administration to human, the NKT cell receptor ligand used to pulse DC is desirably of GMP grade.

Pulsation of DCs with an NKT cell receptor ligand can be performed by a technique in common use; for example, the pulsation can be performed by culturing the DCs in a serum-containing medium (e.g., 10% FCS-containing RPMI-1640 medium and the like) containing NKT cell receptor ligand at a concentration of about 0.1 to about 200 ng/mL for about 12 to about 48 hours. The pulsation with an NKT cell receptor ligand may be performed by adding α-GalCer to the medium in the process of culturing and maturing the immature DCs in the presence of GM-CSF (and IL-4). Alternatively, the pulsation may be performed by adding an NKT cell receptor ligand to the medium in the step of co-culturing the DCs matured as described below with redifferentiated NKT cells (e.g., PS-NKT cells, iPS-NKT cells).

Contact of the DCs and a redifferentiated NKT cells (e.g., PS-NKT cells, iPS-NKT cells) can be achieved by, for example, co-culturing both in the above-described medium in differentiation-induction from an NKT-derived cells (e.g., NKT-PS cells, NKT-iPS cells) to the redifferentiated NKT cells (e.g., PS-NKT cells, iPS-NKT cells) exhibiting phenotypes equivalent to those of peripheral NKT cells.

Here, the "activated NKT cell" means a redifferentiated NKT cell (e.g., PS-NKT cell, iPS-NKT cell) that at least produces a Th1 cytokine such as IFN-γ in response to α-GalCer-presenting DC. The cell may further possess productivity for a Th2 cytokine such as IL-4, and may possess a proliferation potential. For redifferentiated NKT cells (e.g., PS-NKT cells, iPS-NKT cells) to acquire a proliferation potential and Th2 cytokine productivity as well upon stimulation with α-GalCer-presenting DCs, the cells need to continue to be co-cultured with stromal cells that express a Notch ligand in the process of differentiation induction from NKT-derived cells (e.g., NKT-PS cells, NKT-iPS cells) to redifferentiated NKT cells (e.g., PS-NKT cells, iPS-NKT cells); in this case, the IFN-γ productivity also increases compared with redifferentiated NKT cells (e.g., PS-NKT cells, iPS-NKT cells) obtained by switching to stromal cells that do not express a Notch ligand. By choosing the combination IL-7/FL or IL-15/IL-15R alpha/IL-7/FL as cytokines in the culturing step for mass expanding redifferentiated NKT cells (e.g., PS-NKT cells, iPS-NKT cells) from DP- NKT cells, the Th1/Th2 cytokine production balance in activated NKT cell, in particular, exhibits Th1 dominance.

The present invention provides an agent for an immunocyte therapy containing redifferentiated NKT cells (e.g., PS-NKT cells, iPS-NKT cells) obtained as mentioned above. The redifferentiated NKT cell (e.g., PS-NKT cell, iPS-NKT cell) is preferably an activated NKT cell. The redifferentiated NKT cell (e.g., PS-NKT cell, iPS-NKT cell) provided by the present invention has proliferative capacity and Th1 dominant cytokine production capacity and an adjuvant effect, like an endogenous NKT cell. Therefore, for example, it is useful for the prophylaxis or treatment of various diseases such as cancer, infections, allergic diseases, autoimmune diseases and the like. As the cancer, all kinds of primary cancers can be mentioned, and all conditions of cancers, including early cancers and advanced cancers with a metastatic/infiltrating potential, can be mentioned. Specific examples of cancer include, but are not limited to, lung cancer (small and/or non-small cell), brain tumor, gastric cancer, esophagus cancer, liver cancer, pancreatic cancer, kidney cancer, urinary bladder cancer, breast cancer, ovarian cancer, uterine cancer, testis cancer, skin cancer, osteosarcoma, colonrectal cancer, chronic lymphocytic leukemia, acute lymphocytic leukemia, acute non-lymphocytic leukemia, chronic myeloid leukemia, ACTH-producing tumor, adrenal cortex cancer, skin T-cell lymphoma, endometrial carcinoma, Ewing's sarcoma, gall bladder cancer, cervical cancer, Hodgkin lymphoma, Kaposi's sarcoma, melanoma, mesothelioma, multiple myeloma, neuroblastoma, non-Hodgkin lymphoma, ovary (germ cell) cancer, penile cancer, prostate cancer, retinoblastoma, soft tissue sarcoma, flat epithelial cell cancer, thyroid cancer, trophoblastic neoplasm, vaginal cancer, vulvar cancer, Wilms' tumor and the like. Examples of autoimmune disease include, but are not limited to, multiple sclerosis, rheumatoid arthritis, psoriasis, Crohn's disease, vitiligo vulgaris, Behcet's disease, collagen disease, Type I diabetes mellitus, uveitis, Sjogren's syndrome, autoimmune myocarditis, autoimmune hepatic diseases, autoimmune gastritis, pemphigus, Guillain-Barre syndrome, HTLV-1-associated myelopathy and the like. Examples of allergic disease include, but are not limited to, asthma, allergic rhinitis, allergic conjunctivitis, atopic dermatitis, allergic stomach enteritis and the like. Examples of infections include, but are not limited to, virus infections with CMV (e.g., HCMV, MCMV and the like), simple herpes virus, EB virus, human immunodeficiency virus, influenza virus, SARS virus and the like.

The administration subject of the agent for an immunocyte therapy of the present invention is an allogenic individual wherein at least one of the MHC gene loci has a genotype different from that of redifferentiated NKT cells (e.g., PS-NKT cells, iPS-NKT cells) as an active ingredient thereof. This is an innovative "medicament" having a completely different treatment concept from the immunocyte therapy agent previously reported by the present inventors wherein the administration subject is an individual from whom the NKT cells are derived or an allogenic individual having the identical MHC type (i.e., genotype of major gene locus of MHC is substantially completely identical). To be specific, while the latter presupposes that the transferred NKT cells are engrafted into the body of the host and continue to function, since at least a part of the MHC gene locus of the transferred NKT cells does not match in the immunocyte therapy agent of the present invention, the transferred NKT cells are recognized by the immune system of the recipient and finally excluded without engraftment. However, since the adjuvant effect of the NKT cells is achieved in a short period, they can activate immune cells (e.g., CD8 T cells, NK cell) other than the NKT cells. Therefore, in the immunocyte therapy agent of the present invention, the NKT cells play the same role as "general pharmaceutical products" that are rapidly excluded from the body after exerting efficacy for a necessary period.

The MHC gene locus is as defined above, and 3 gene loci of HLA-A, HLA-B and HLA-C can be mentioned for human MHC (HLA). Similarly, H-2K, H-2D and H-2L gene loci of class I region can be mentioned for mouse as the major gene loci in the present invention.

In one embodiment, an allogenic individual having a different genotype of at least 1 locus (preferably 2 loci, more preferably 3 loci), among the above-mentioned 3 gene loci, from that of the NKT cells to be transferred is the target individual of the immunocyte therapy. In this embodiment, since the administered NKT cells are excluded by an immunoreaction against allo cells of the recipient due to the mismatch of MHC gene locus, exclusion of the cells after effective exertion of the actions of adjuvant effect and the like is expected. Particularly, to exclude the transferred NKT cells by the allo recipient, NKT cells derived from an individual showing different genotypes of all the above-mentioned 3 gene loci from those of the target individual of the immunocyte therapy is preferably used.

The redifferentiated NKT cells (e.g., PS-NKT cell, iPS-NKT cell) are produced as an oral/parenteral preparation, preferably as an injection, suspension, or drip infusion, by being blended with a pharmaceutically acceptable carrier by a conventional means or otherwise. Pharmaceutically acceptable carriers that can be contained in the parenteral preparation include, for example, aqueous solutions for injection, such as physiological saline and isotonic solutions containing glucose or another auxiliary drug (e.g., D-sorbitol, D-mannitol, sodium chloride and the like). The agent of the present invention may be formulated with, for example, a buffering agent (e.g., phosphate buffer solution, sodium acetate buffer solution), a soothing agent (e.g., benzalkonium chloride, procaine hydrochloride and the like), a stabilizer (e.g., human serum albumin, polyethylene glycol and the like), a preservative, an antioxidant and the like.

When the agent of the present invention is prepared as an aqueous suspension, the redifferentiated NKT cells (e.g., PS-NKT cells, iPS-NKT cells) are suspended in the above-described aqueous liquid to, for example, about $1.0 \times 10^6$ to $1.0 \times 10^7$ cells/ml.

Since the preparation thus obtained is stable and of low toxicity, it can be safely administered to mammals such as humans. Although the method of administration is not particularly limited, the preparation can be administered orally or parenterally, preferably by injection or drip infusion; examples include intravenous administration, subcutaneous administration, intradermal administration, intramuscular administration, intraperitoneal administration, direct administration to the affected site and the like. The dose of the immunocyte therapy agent varies depending on the recipient of administration, target organ, symptoms, method of administration and the like; in the case of parenteral administration, for example, it is normally convenient to administer about $1.0 \times 10^7$ to about $1.0 \times 10^9$ cells, based on the numbers of NKT cells per dose, at intervals of about 1 to 2 weeks, about 4 to about 8 times, for an adult patient (assuming a body weight of 60 kg).

To promote activation of the redifferentiated NKT cells (e.g., PS-NKT cells, iPS-NKT cells) to be transferred in the body, the immunocyte therapy agent of the present invention may use a combination of the redifferentiated NKT cells (e.g., PS-NKT cells, iPS-NKT cells) as the active ingredient thereof and an NKT cell receptor ligand.

As the NKT cell receptor ligand to be used in combination with the redifferentiated NKT cells (e.g., PS-NKT cells, iPS-NKT cells), those mentioned above for the production of the activated NKT cells can be used in the same manner, with preference given to α-GalCer. When the administration subject is a human, an NKT cell receptor ligand of GMP grade is used. In patients suffering from a disease that requires NKT cell cytotherapy, such as a cancer, who sometimes have a decreased number or lacked function of endogenous DCs, DCs pulse with an NKT cell receptor ligand may be used instead of the NKT cell receptor ligand to promote in vivo activation of the redifferentiated NKT cells (e.g., PS-NKT cells, iPS-NKT cells). In this case, the source of DCs collected is preferably the patient who is the recipient of administration (that is, autologous transplantation); however, this is not to be construed as limiting, as far as the source is allogenic individual of the same species that is estimated to be compatible to the patient.

The NKT cell receptor ligand is normally produced, along with a pharmaceutically acceptable carrier, as a parenteral preparation such as an injection, suspension, or drip infusion. Pharmaceutically acceptable carriers that can be contained in the parenteral preparation include, for example, aqueous solutions for injection, such as physiological saline and isotonic solutions containing glucose or another auxiliary drug (e.g., D-sorbitol, D-mannitol, sodium chloride and the like). The agent of the present invention may be formulated with, for example, a buffering agent (e.g., phosphate buffer solution, sodium acetate buffer solution), a soothing agent (e.g., benzalkonium chloride, procaine hydrochloride and the like), a stabilizer (e.g., human serum albumin, polyethylene glycol and the like), a preservative, an antioxidant and the like. When the NKT cell receptor ligand is prepared as an aqueous preparation, the NKT cell receptor ligand is dissolved in an appropriate organic solvent (e.g., DMSO and the like) and dissolved in the above-described aqueous liquid to obtain a concentration of, for example, about 100 μg to about 1 mg/mL.

Meanwhile, when using NKT cell receptor ligand-pulsed DCs in place of NKT cells receptor ligand, NKT cell receptor ligand-pulsed DCs prepared by the technique described above with respect to generating activated NKT cells may be suspended in the above-described aqueous liquid to, for example, about $1.0 \times 10^6$ to about $1.0 \times 10^7$ cells/mL.

The NKT cell receptor ligand prepared as a preparation as described above can be administered orally or parenterally, preferably by injection or drip infusion; examples include intravenous administration, subcutaneous administration, intradermal administration, intramuscular administration, intraperitoneal administration, direct administration to the affected site and the like. The dose of the NKT cell receptor ligand varies depending on the recipient of administration, target organ, symptoms, method of administration and the like; normally, in the case of parenteral administration, for example, the dose is normally about 0.6 to about 6.0 mg, based on a single dose, for an adult patient (assuming a body weight of 60 kg). Meanwhile, when using NKT cell receptor ligand-pulsed DC in place of NKT cells receptor ligand, the dose thereof is normally about $1.0 \times 10^7$ to about $1.0 \times 10^9$ cells per dose. These amounts can be administered according to the administration protocol for the iPS-NKT cell-containing preparation.

A redifferentiated NKT cells (e.g., PS-NKT cells, iPS-NKT cells)-containing preparation and an NKT cell receptor ligand-containing preparation may be administered separately or simultaneously by blending when in use, and may be administered sequentially in the order of the redifferentiated NKT cells (e.g., PS-NKT cells, iPS-NKT cells)-containing preparation, and then the NKT cell receptor ligand-containing preparation.

The present invention also provides a bank of human NKT-derived cells (e.g., NKT-PS cells, NKT-iPS cells) or NKT cells derived from said NKT-derived cells (redifferentiated NKT cells) (e.g., PS-derived NKT cells (PS-NKT cells), iPS-derived NKT cells (iPS-NKT cells)), which enables provision of an immunocyte therapy using the above-mentioned human redifferentiated NKT cell (e.g., human PS-NKT cell, human iPS-NKT cell), under more rapid, universal conditions superior in quality control. There exist many concepts of human iPS cell banking aiming at transplantation therapy. However, the human NKT cell-derived cell (e.g., PS cell, iPS cell) bank or the NKT-derived cell (e.g., PS cell, iPS cell)-derived NKT cell bank of the present invention is characterized by easy induction of differentiation of a functional NKT cell, since it is constituted solely by NKT cell-derived cells (e.g., PS cells, iPS cells) (or the NKT-derived cells (e.g., PS cells, iPS cells)-derived NKT cells) that already underwent gene rearrangement. Conventionally-proposed human iPS cell bank aims to prepare a repertoire of human iPS cells that enables provision of cells or organs that can be engrafted into the body of any patients, so that the bank can be applicable to any patients, namely, a repertoire of human iPS cells having genotypes that match with all of the major gene loci of HLA (HLA-A, HLA-B, HLA-C and HLA-DRB1). The present invention is markedly different therefrom in that it aims to collect NKT-derived cells (e.g., NKT-PS cells, NKT-iPS cells) or redifferentiated NKT cells (e.g., PS-NKT cells, iPS-NKT cells) that enable provision, to any patients, of human NKT cells that stay in the body of a patient for a certain period to exert efficacy, and then are excluded from the body of the patient.

In the immunocyte therapy of the present invention, an allogenic individual wherein at least one of the MHC gene loci has a genotype mismatched to that of the NKT cell is the administration subject. Since it is rare that all genotypes of MHC gene loci match completely between NKT cell and the patient, theoretically, one kind of NKT cell-derived cell (e.g., NKT-PS cell, NKT-iPS cell) with confirmed safety and differentiation capacity into an NKT cell can cover almost all patients. In the present invention, when at least one of the HLA gene loci (e.g., at least one gene locus selected from the group consisting of HLA-A, HLA-B and HLA-C) does not match, the cell can be used for transplantation. Therefore, banking of human NKT-derived cells (e.g., human NKT-PS cells, human NKT-iPS cells) that meets the object of the present invention must be achievable comparatively easily to the extent that can cover the most part of the patient population.

In one embodiment, the present invention provides a bank of human NKT cell-derived cells (e.g., NKT-PS cells, NKT-iPS cells) or NKT cells derived from said NKT-derived cells (e.g., PS-NKT cells, iPS-NKT cells), which has a genotype repertoire wherein the total frequency of the genotype of a particular HLA gene locus (e.g., at least one (preferably 2, more preferably 3) gene locus selected from the group consisting of HLA-A, HLA-B and HLA-C) in a certain population covers not less than 50% (e.g., not less than 60%, preferably not less than 70%, more preferably not less than 80%, still more preferably not less than 90%) of the whole population. Using the human NKT cell-derived cell bank (or bank of NKT cell derived from said NKT-derived cell) of the embodiment, human NKT cell-derived cells (e.g., NKT-PS cells, NKT-iPS cells) and NKT cells derived from said NKT-derived cell (e.g., PS-NKT cells, iPS-NKT cells), wherein the genotype of a particular HLA gene locus (e.g., at least one (preferably 2, more preferably 3) gene locus selected from the group consisting of HLA-A, HLA-B and HLA-C gene loci) does not match with that of a particular patient can be smoothly supplied for almost all patients contained in the population, by determining, with regard to the particular patient, only the genotype of a particular HLA gene locus (hereinafter to be referred to as "target HLA") where the cell bank covers not less than 50% (e.g., not less than 60%, preferably not less than 70%, more preferably not less than 80%, still more preferably not less than 90%) of the particular HLA gene locus in the whole population, and selecting human NKT cell-derived iPS cells having said HLA with a genotype different from that of the patient from the bank. Alternatively, by providing repertoires of such variety in the bank, human NKT cell-derived cells (e.g., NKT-PS cells, NKT-iPS cells) or NKT cells derived from said NKT-derived cells (e.g., PS-NKT cells, iPS-NKT cells) having the genotypes of plural gene loci (e.g., all gene loci of HLA-A, HLA-B and HLA-C) mismatched to those of the administration subject can be supplied smoothly.

The target HLA is preferably HLA-A, HLA-B or HLA-C, particularly preferably HLA-A, since HLA-A gene locus contains less kinds of allele and has a serum type (2-digit level) that covers 92% of the Japanese people with 6 kinds of A24, A2, A11, A26, A31 and A33, and selection of the genotype of the HLA-A gene locus facilitates obtainment of an HLA genotype that meets the object of the present invention.

Here, the "certain population" may be, for example, the national unit such as the Japanese people as a whole, the American people as a whole and the like; ethnic unit; racial unit such as the white race as a whole, the yellow race as a whole, the black race as a whole and the like; or the mankind as a whole.

The human NKT-derived cell bank or human redifferentiated NKT cell bank of the present invention can be constructed by the following steps (1)-(4):
(1) determining the genotype of a particular HLA gene locus (e.g., at least one HLA gene locus selected from the group consisting of HLA-A, HLA-B and HLA-C) of a donor registrant;
(2) collecting NKT cells from the donor registrant;
(3) establishing human NKT-derived cells from the NKT cells, and establishing, where necessary, human redifferentiated NKT cells from said established human NKT-derived cells; and
(4) determining the differentiation potency of the established human NKT-derived cells into. NKT cells, and tumorigenicity after the differentiation, and successively banking cells which satisfy the criteria.

The human NKT-iPS cell bank or human iPS-NKT cell bank of the present invention can be constructed by the following steps (1)-(4):
(1) determining the genotype of a particular HLA gene locus (e.g., at least one HLA gene locus selected from the group consisting of HLA-A, HLA-B and HLA-C) of a donor registrant;
(2) collecting NKT cells from the donor registrant;
(3) establishing human iPS cells by contacting the NKT cells with a nuclear reprogramming factor, and establishing, where necessary, human NKT cells from the established human iPS cells; and
(4) determining the differentiation potency of the established human iPS cells into NKT cells, and tumorigenicity after the differentiation, and successively banking cells which satisfies the criteria.

When the bank of the human NKT cell-derived cells (e.g., NKT-PS cells, NKT-iPS cells) or NKT cells derived from said NKT-derived cells (e.g., PS-NKT cells, iPS-NKT cells) in the above-mentioned particular embodiment is to be constructed, the operation is repeated until the constructed bank of the human NKT-derived cells (e.g., NKT-PS cells, NKT-iPS cells) or NKT cells derived from said NKT-derived cells (e.g., iPS-NKT cells) shows a genotype repertoire of a particular HLA gene locus (e.g., at least one (preferably 2, more preferably 3) gene locus selected from the group consisting of HLA-A, HLA-B and HLA-C) of the banked human NKT cell-derived cells (e.g., NKT-PS cells, NKT-iPS cells) or NKT cells derived from said NKT-derived cell (e.g., PS-NKT cells, iPS-NKT cells), which covers not less than 50% (e.g., not less than 60%, preferably not less than 70%, more preferably not less than 80%, still more preferably not less than 90%) in the total of the frequency in the whole population.

The donor registration is expected to receive entry with ease by, for example, obtaining a written informed consent in advance as to the peripheral blood collected by general blood donation (or lymphocyte collected by component blood donation) or cord blood collected at the time of birth, and the like. As for HLA typing, the genotype of HLA-A, HLA-B and HLA-C may be determined by the SBT method generally used for donor search for bone marrow transplantation, or high frequency allele can be predicted by the fluorescence beads method. Human NKT cells can also be easily collected by requesting a person who has already completed HLA typing through donor registration for organ transplantation or bone marrow transplantation to provide the peripheral blood or cord blood.

The aforementioned method of producing NKT-derived cells (e.g., NKT-PS cells, NKT-iPS cells) can be directly applied to the aforementioned step (3).

Moreover, the differentiation capacity of the human NKT-derived cells (e.g., NKT-PS cells, NKT-iPS cells) established in the aforementioned step (4) into NKT cells can be determined by applying the aforementioned production method of the redifferentiated NKT cells (e.g., PS-NKT cells, iPS-NKT cells) and evaluating whether differentiation induction into NKT cells can be achieved. On the other hand, tumorigenicity after differentiation can be determined by methods such as karyotype analysis (chromosome specimen is stained with giemsa and chromosome number and chromosome structural abnormality are analyzed under a microscope), evaluation of cell with a high passage number (absence of change in the cell property is confirmed), soft agar medium method (utilizing that a cell having tumorigenicity does not require anchorage for cell adhesion for the growth), transplantation to immunodeficient animal (intramuscular or subcutaneous injection of human NKT-derived cells (e.g., NKT-PS cells, NKT-iPS cells) to nude mouse and the like, followed by determination of the presence or absence of tumor formation) and the like.

As a result of the above-mentioned determination, human NKT cell-derived cells (e.g., NKT-PS cells, NKT-iPS cells) or NKT cells derived from the NKT-derived cells (e.g., PS-NKT cells, iPS-NKT cells) determined to have differentiation capacity into an NKT cell, and substantially no tumorigenicity after differentiation are banked. The banked cells are cryopreserved in a dispensed state according to a conventionally-used method, and human redifferentiated NKT cells (e.g., PS-NKT cells, iPS-NKT cells) can be prepared when in use by thawing a part of the stock, expanding same to a sufficient amount as necessary with a suitable medium (e.g., medium for human ES cell culture and the like), and thereafter following the above-mentioned differentiation induction method from NKT-derived cells (e.g., NKT-PS cells, NKT-iPS cells) into NKT cells.

Expansion and differentiation induction into NKT cells of human NKT-derived cells (e.g., NKT-PS cells, NKT-iPS cells) can also be performed, after furnishing of cells of interest from the cell bank, by a medical institution to be provided with the cells. However, it is not realistic since strict regulatory requirements for quality management of the cell itself and medium (infection with mycoplasma and the like, test of remaining undifferentiated cell and the like), management of apparatus and the like need to be met. Therefore, it is desirable to uniformly perform expansion of an NKT-derived cell (e.g., NKT-PS cell, NKT-iPS cell) and differentiation induction into redifferentiated NKT cells (e.g., PS-NKT cells, iPS-NKT cells) according to the standardized protocol in the cell bank facility, and supply the medical institution to be provided with the cells with the redifferentiated NKT cells (e.g., PS-NKT cells, iPS-NKT cells).

A medical institution desirous of the supply of human redifferentiated NKT cells (e.g., PS-NKT cells, iPS-NKT cells) performs HLA typing of the target patient, and notifies the cell bank. In this case, the medical institution confirms that the genotype of at least one HLA gene locus (e.g., at least one (preferably 2, more preferably 3) gene locus selected from the group consisting of HLA-A, HLA-B and HLA-C) of the banked NKT cell list does not match, and use the cell for the treatment purposes. The medical institution only needs to inform of the genotype of the HLA gene locus of the patient, and the cell bank confirms, based on the data accumulated up to then, that the genotype is different in at least one (e.g., at least one (preferably 2, more preferably 3) gene locus selected from the group consisting of HLA-A, HLA-B and HLA-C) gene locus of the patient's HLA gene locus, and supplies NKT cell-derived cells (e.g., NKT-PS cells, NKT-iPS cells) or NKT cells derived from said cell (e.g., PS-NKT cells, iPS-NKT cells). For this purpose, it is desirable that each medical institution provided with cells disclose, to the cell bank, information of clinical data relating to the administration method, treatment protocol, treatment effect, side effects and the like of the redifferentiated NKT cells (e.g., PS-NKT cells, iPS-NKT cells), and the cell bank not only work on the optimization of preservation method of the cell, and the conditions for expansion, differentiation induction and purification of the cell, but also construct a system to share and reduce the database of the clinical information collected from each medical institution.

All references cited in the present specification, including publication, patent document and the like, are hereby incorporated individually and specifically by reference, to the extent that the entireties thereof have been specifically disclosed herein.

The present invention is hereinafter described in more detail by means of the following Examples, to which, however, the invention is not limited in any way.

EXAMPLES

Example 1

(1) Establishment of iPS Cells from Mouse Splenocyte-Derived NKT Cells

NKT cells were prepared from splenocytes of a C57BL/6 mouse having the T cell receptor α-chain (TCRα) region already rearranged to TCR used in NKT cells (NKT-TCR). Since NKT cells are characterized by recognizing glycolipid antigens presented to the MHC class I-like molecule CD1d, the cells were concentrated by positively selecting cells reactive to an anti-mouse IgG1 antibody prepared by APC-labeling a solubilized CD1d-mouse IgG1 recombinant having the glycolipid antigen α-GalCer inserted therein (produced by BD Bioscience Company), using a MACS method which utilizes anti-APC magnetic beads (produced by Miltenyi Biotech Company). This operation rendered the NKT cells as defined as α-GalCer loaded CD1d dimer-positive/TCRβ-positive cells to have a purity of 90% or more. The concentrated NKT cells were cultured in the presence of IL-2 (10 ng/ml) at a cell density of $10^6$ cells/ml, using an RPMI medium containing 10% FCS for 24 hours, after which the cells were infected with a retrovirus containing four mouse-derived factors (nucleic acids that encode Oct3/4, Sox2, Klf4, and c-Myc) ($10^6$ pfu/ml) according to the method described in Cell, 126: 663-676 (2006) for 24 hours. Three to seven days after the viral infection, the cells were recovered, re-seeded onto mouse embryonic fibroblasts (MEF), and co-cultured in the presence of LIF using an ES cell culture medium. The emerging colonies were morphologically evaluated, and colonies assuming an ES-like morphology were picked up and further cultured in the presence of LIF on MEF, whereby 4 clones of NKT cell-derived iPS cells (NKT-iPS cells) were established (clone code names: 2a, 5b, 5d, 5g).

(2) Characterization of NKT-iPS Cells

To demonstrate that the four clones of NKT-iPS cells established in the above-mentioned (1) were derived from NKT cells, whether rearrangement to NKT-TCR had occurred was determined by genomic PCR. In the cells having NKT-TCR, either TCRα region had already been rearranged to Vα14-Jα18 (FIG. 1); hence, the presence or absence of rearrangement was checked by performing a PCR using the primers shown below with the genome of each NKT-iPS clone as the template.

```
SEQ ID NO: 1:  Primer 1:
               5'-gacccaagtggagcagagtcct-3'

SEQ ID NO: 2:  Primer 2:
               5'-tcacctatgtctcctggaagcctc-3'

SEQ ID NO: 3:  Primer 3:
               5'-cagctccaaaatgcagcctccctaa-3'
```

[In case where rearrangement to Vα14-Jα18 has not occurred (wild), a 349 bp band is amplified by a PCR using primer 1 and primer 2; meanwhile, in case where rearrangement to Vα14-Jα18 has occurred (NKT-TCR), a 317 bp band is amplified by a PCR using primer 1 and primer 3.]

Figure 2:
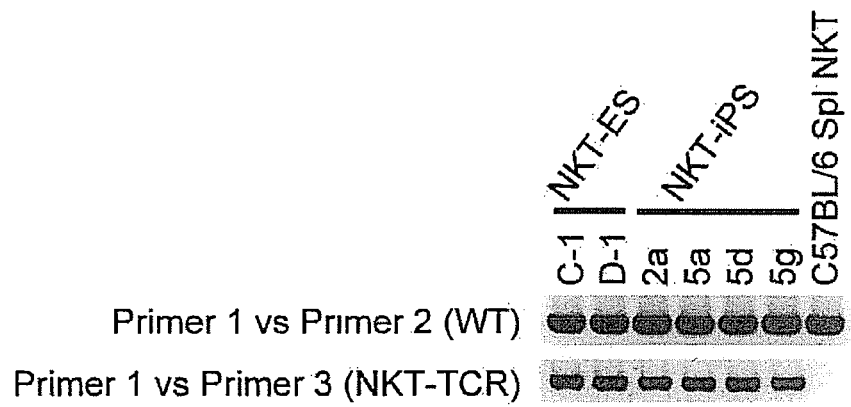
FIG. 2 is a drawing showing Vα-Jα rearrangement in NKT-iPS cells.

As a result, all of the four established clones were found to have either genome rearranged to NKT-TCR (FIG. 2), confirming that the established iPS cells were of NKT cell derivation.

(3) Genetic Expression Analysis of NKT-iPS Cells

To determine whether the NKT-iPS cells identified in the above-mentioned (2) had been reprogrammed to iPS-like cells, gene expression profiling was performed. Total RNA was prepared from each of NKT-iPS cells, NKT cell nuclear transplantation embryo-derived ES cells (NKT-ES cells), and peripheral NKT cells by the phenol-chloroform method, the expression of a series of gene groups whose expression in ES cells is known was analyzed by the one step RT-PCR method (produced by Invitrogen Company). The genes analyzed and the sequences of the primers used are shown below.

```
Endogenous Oct3/4:
                                       (SEQ ID NO: 4)
5'-tctttccaccaggcccccggctc-3'

(SEQ ID NO: 5)
5'-tgcgggcggacatggggagatcc-3'

Endogenous Sox2:
                                       (SEQ ID NO: 6)
5'-tagagctagactccgggcgatga-3'

(SEQ ID NO: 7)
5'-ttgccttaaacaagaccacgaaa-3'

Endogenous Klf4:
                                       (SEQ ID NO: 8)
5'-gcgaactcacacaggcgagaaacc-3'

(SEQ ID NO: 9)
5'-tcgcttcctcttcctccgacaca-3'

Endogenous c-Myc:
                                      (SEQ ID NO: 10)
5'-tgacctaactcgaggaggagctggaatc-3'

(SEQ ID NO: 11)
5'-aagtttgaggcagttaaaattatggctgaagc-3'

Ecat1:
                                      (SEQ ID NO: 12)
5'-tgtggggccctgaaaggcgagctgagat-3'

(SEQ ID NO: 13)
5'-atgggccgccatacgacgacgctcaact-3'

Nanog:
                                      (SEQ ID NO: 14)
5'-caggtgtttgagggtagctc-3'

(SEQ ID NO: 15)
5'-cggttcatcatggtacagtc-3'

Gdf3:
                                      (SEQ ID NO: 16)
5'-gttccaacctgtgcctcgcgtctt-3'

(SEQ ID NO: 17)
5'-agcgaggcatggagagagcggagcag-3'

Rex1:
                                      (SEQ ID NO: 18)
5'-acgagtggcagtttcttcttggga-3'

(SEQ ID NO: 19)
5'-tatgactcacttccagggggcact-3'

Zfp296:
                                      (SEQ ID NO: 20)
5'-ccattagggccatcatcgctttc-3'

(SEQ ID NO: 21)
5'-cactgctcactggaggggcttgc-3'

HPRT:
                                      (SEQ ID NO: 22)
5'-ctgtgtgctcaagggggct-3'

(SEQ ID NO: 23)
5'-ggactcctcgtatttgcagattcaacttg-3'
```

Figure 3:
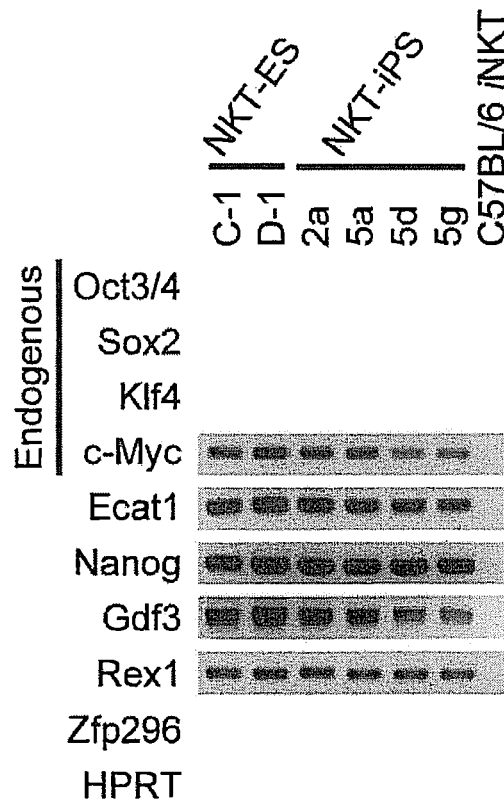
FIG. 3 is a drawing showing the expression of ES cell-specific genes in NKT-iPS cells.

As a result, the expression of all of the genes analyzed was confirmed in NKT-iPS cells and NKT-ES cells, but no expression was confirmed in peripheral NKT cells (FIG. 3).

This result suggests that the established NKT-iPS cells may possess an iPS cell-like function.

Figure 4:
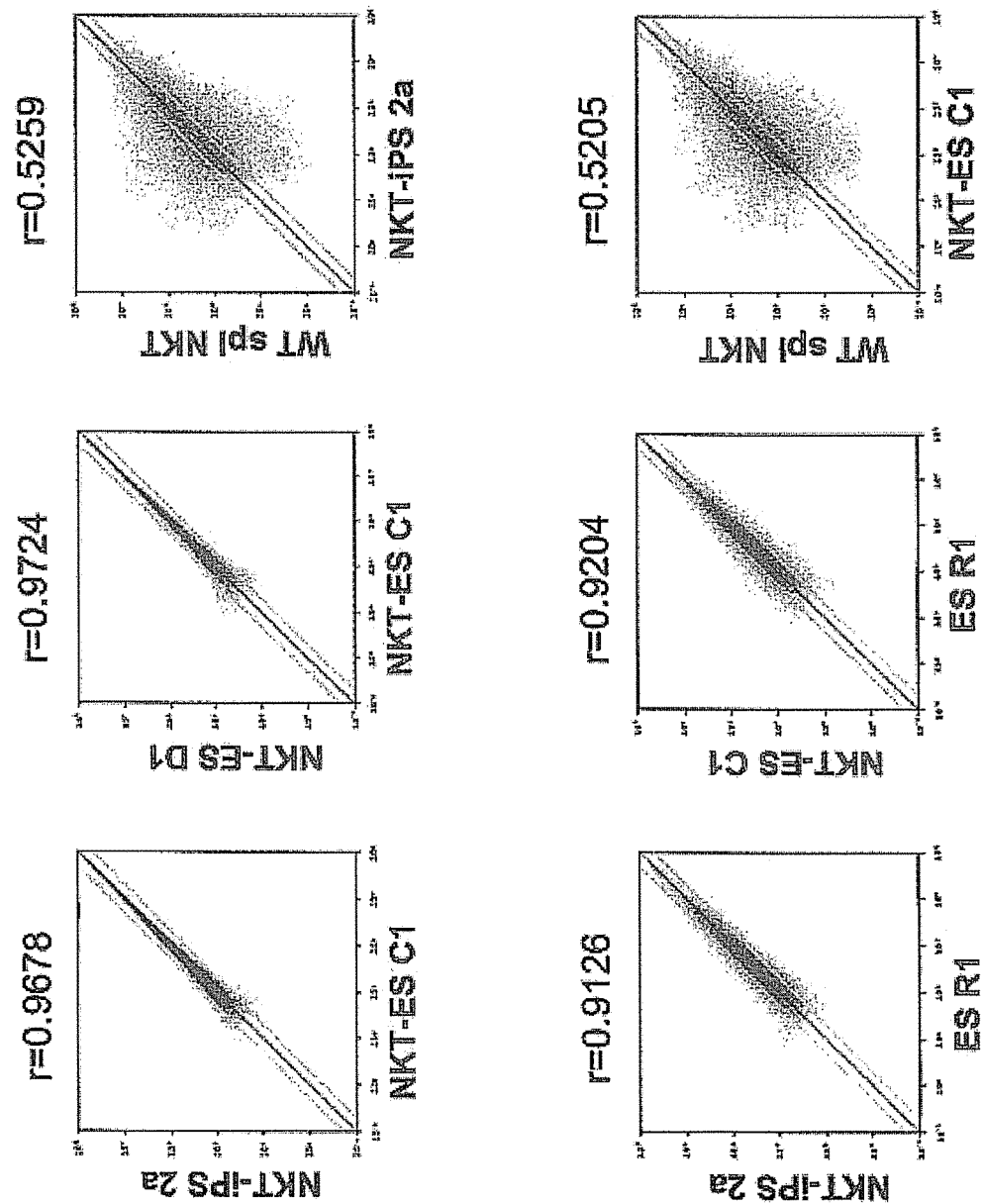
FIG. 4 is a drawing showing the correlations of gene expression profiles between NKT-iPS cells and NKT-ES cells or ES cells, and between NKT-iPS cells and wild type spleen NKT cells.

Furthermore, using a DNA microarray (produced by Affimetrix Company), gene expression profile correlations were checked among NKT-iPS cells, NKT-ES cells, ES cells, and peripheral NKT cells; it was found that the NKT-iPS cells had a gene expression pattern very similar to that of the NKT-ES cells or the ES cells, being distinct from the peripheral NKT cells (FIG. 4).

(4) Morphological Examination of NKT-iPS Cells

Figure 5:
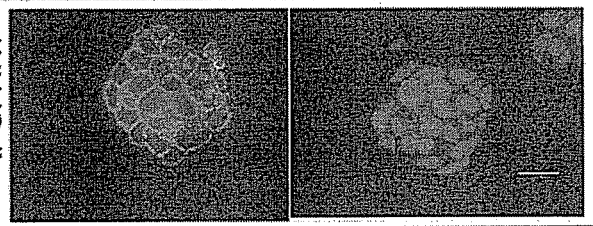
FIG. 5 is a drawing showing the similarity of NKT-iPS cells to MEF-derived iPS cells or ES cells in morphology and the expression of the SSEA1 and Oct3/4 genes.

The morphology of the NKT-iPS cells established in the above-mentioned (2) was examined under a microscope. As a result, it was demonstrated that the localized expression of SSEA1 and Oct3/4 and the morphology of the NKT-iPS cells were very similar to those of ES cells (FIG. 5).

(5) Establishment and Analysis of NKT-iPS Chimeric Mouse

Figure 6:
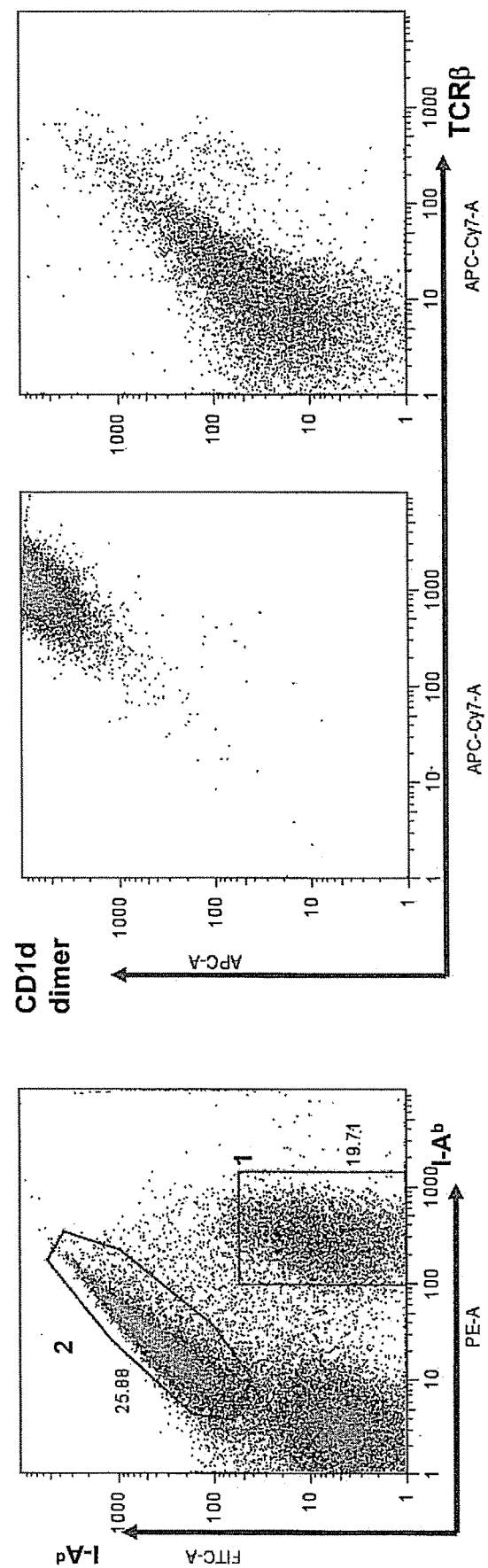
FIG. 6 is a drawing showing TCRα/β expression in cells derived from each of C57BL/6 and Balb/C mice in splenocytes of an NKT-iPS chimeric mouse generated from a C57BL/6 mouse-derived NKT-iPS cell clone 2a and Balb/C mouse-derived cells.

A chimeric mouse was generated from an NKT-iPS cell derived from the C57BL/6 mouse NKT clone established in the above-mentioned (2) and a Balb/c-derived cell by the aggregation method. Splenocytes of the chimeric mouse obtained were analyzed for cell surface antigens. C57BL/6-derived cells and Balb/c-derived cells were gated by distinction by MHC class I (I-$A^b$ and I-$A^d$, respectively), and the NKT cell content ratios were analyzed. As a result, almost all of the C57BL/6-derived cells had a surface antigen like that of α-GalCer loaded CD1d dimer-positive/TCRβ-positive NKT cells, whereas the Balb/c-derived cells contained T/NKT cells at an ordinary frequency (FIG. 6).

Reference Example 1

Establishment and Characterization of iPS Cell from Human T Cell

T cells of human peripheral blood were forcibly expressed by infection with KSOM-containing virus vector, and co-cultivated with mouse embryonic fibroblasts for 21-35 days to establish iPS cells (Cell Stem Cell 7: 11-14, 15-19, 20-24 (2010)). The thus-established iPS cells were confirmed to show a comprehensive gene expression profile and an epigenome state of ES-related gene, which are highly correlated with those of human ES cell, and have a T cell receptor region after gene rearrangement.

Example 2

Establishment and Characterization of iPS Cells from Human NKT Cells

CD1d-restricted NKT cells present in human peripheral blood or cord blood are cells expressing both Vα24 and Vβ11, and accounts for about 0.001%-0.1% of mononuclear cells. After preparing mononuclear cells, positive cells are separated at high purity by sorting using an anti-human Vα24 antibody, anti-human Vβ11 antibody and soluble human CD1d recombinant pulsed with glycolipid ligand (α-GalCer etc.) or, according to the method described in Nature Protoc, 3: 70-78 (2008), adding glycolipid ligand to mononuclear cells and culturing the cells for about 3 days to 1 month to increase NKT cells in vitro, and preparing the cells at high purity by sorting. The purified NKT cells are seeded on a plate having anti-human CD3 antibody and anti-human CD28 antibody immobilized thereon, cultured in the presence of cytokine such as IL-2, IL-12, IL-23, IL-25 and the like, infected with KSOM incorporated into a virus vector such as lentivirus, Hemagglutinating Virus of Japan and the like for forcible expression, and co-cultivated with mouse embryonic fibroblasts and the like for 1-2 months to establish NKT cell-derived iPS cells (NKT-iPS cells).

Example 3

(1) In Vitro Differentiation Induction from Mouse NKT-iPS Cells

Figure 7:
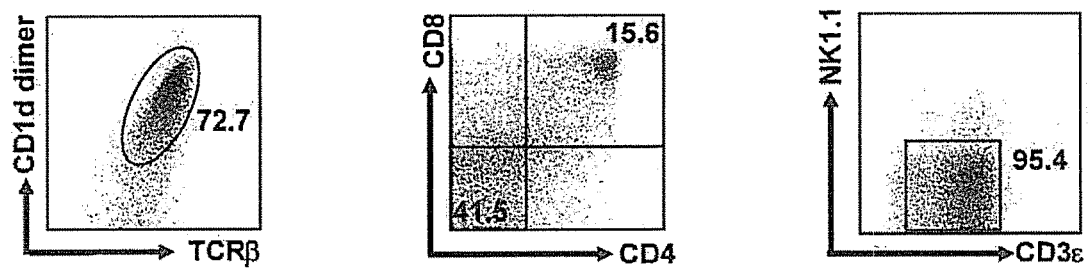
FIG. 7 is a drawing showing the in vitro differentiation induction of DP-NKT cells from NKT-iPS cells.
Figure 8:
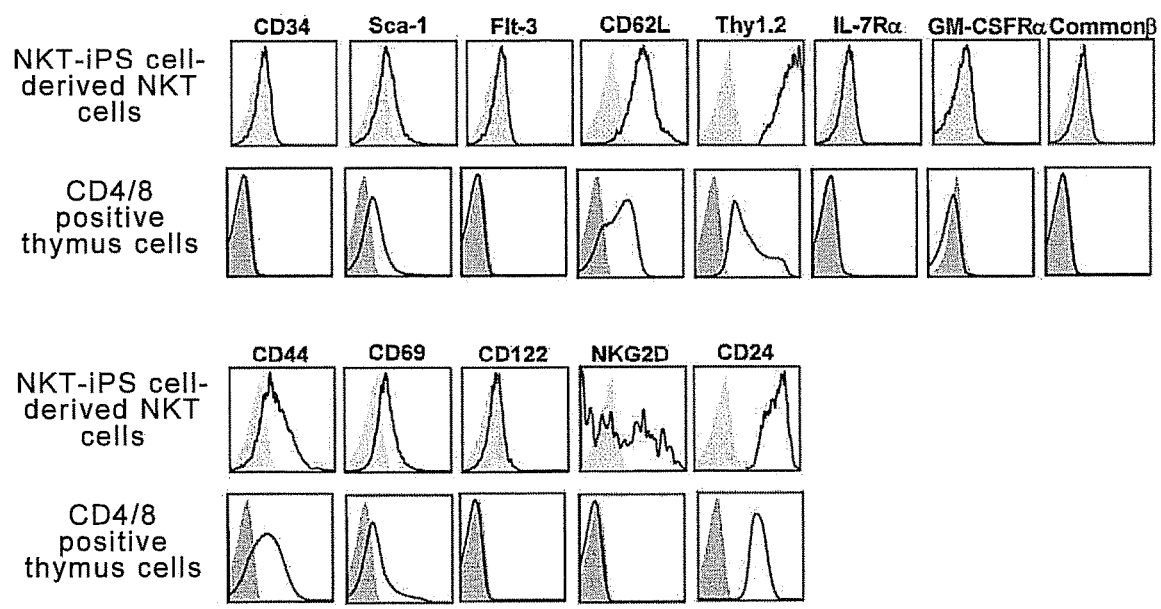
FIG. 8 is a drawing showing results of a phenotype analysis of DP-NKT cells.

ES cells can be differentiation-induced into CD4/CD8-double positive (DP) T cells by being co-cultured with OP9 stromal cells forcedly expressing the Notch ligand Delta-like 1 (Dll-1) (OP9/Dll-1) in the presence of IL-7 and an Flt3 ligand (FL) (Schmitt T M, de Pooter R F, Gronski M A, Cho S K, Ohashi P S, Zuniga-Pflucker J C. Induction of T cell development and establishment of T cell competence from embryonic stem cells differentiated in vitro. Nat. Immunol. 2004 April; 5(4):410-417.). On the basis of this finding, NKT-iPS cells were co-cultured with OP9/Dll-1 cells in the presence of IL-7 (1 ng/ml) and FL (5 ng/ml) for 20 days; it was demonstrated that CD4/CD8 DP α-GalCer loaded CD1d dimer-positive/TCRβ-positive NKT cell-like cells (NKT-iPS cell-derived DP-NKT cells) would be induced (FIG. 7). A cell surface antigen expression analysis was performed in more detail, demonstrating that the phenotype of the DP-NKT cells is very similar to that of CD4/CD8 DP cells in the thymus (FIG. 8). This result suggests that NKT-iPS cells, under the influence of TCRα region gene rearrangement, may be likely to undergo differentiation induction to NKT-like cells, and also shows that by introducing a new concept making the best use of the gene rearrangement in immunocytes, it is possible to secure a technology for generating desired immunocytes (particularly NKT cells, T cells, B cells) in large amounts.

Figure 9:
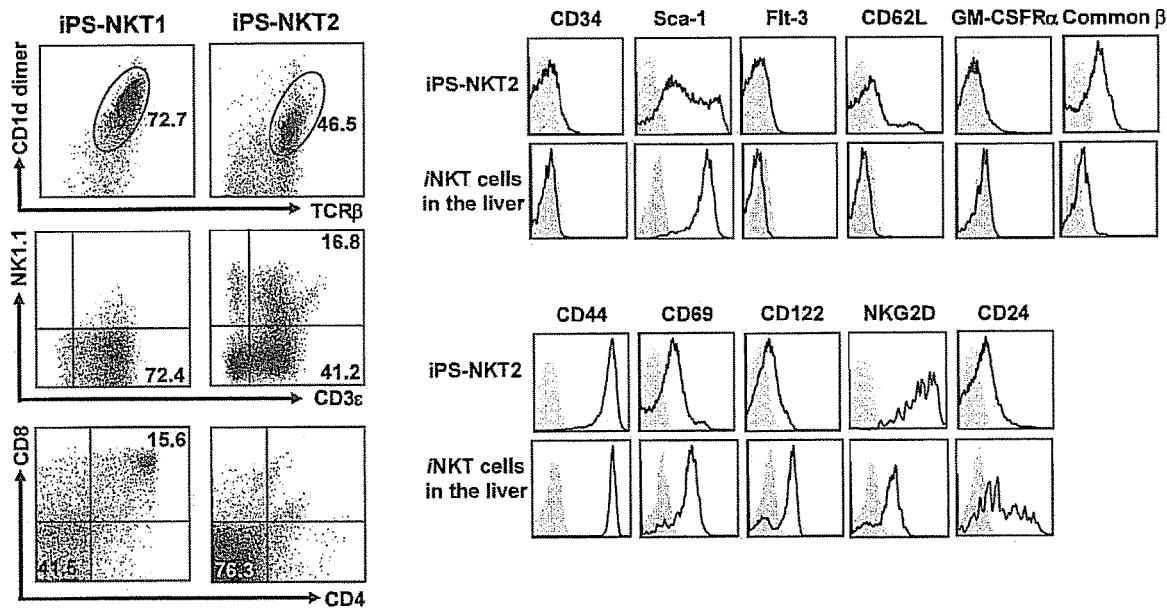
FIG. 9 is a drawing showing the in vitro differentiation induction of NKT cells that exhibit the same phenotype as peripheral NKT cells, from NKT-iPS cells.

(2) In Vitro Differentiation Induction of Mature NKT Cells from Mouse NKT-iPS Cells An analysis was performed to determine whether NKT cells would be induced by co-culturing NKT-iPS cells with OP9/Dll-1 until day 14 of cultivation, and then with OP9 from day 14 to day 20 of cultivation. As a result, it was found that NKT cells could emerge even in an early differentiation stage wherein only what is called DN1, which is Lin-negative/CD44-positive/CD25-negative, had emerged (FIG. 9), and that the surface markers of the differentiation-induced NKT cells were very similar to those of peripheral NKT cells (FIG. 9). This result shows that NKT cells are capable of differentiating into mature NKT cells even if the Notch signal is lacked in an early differentiation stage.

Figure 10:
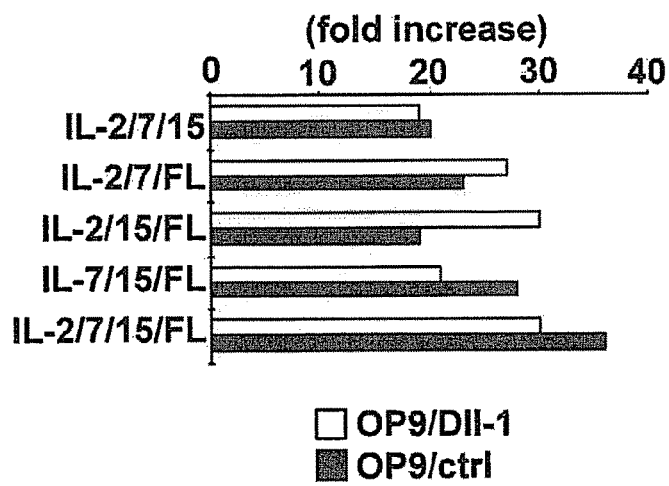
FIG. 10 is a drawing showing the mass expansion of NKT cells from DP-NKT cells using various combinations of cytokines.
Figure 12:
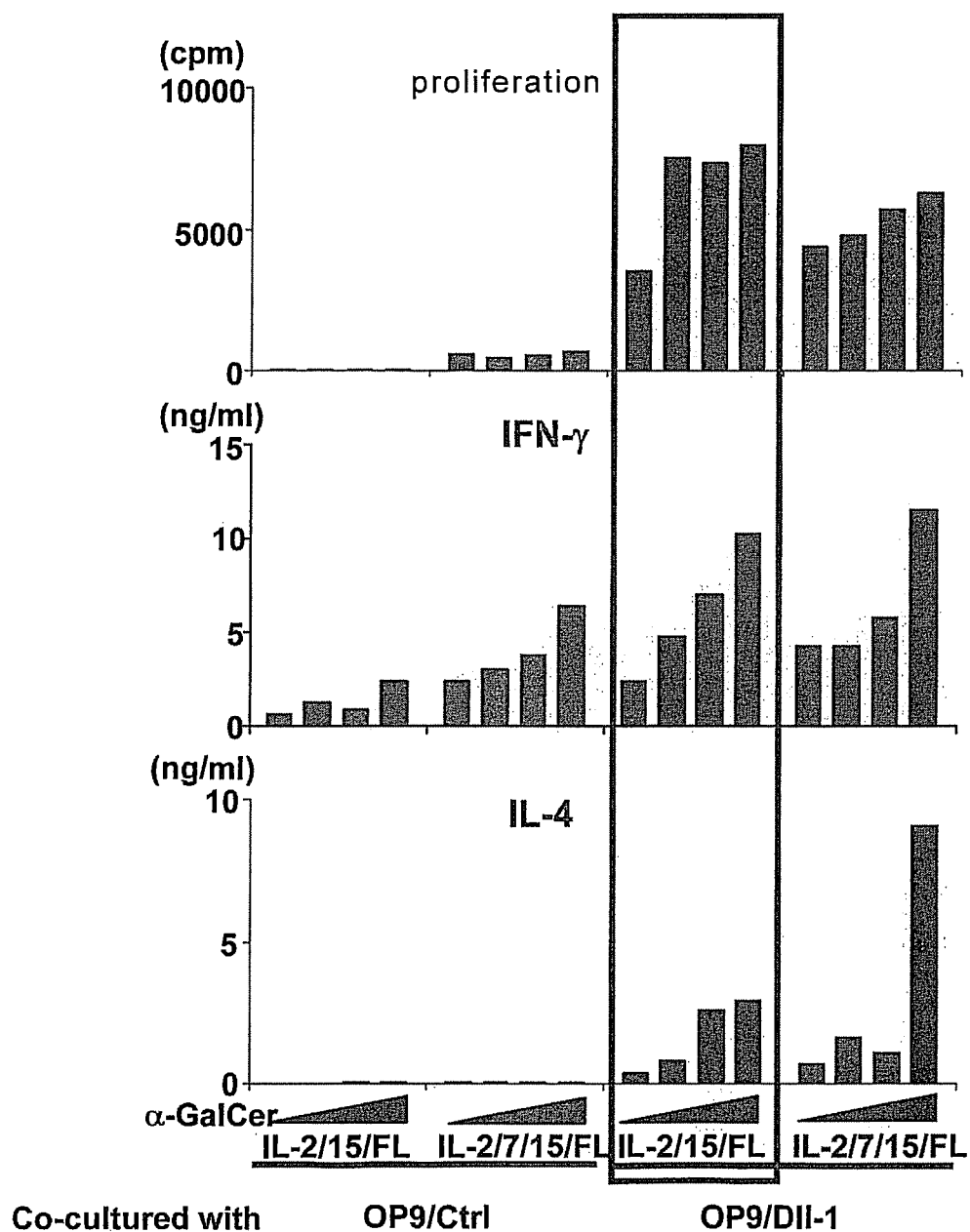
FIG. 12 is a drawing showing the α-GalCer responsiveness of NKT cells differentiation-induced from NKT-iPS cells.

(3) In Vitro Differentiation Induction of Mature NKT Cells from Mouse NKT-iPS Cell-Derived DP-NKT Cells To further expand and mature NKT-iPS cell-derived DP-NKT cells whose induction was confirmed in the above-mentioned (1), in vitro, the cells were cultured using various combinations of cytokines with or without feeder cells for 5 days. As a result, it was demonstrated that by co-cultivation with OP9 or OP9/Dll-1 in the presence of the IL-2/IL-15/FL or IL-2/IL-7/IL-15/FL cytokine combination, the cells could be further expanded more than 10 times (FIG. 10). Furthermore, it was estimated that the cells cultured under these conditions had undergone further differentiation induction, with the expression of NK1.1 induced therein (FIG. 11). Hence, the NKT cells obtained by induction by co-cultivation with OP9 or OP9/Dll-1 in the presence of the IL-2/IL-15/FL or IL-2/IL-7/IL-15/FL cytokine combination were co-cultured with bone marrow cell-derived dendritic cells (induced with GM-CSF) in the presence of α-GalCer, whereby the proliferation potential and cytokine productivity thereof were checked. As a result, it was confirmed that a proliferation potential was observed when the cells were further cultured with OP9/Dll-1 (FIG. 12), and that a bias to Th1 existed particularly when cultured with IL-2/IL-15/FL (FIG. 12).

Example 4

In Vitro Differentiation Induction of Human NKT-iPS Cells into Mature NKT Cells

Human NKT-iPS cells are co-cultivated with mouse bone marrow stroma cell line OP9 and cell line OP9/Dll-1 obtained by forcible expression of Dll-1 (Notch ligand) therein, whereby the human NKT-iPS cells are differentiated into human NKT cells. That is, human NKT-iPS cells are cultured with OP9 for 12 to 14 days, differentiated cells are recovered, and further co-cultivated with OP9/Dll-1 cells in the presence of cytokine such as IL-7, Flt-3L, SCF and the like for 15-30 days, whereby the CD1d-restricted NKT cells can be induced to differentiate.

Example 5

Adjuvant Effect of Mouse NKT-iPS Cell-Derived Mature NKT Cells In Vivo

Figure 13:
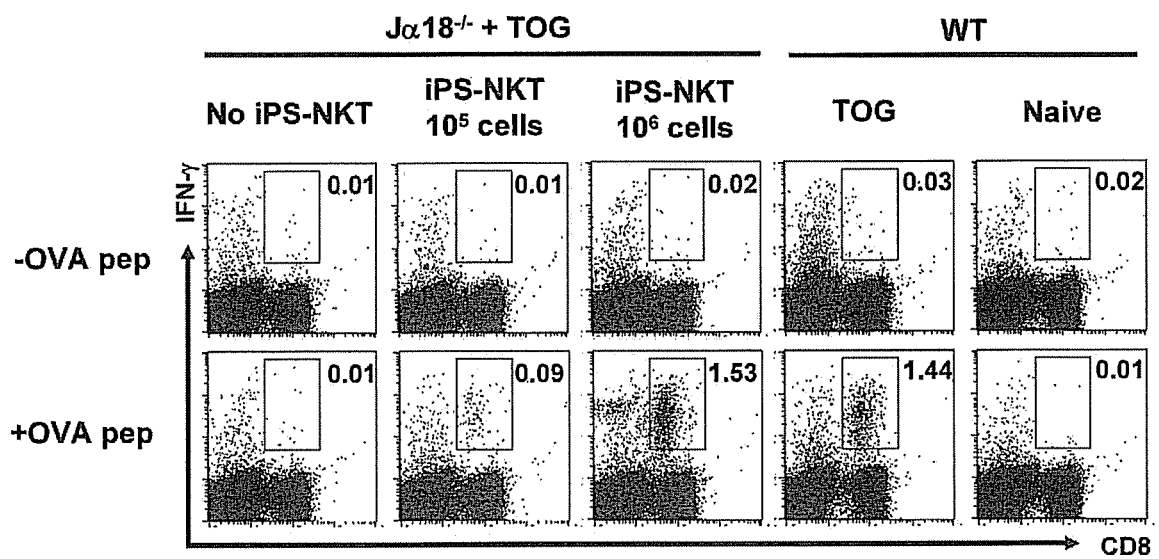
FIG. 13 is a drawing showing the in vivo adjuvant effect of NKT cells differentiation-induced from NKT-iPS cells.

An evaluation was performed to determine whether the NKT-iPS cell-derived mature NKT cells induced in Example 3(3) (co-cultured with OP9/Dll-1 in the presence of IL-7/FL for 20 days, then with OP9/Dll-1 in the presence of IL-2/IL-15/FL for 5 days) were functional in vivo. TAP knockout mouse-derived splenocytes were cultured with 10 mg/ml ovalbumin (OVA) in a hypertonic solution, after which apoptosis was induced, and $2 \times 10^7$ apoptotic cells, along with 2 μg of α-GalCer, were transferred to a Jα18 knockout mouse (NKT cell-deficient mouse) having $10^5$ or $10^6$ NKT-iPS cell-derived mature NKT cells transferred in advance 1 hour previously. Seven days later, splenocytes were collected from the mouse, stimulated with OVA peptide (257-264) in vitro, and analyzed for IFN-γ production by intracellular staining. As a result, it was confirmed that OVA-antigen specific CD8-positive T cells possessing IFN-γ productivity had been induced dependently on the number of cells transferred, demonstrating that the NKT-iPS cell-derived mature NKT cells function in vivo and have a potent adjuvant effect (FIG. 13).

Example 6

Adjuvant Effect of Mouse NKT-iPS Cell-Derived Mature NKT Cell in Allo Vivo

When MHC is mismatched in cell transfer or organ transplantation, the transferred cells and transplanted organs are known to be rejected. For example, when NKT cells (C57BL/6 background) induced to differentiate from NKT-iPS cells established from C57BL/6 mouse are transplanted into BALB/c mouse, the transferred NKT cells are rejected by the host BALB/c mouse. However, by activating the NKT cells immediately after transfer, both the innate immune system and acquired immune system can be activated. The immune system is activated by transferring, simultaneously with NKT cell transfer, dendritic cells pulsed with a medicament such as α-GalCer and the like that specifically activates NKT cells.

Example 7

Adjuvant Effect of Human NKT-iPS Cell-Derived Mature NKT Cells In Vivo

NKT cells induced to differentiate from human NKT-iPS cells are transferred into an immune system humanized mouse (HLA-completely different) produced by transferring hematopoietic stem cells into an NOD/SCID/Common γ knockout mouse, which is a severe immunodeficiency mouse. As in the case of mouse, since human iPS cell-derived NKT cells are also rejected rapidly, it needs to be activated simultaneously with or immediately after transfer. In this case, when dendritic cells (monocyte-derived dendritic cells induced from monocyte by GM-CSF and IL-4, or Lineage-negative CD11c-positive CD123-negative myeloid dendritic cells etc.) pulsed with an NKT cell ligand such as α-GalCer and the like, or α-GalCer is transferred simultaneously with the NKT cells, the NKT cells are activated before rejection in vivo, and can exhibit antitumor effect and adjuvant effect.

Example 8

Establishment of iPS Cells from Wild Mouse Splenocyte-Derived NKT Cells

Figure 14:
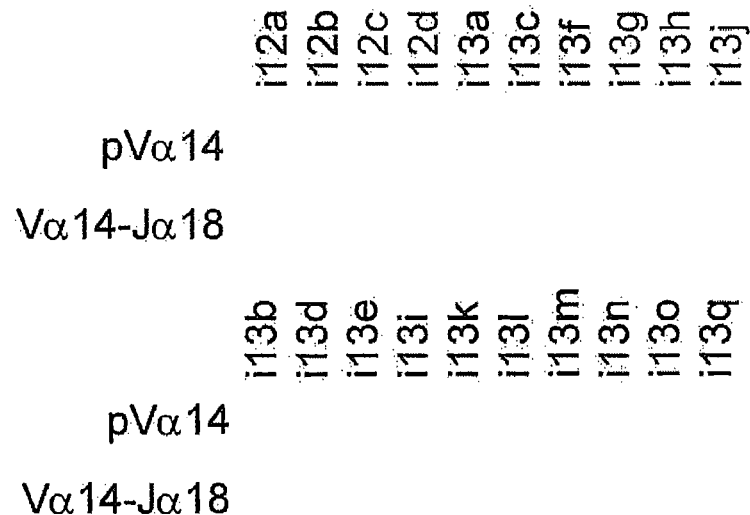
FIG. 14 is a drawing showing the establishment of iPS cells from C57BL/6 wild mouse splenocytes.

In Examples 1, 3 and 5, the establishment of NKT-iPS cells from a purified mouse NKT cell population, differentiation induction from the NKT-iPS cells to NKT cells, the possession by the cells of a function as NKT cells, and the like were demonstrated. Hence, by the same procedure as Example 1, NKT cells were prepared from splenocytes of a C57BL/6 mouse without a concentrating operation, whereby an NKT cell population of about 30-50% purity was obtained. These cells were cultured in the presence of IL-2 (10 ng/ml) at a cell density of $10^6$ cells/ml for 24 hours in the same manner as in Example 1, after which the cells were infected with a retrovirus containing four mouse-derived factors (nucleic acids that encode Oct3/4, Sox2, Klf4, and c-Myc) ($10^6$ pfu/ml) for 24 hours. Three to seven days after the viral infection, the cells were recovered, re-seeded onto mouse embryonic fibroblasts (MEF), and co-cultured in the presence of LIF using an ES cell culture medium. The emerging colonies were morphologically evaluated, and colonies assuming an ES-like morphology were picked up and further cultured in the presence of LIF on MEF, whereby 5 clones of NKT-iPS cells were successfully established (clone code name: il2c, il2d, il3g, il3h, il3i) (FIG. 14).

Reference Example 2

Generation of NKT Clone Mouse with C57BL/6 Background

Figure 15:
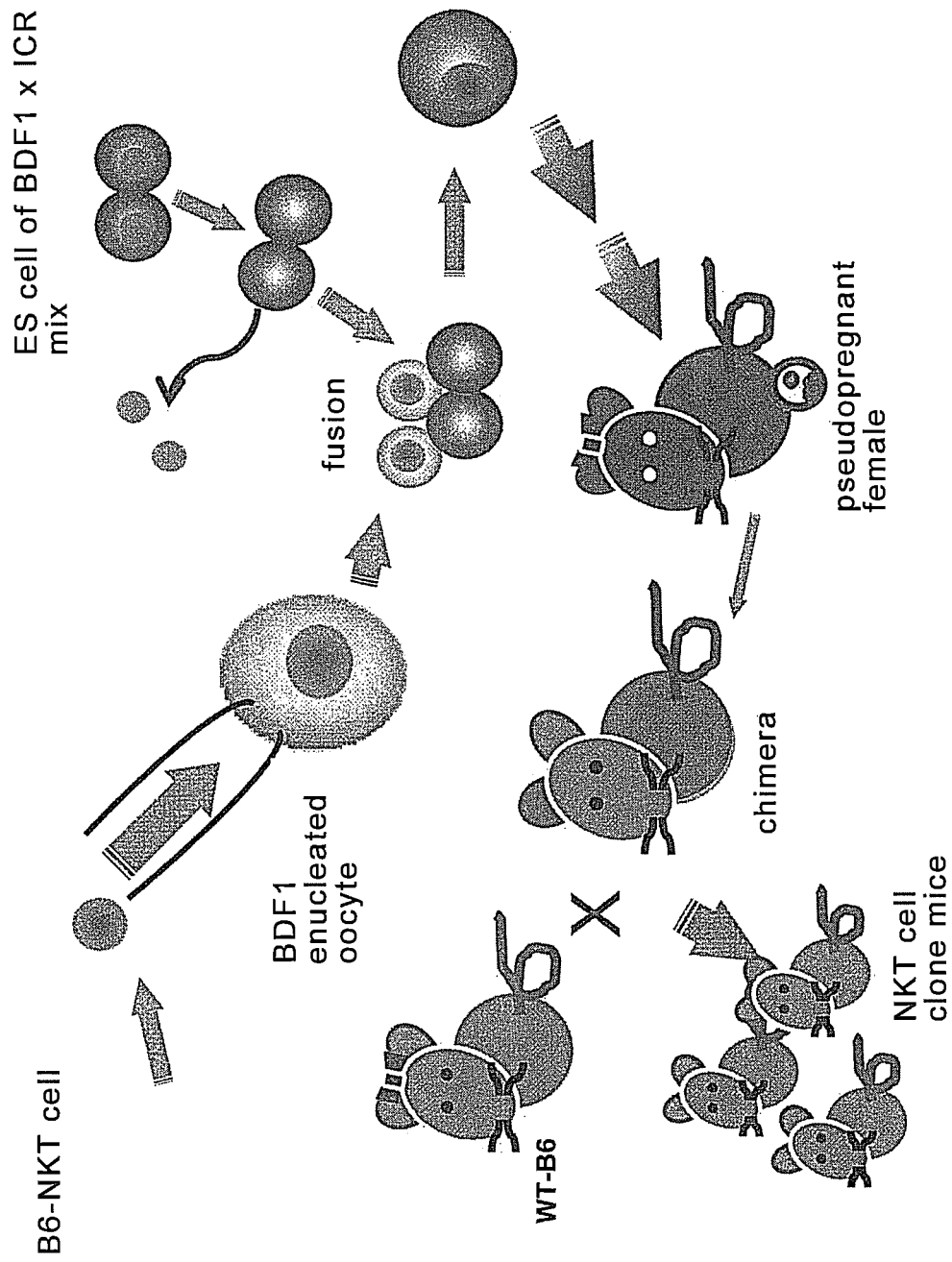
FIG. 15 is a drawing showing the generation of an NKT clone mouse with C57BL/6 background.

As shown in FIG. 15, for the purpose of performing a cell transfer experiment, an NKT clone mouse with C57BL/6 background was generated. That is, the nucleus of a C57BL/6 mouse spleen-derived NKT cell was transferred into an enucleated oocyte of a BDF1 mouse. This cell was fused with an ES cell of BDF1×ICR, transferred to the uterus of a foster mother, and an offspring chimeric mouse was obtained. The chimeric mouse (male) obtained was crossed with a C57BL/6 mouse (female), and the offspring obtained was used as the NKT clone mouse with C57BL/6 background.

Figure 16:
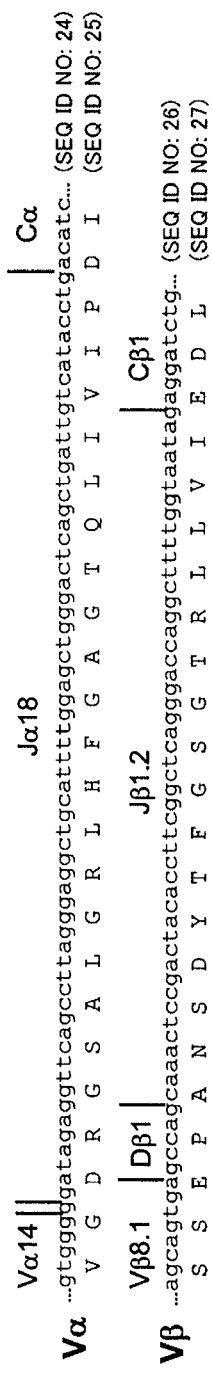
FIG. 16 is a drawing showing the base sequence of the T cell receptor region of an NKT clone mouse with C57BL/6 background.

In the NKT clone mouse established using this method, the starting nucleus was 100% derived from an NKT cell derived from the spleen of the C57BL/6 mouse; therefore, the clone mouse is a complete C57BL/6, and does not undergo an allogenic or semi-allogenic reaction with the C57BL/6 mouse. The only genomic difference between the NKT clone mouse with C57BL/6 background and the C57BL/6 mouse seems to be the difference in sequence due to T cell receptor region rearrangement as a result of the differentiation into NKT cells. The base sequence of the T cell receptor region of an NKT clone mouse with C57BL/6 background wherein rearrangement has completed is shown in FIG. 16.

Example 9

Figure 17:
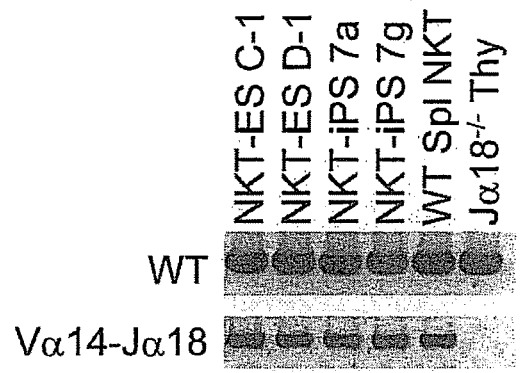
FIG. 17 is a drawing showing a gene rearrangement analysis of NKT-iPS cell clones 7a and 7g.
Figure 18:
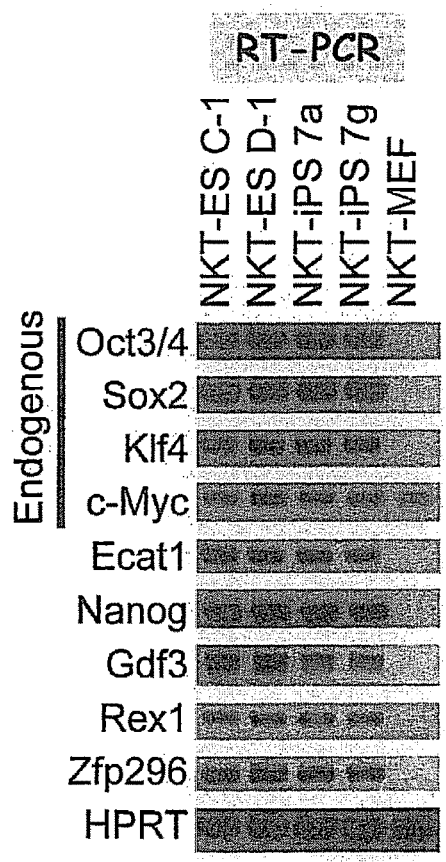
FIG. 18 is a drawing showing a gene expression analysis of NKT-iPS cell clones 7a and 7g.
Figure 20:
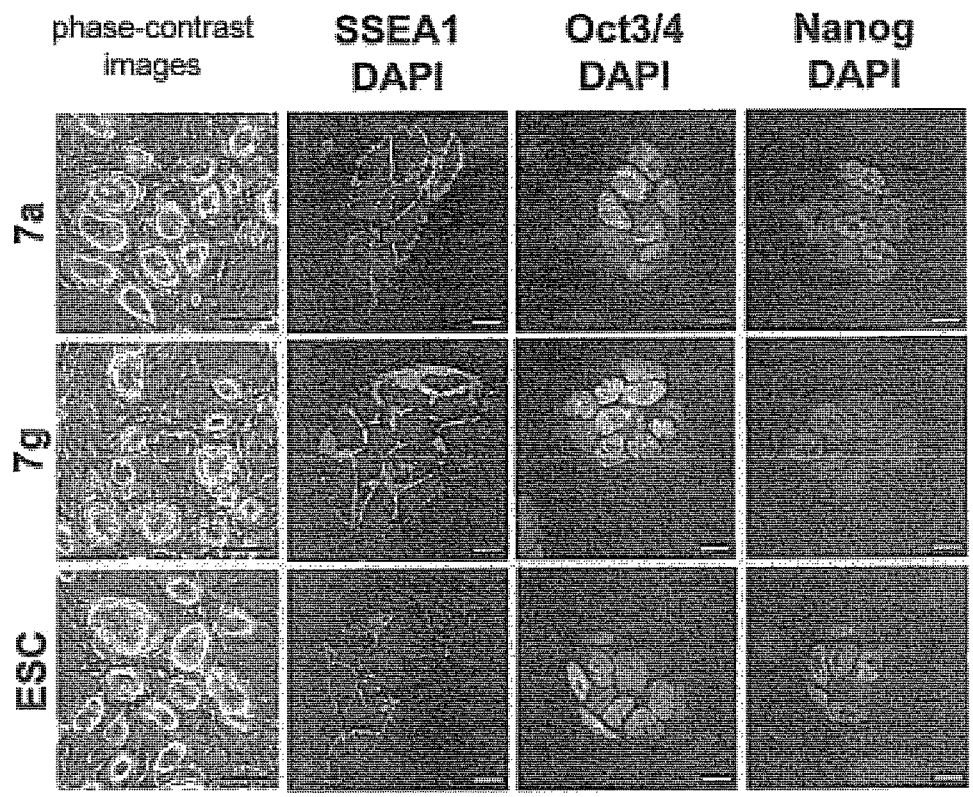
FIG. 20 is a drawing showing morphology and the expression of ES cell markers in NKT-iPS cell clones 7a and 7g.
Figure 21:
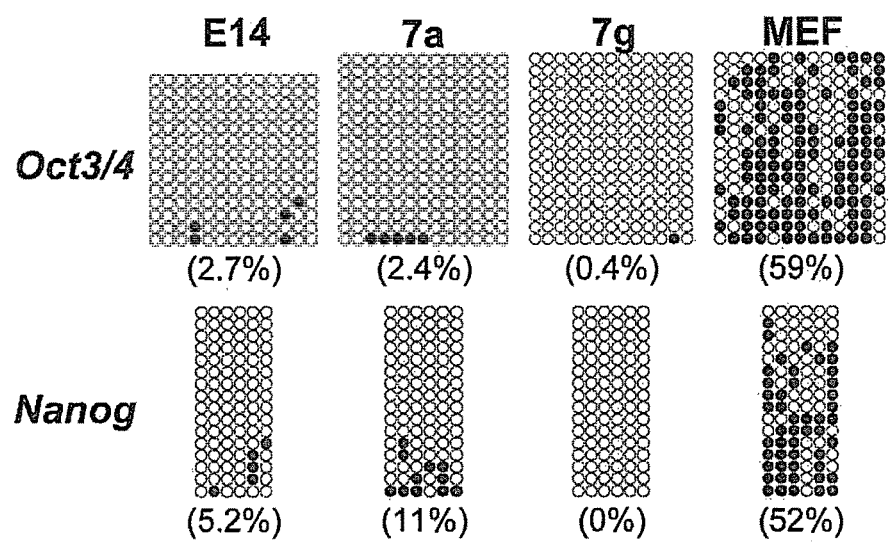
FIG. 21 is a drawing showing a DNA methylation analysis of NKT-iPS cell clones 7a and 7g.
Figure 22:
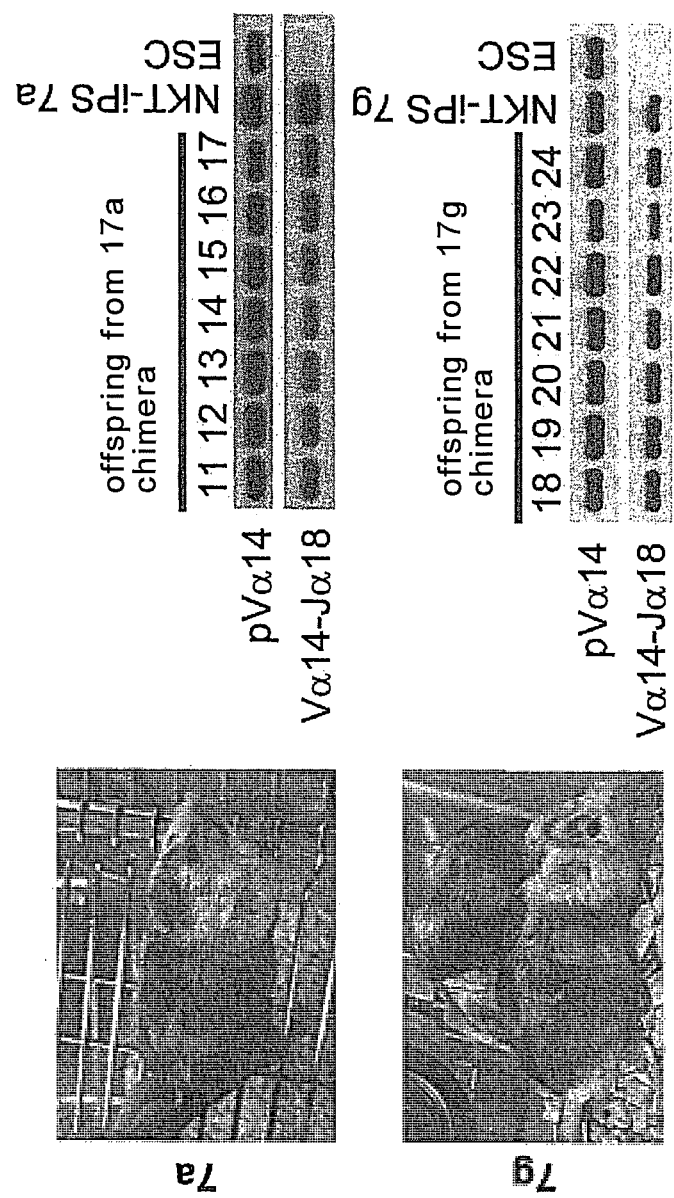
FIG. 22 is a drawing showing the transmission of NKT-iPS cell clones 7a and 7g to offspring.

Establishment of iPS Cells Derived from NKT Clone Mouse-Derived Embryonic Fibroblasts The conventional method of establishing a mouse iPS cell, established by Yamanaka et al., is based on the introduction of Oct3/4, Sox2, Klf4, and c-Myc into an embryonic fibroblast (MEF). Hence, an attempt was made to establish an iPS cell from MEF of an NKT clone mouse created in Reference Example 2, and NKT-iPS cells 7a and 7g were successfully established. The established 7a and 7g were confirmed as having the T cell receptor region undergoing gene rearrangement to the T cell receptor of NKT cells (FIG. 17), and were also confirmed by a RT-PCR method as being equivalent to ES cells in terms of the expression of a group of genes that can be ES cell markers (FIG. 18). Also, a comprehensive gene expression analysis using a DNA microarray and a cluster analysis thereof yielded results showing that the established 7a and 7g were close to ES cells and distant from the starting MEF of the NKT clone mouse (FIG. 19). Furthermore, morphological examination thereof was performed; it was also confirmed that 7a and 7g were morphologically very similar to ES cells, and that the ES cell markers SSEA1, Oct3/4, and Nanog were expressed (FIG. 20). Furthermore, the genome methylation tendency of the gene expression regulatory regions of Oct3/4 and Nanog was analyzed, demonstrating sufficient reprogramming in 7a and 7g, wherein the genomes were unmethylated to the same extent as with the ES cells (FIG. 21). Also, a plurality of chimeric mice were born from 7a and 7g, and all the offspring obtained by crossing with a C57BL/6 mouse exhibited gene rearrangement to the T cell receptor of NKT cells, confirming transmission to offspring, and demonstrating that 7a and 7g possess pluripotency (FIG. 22). From the above, it was concluded that 7a and 7g satisfied the criteria for iPS cells.

Example 10

Figure 23:
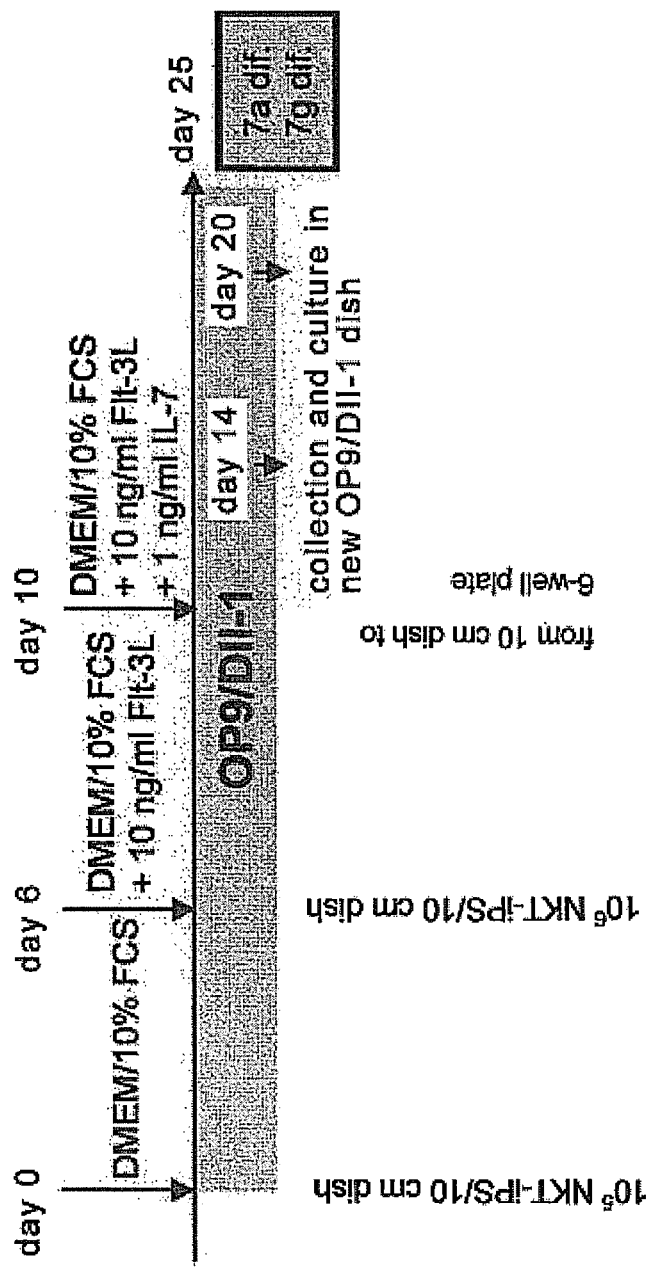
FIG. 23 is a drawing showing a method of in vitro induction of differentiation of NKT cells from NKT-iPS cell clones 7a and 7g.
Figure 24:
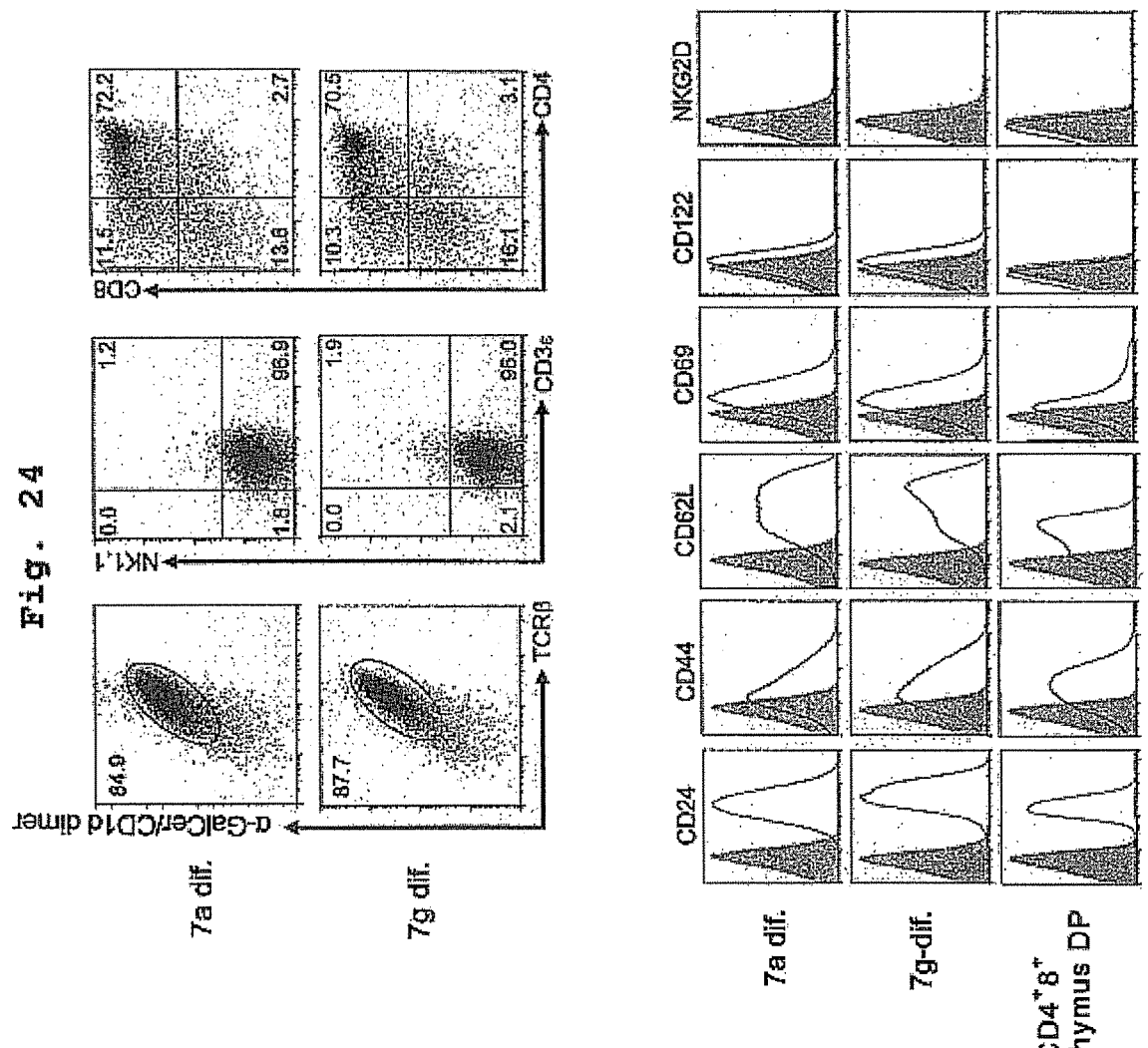
FIG. 24 is a drawing showing the expression of cell surface markers in cells differentiation-induced from NKT-iPS is cell clones 7a and 7g in vitro.
Figure 25:
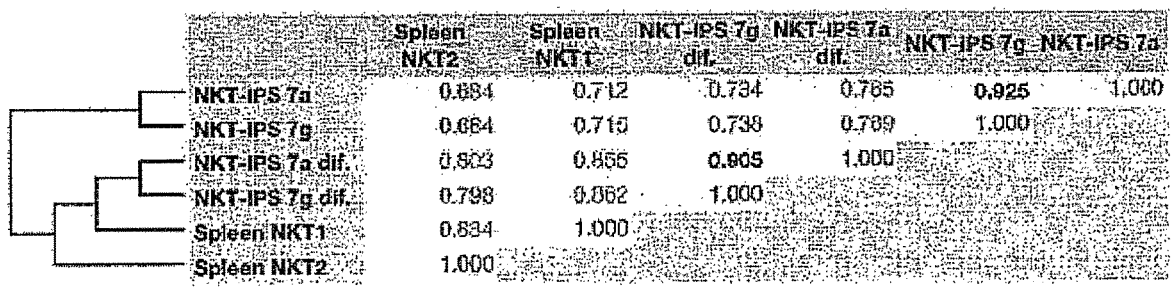
FIG. 25 is a drawing showing a comprehensive gene expression correlation analysis of cells 7a dif. and 7g dif. differentiation-induced in vitro.
Figure 26:
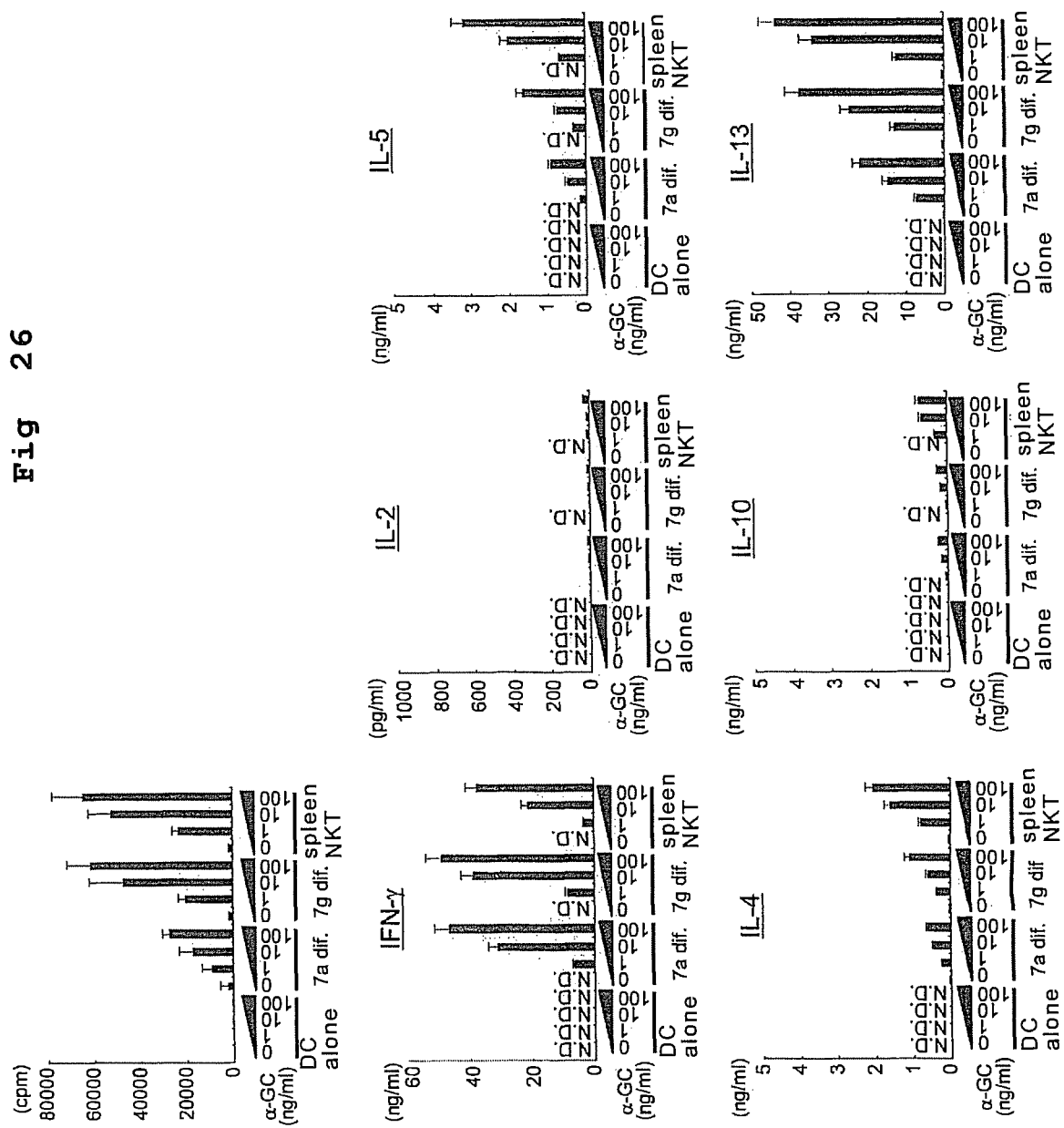
FIG. 26 is a drawing showing an in vitro functional analysis of cells 7a dif. and 7g dif. differentiation-induced in vitro.

In Vitro Differentiation Induction from NKT Clone Mouse MEF-Derived iPS Cell into NKT Cell Next, an investigation was performed to determine whether it was possible to differentiation-induce NKT cells from MEF-derived 7a and 7g in vitro. 7a and 7g were co-cultured with OP9/Dll-1, a cell line prepared by forcing the bone marrow-derived stromal cell OP9 to express the Notch ligand Dll-1, per the protocol shown in FIG. 23 for 25 days. As a result, as shown in FIG. 24, it was demonstrated that 7a and 7g were differentiation-induced to α-GalCer/CD1d dimer-positive TCRβ-positive NKT cell-like cells (7a dif. and 7g dif.). Furthermore, 7a dif. and 7g dif. were very similar to what are called DP cells, which are CD4-positive CDB-positive cells present in the thymus, in terms of the expression of cell surface markers. Also, a comprehensive gene expression analysis using a DNA microarray and a cluster analysis thereof yielded results showing that 7a dif. and 7g dif. are distant from the 7a and 7g before differentiation induction and close to spleen-derived NKT cells present in the periphery (FIG. 25). Hence, to determine whether 7a dif. and 7g dif. are functionally equivalent to NKT cells, they were stimulated with the glycolipid ligand α-GalCer while being co-cultured with dendritic cells, and examined for a proliferation potential and cytokine productivity. As a result, it was confirmed that 7a dif. and 7g dif., like peripheral NKT cells, possess a remarkable proliferation potential and the capability of producing large amounts of IFN-γ and IL-4 (FIG. 26).

Example 11

In Vivo Functional Analysis of 7a Dif. And 7g Dif.

Figure 27:
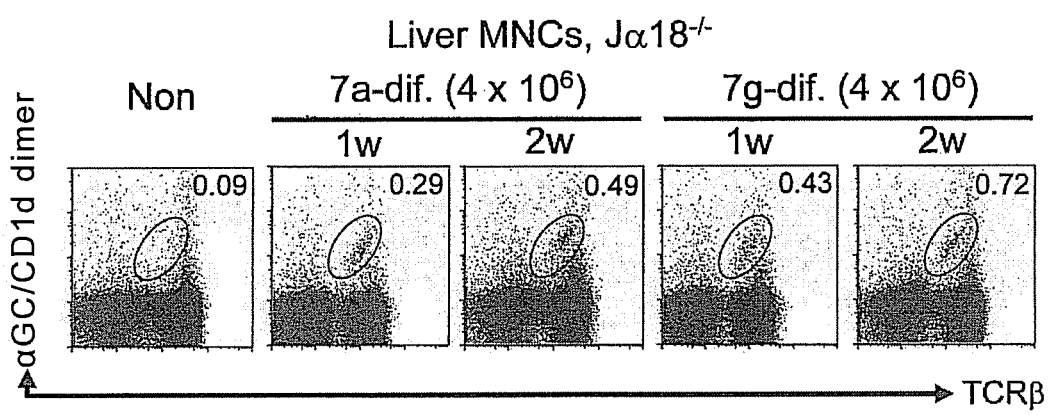
FIG. 27 is a drawing confirming the presence of transferred cells at 1 week (1w) and 2 week (2w) after transfer of cells 7a dif. and 7g dif. differentiation-induced in vitro into an NKT cell-deficient mouse.
Figure 28:
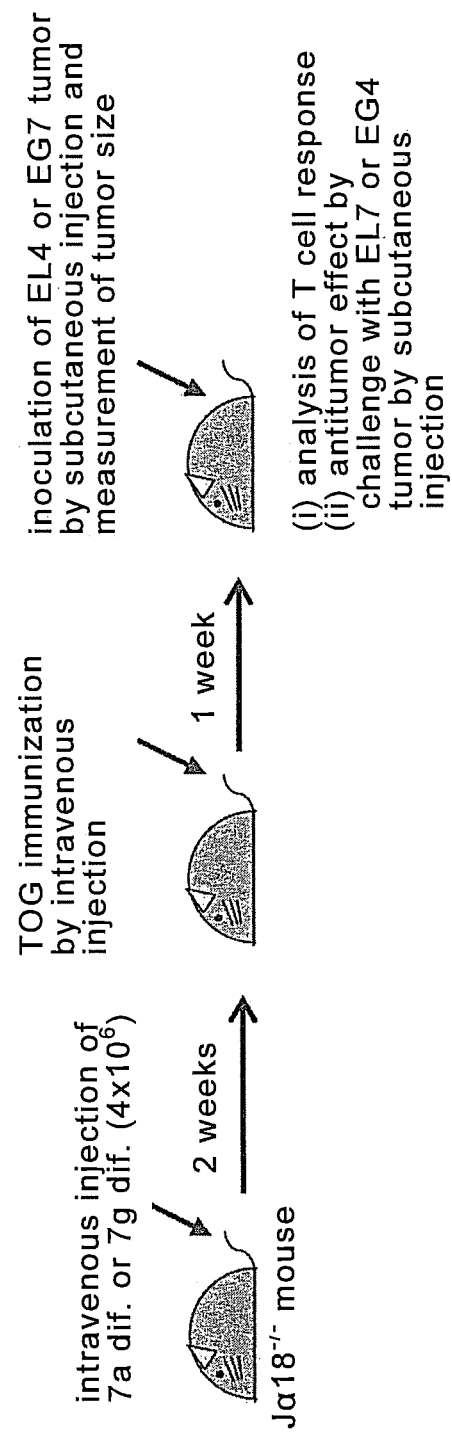
FIG. 28 is a drawing showing the protocol of an in vivo evaluation of cells 7a dif. and 7g dif. differentiation-induced in vitro.
Figure 30:
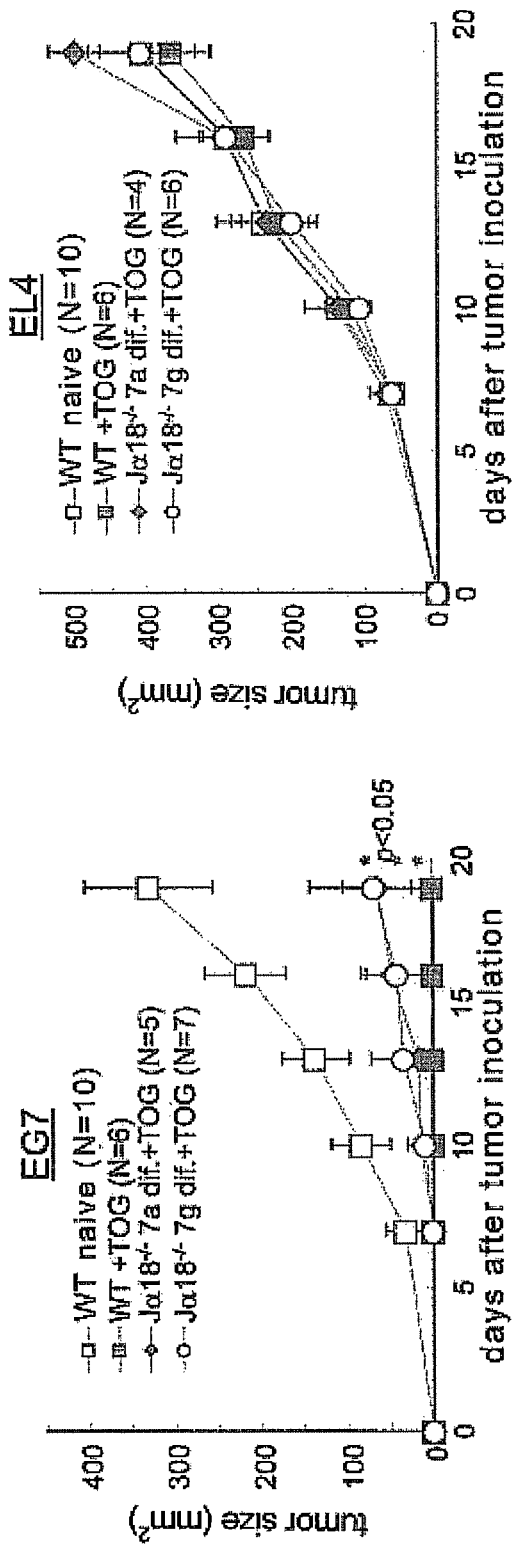
FIG. 30 is a drawing showing the malignant tumor rejection by cells 7a dif. and 7g dif. differentiation-induced in vitro.

Since 7a dif. and 7g dif. are functionally equivalent to peripheral NKT cells, as described in Example 10, an analysis was performed to determine whether the same effect is present in vivo using an NKT cell-deficient mouse. After 7a dif. and 7g dif. were transferred to the NKT cell-deficient mouse, the presence of the transferred cells at 1 week and 2 weeks was checked; it was demonstrated that α-GalCer/CD1d dimer-positive, TCRβ-positive 7a dif. and 7g dif. were present in the liver (FIG. 27). Hence, on the basis of the protocol shown in FIG. 28, the induction of antigen specific CD8-positive T cells and an accompanying antitumor effect were checked. TAP knockout mouse-derived splenocytes were cultured with 10 mg/ml ovalbumin (OVA) in a hypertonic solution, after which apoptosis was induced, and $2 \times 10^7$ apoptotic cells, along with 2 μg of α-GalCer, is were transferred to the NKT cell-deficient mouse having 7a dif. and 7g dif. transferred thereto one week previously (TOG immunization). Seven days later, splenocytes were collected from the mouse, stimulated with OVA peptide (257-264) in vitro, and analyzed for IFN-γ production by intracellular staining. As a result, it was confirmed that OVA-antigen specific CD8-positive T cells possessing IFN-γ productivity had been induced equivalently to a wild type mouse, demonstrating that 7a dif. and 7g dif. function in vivo and have a potent adjuvant effect (FIG. 29). Hence, the mouse was evaluated using a malignant tumor rejection model using the C57BL/6 mouse thymoma cell line EL4 or EG7 (EL4 OVA-transfectant). As a result, with EG7, which is a cell line that forcedly expresses OVA, the non-TOG-immunized wild type mouse exhibited a progression of the malignant tumor, whereas in the TOG-immunized 7a dif.- and 7g dif.-transferred NKT cell-deficient mouse, no progression was found as in the TOG-immunized wild type mouse. With EL4, similar progression was observed in the TOG-immunized wild type mouse and the NKT cell-deficient mouse; therefore, it was concluded that the progression was attributed to the antigen-specific adjuvant effect of the transferred 7a dif. and 7g dif. (FIG. 30).

The results above show that any cells having a T cell receptor rearranged therein can be differentiation-induced into functional immunocompetent cells rearranged to the T cell receptor.

Example 12

Functional Analysis of Human NKT-iPS Cell-Derived Mature NKT Cells In Vivo

In reference to the differentiation induction system of human ES cells into CD4-positive CD8-positive T cell-like cells (J Immunol, 183: 4859-4870 (2009)), human NKT-iPS cells were induced to differentiate into NKT cells in vitro. The NKT-iPS cells are co-cultivated with OP9 cells for 12-14 days. Thereafter, NKT cell-progenitor cells are recovered, and co-cultivated with OP9/Dll-1 cells in the presence of IL-7, Flt3L and SCF for 14-35 days to allow CD1d-restricted Vα24-positive Vβ11-positive NKT cells to appear.

Example 13

Rejection of Allo-iPS-NKT Cells Transferred into Mouse

Rejection rapidly occurs upon transfer of allo-NKT cells into a normal mouse, and the transferred NKT cells are excluded without developing GvH. When a dendritic cell pulsed with NKT cell ligand α-GalCer or α-GalCer is simultaneously transferred under this condition, the NKT cells are activated before rejection in vivo, and antitumor effect and adjuvant effect can be exhibited.

Example 14

How to Establish iPS Cells from Wild Type NKT Cells Efficiently

While the present inventors succeeded in establishing iPS cells from an NKT cell derived from a splenocyte of a wild type mouse, as shown in Example 8, a more efficient method of establishing iPS cells was secured.

Figure 31:
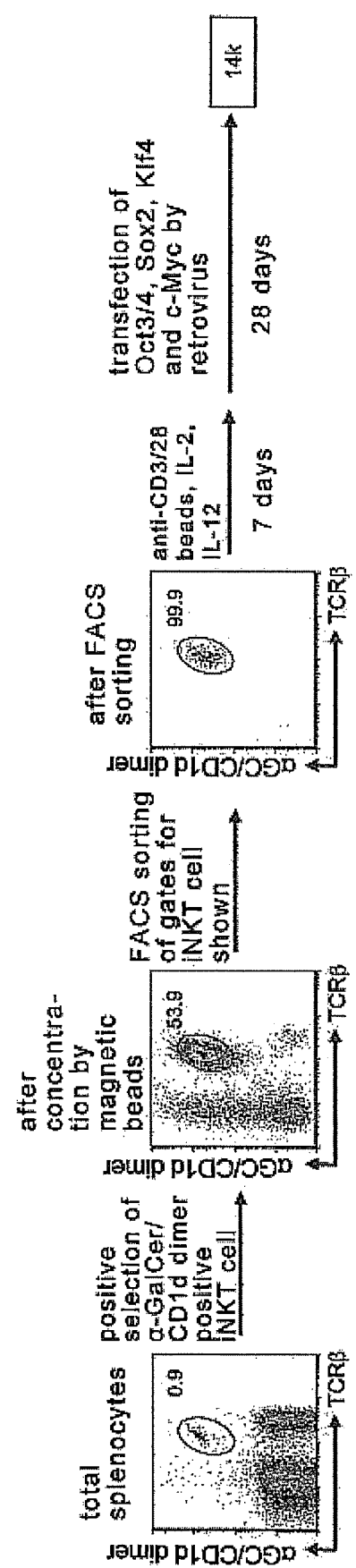
FIG. 31 is a drawing showing a method of efficiently establishing iPS cells from wild type NKT cells.
Figure 32:
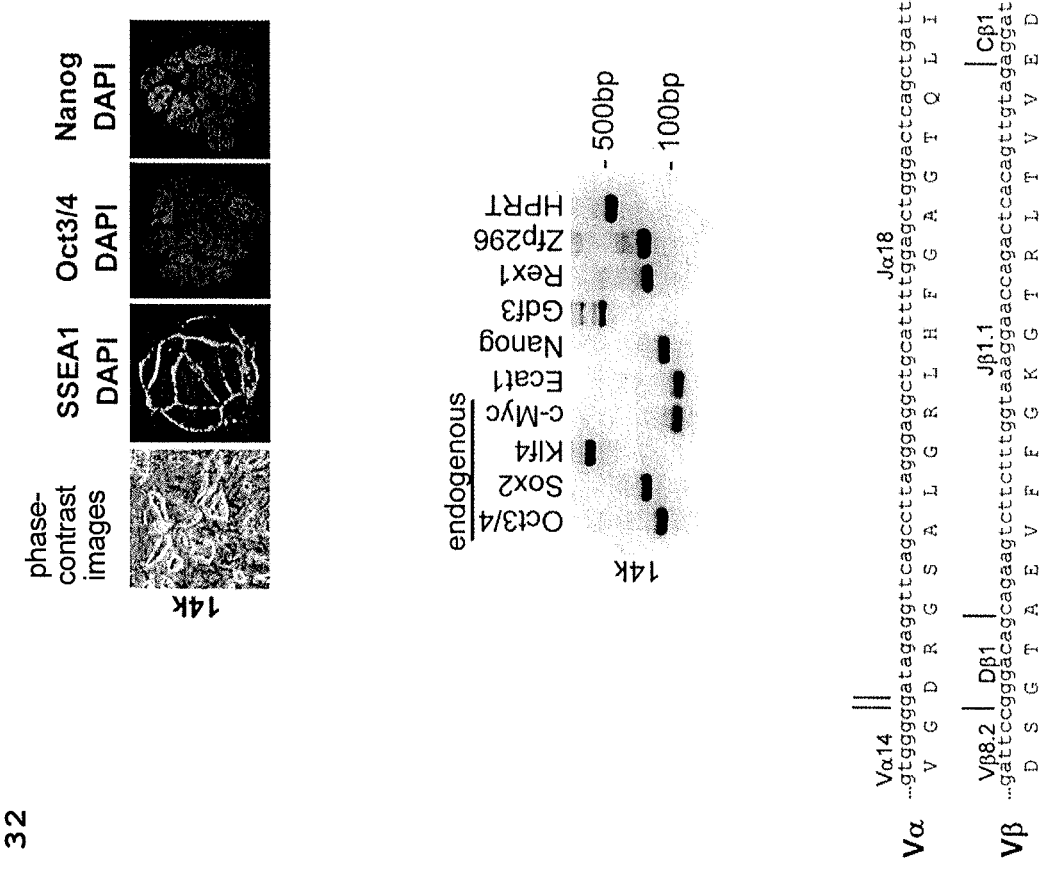
FIG. 32 is a drawing showing properties of NKT-iPS clone 14k.

That is, CD1d-restricted NKT cells are concentrated from splenocytes using MACS beads, after which NKT cells of 99.9% purity are obtained by FACS sorting. The NKT cells can be forced to enter a proliferation cycle by adding IL-2 (10 ng/ml) and IL-12 (10 ng/ml) under stimulation with an anti-CD3 antibody (10 μg/ml) and an anti-CD28 antibody (10 μg/ml). It became evident that by infecting the NKT cells with a retrovirus harboring nucleic acids that encode Oct3/4, Sox2, Klf4, and c-Myc under these conditions, iPS cells could be established more than 10 times more efficiently than in Example 8, whereby the inventors succeeded in establishing NKT-iPS clone 14k (FIG. 31). As shown in FIG. 32, 14k exhibits an ES cell-like morphology, the expression of ES cell markers, and rearrangement of the NKT cell T cell receptor in the T cell receptor region. Also, as examined by the method described in Example 9, differentiation into NKT cell-like cells was seen, which proliferated with glycolipid stimulation in vitro and became cytokine-producing functional cells (FIG. 33).

Example 15

Maturation of iPS-NKT Cell

Figure 34:
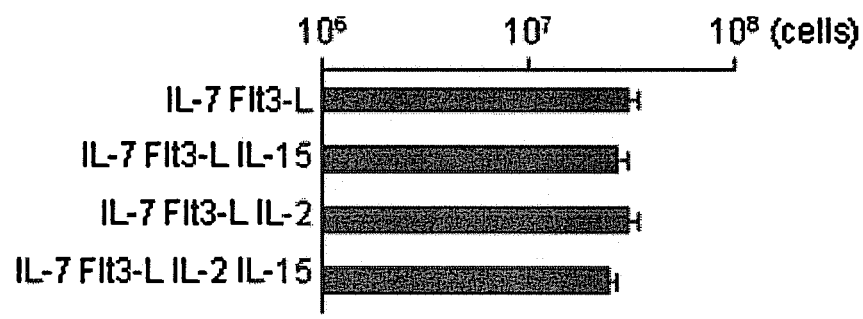
FIG. 34 is a drawing showing the mass expansion of NKT cells from DP-NKT cells using various combinations of cytokines.
Figure 35:
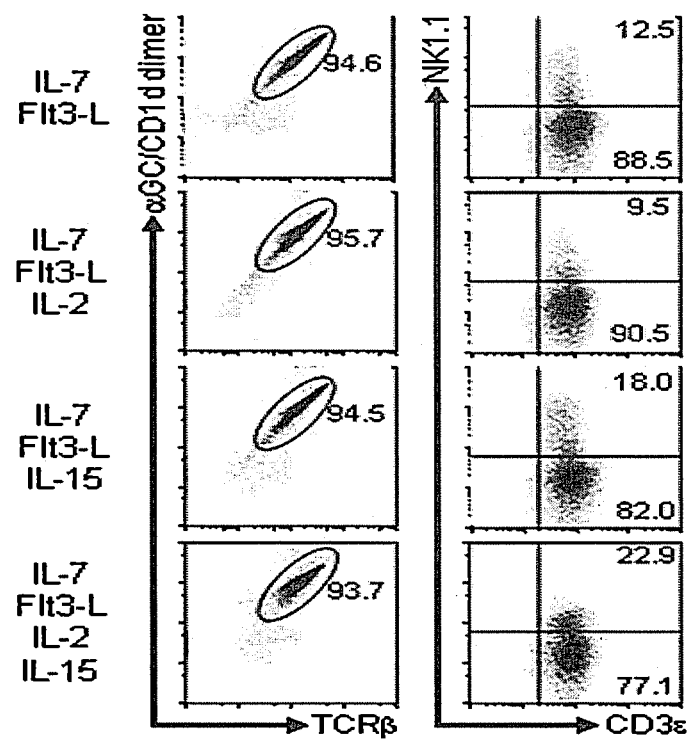
FIG. 35 is a drawing showing expression of invariant TCRα, TCRβ, CD3ε and NK1.1 in cells obtained by co-culturing DP-NKT cells with stromal cells that express a Notch ligand with various combinations of cytokines.
Figure 36:
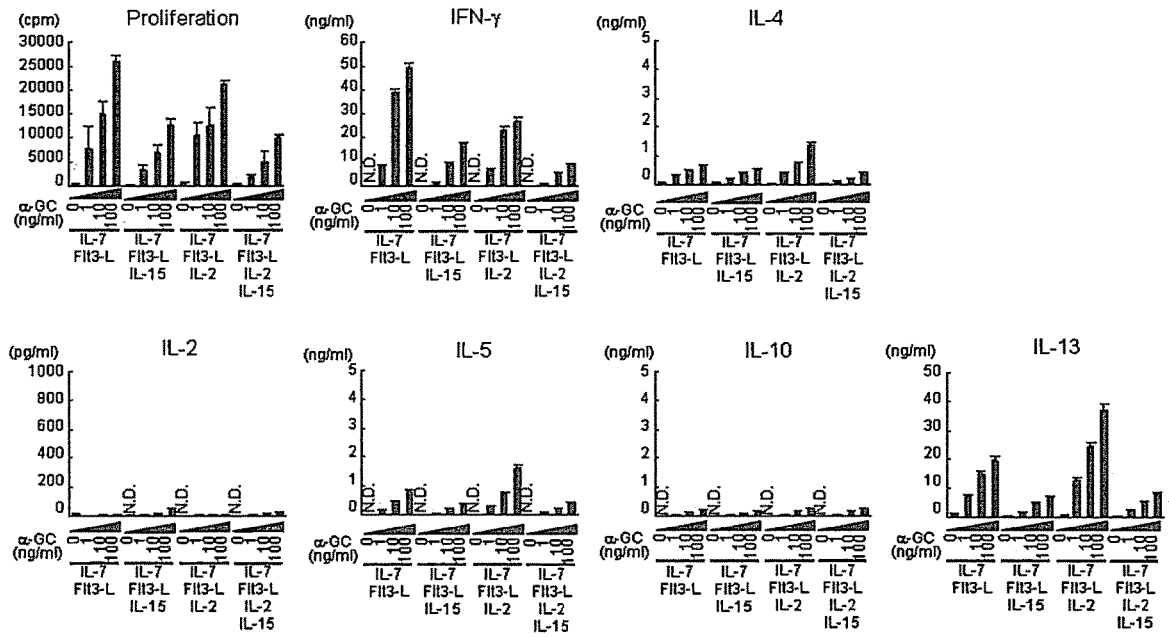
FIG. 36 is a drawing showing the α-GalCer responsiveness of NKT cells differentiation-induced from NKT-iPS cells.

To further expand and mature NKT-iPS cell-derived DP-NKT cells whose induction was confirmed in Example 3(1), in vitro, the cells were cultured using various combinations of cytokines for 5 days. As a result, it was demonstrated that by co-cultivation with OP9/Dll-1 in the presence of the IL-7/Flt3-L, IL-7/IL-15/Flt3-L, IL-7/Flt-3L/IL-2 or IL-2/IL-7/IL-15/Flt3-L cytokine combination, the cells could be further expanded more than 10 times (FIG. 34). Furthermore, it was estimated that the cells cultured under these conditions had undergone further differentiation induction, with the expression of NK1.1 induced therein (FIG. 35). Hence, the NKT cells obtained by induction by co-cultivation with OP9 or OP9/Dll-1 in the presence of the IL-2/IL-15/FL or IL-2/IL-7/IL-15/FL cytokine combination were co-cultured with bone marrow cell-derived dendritic cells (induced with GM-CSF) in the presence of α-GalCer, whereby the proliferation potential and cytokine productivity thereof were checked. As a result, it was confirmed that a proliferation potential was observed when the cells were further cultured with OP9/Dll-1 (FIG. 36), and that a bias to Th1 existed particularly when cultured with IL-7/Flt3-L (FIG. 36).

Reference Example 3

Onset of Acute GVHD Due to Transfer of Allo-T Cell or NKT Cell

Figure 37:
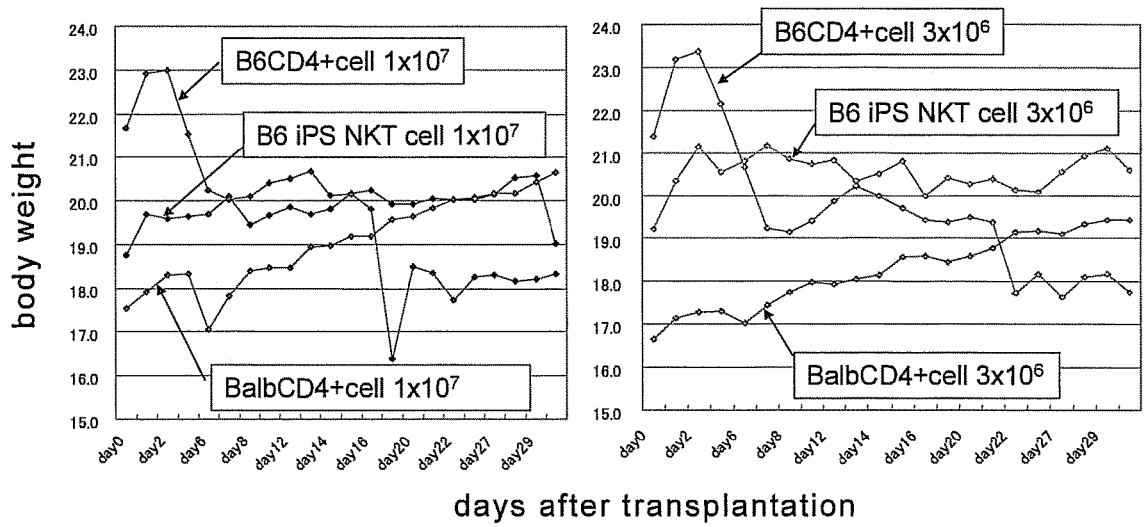
FIG. 37 is a drawing showing that allo-NKT cells induced from iPS cells do not induce GVHD.
Figure 38:
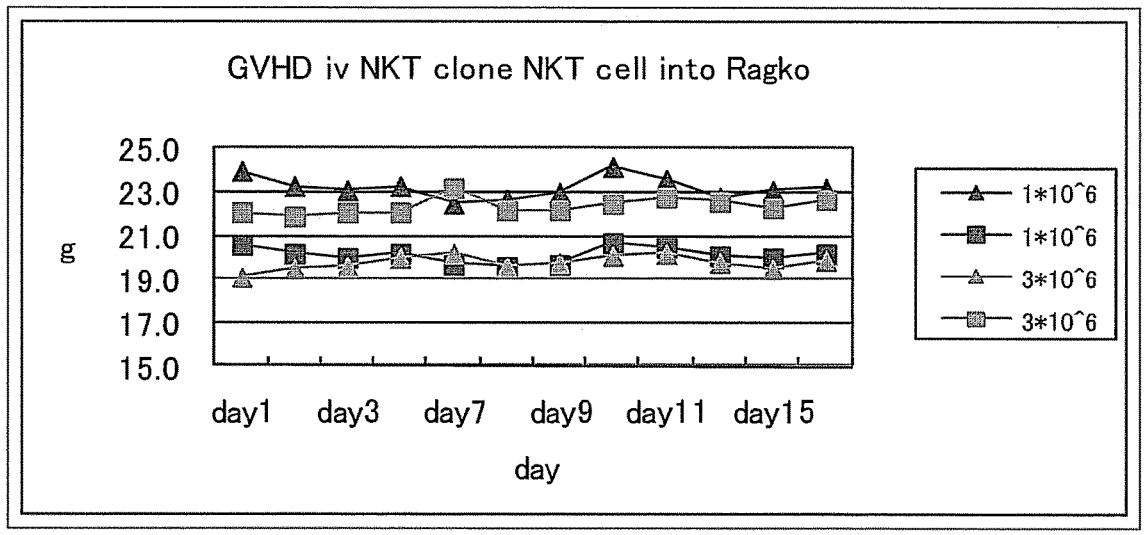
FIG. 38 is a drawing showing that allo-NKT cells of an NKT clone mouse do not induce GVHD.

To confirm an acute GVHD onset effect by the transfer of allo-T cells or NKT cells, wild-type mouse (C57BL/6 background) spleen-derived CD4-positive. helper T cells or NKT clone mouse (C57BL/6 background) spleen-derived NKT cells were transferred into a RAG KO mouse deficient in T cell, B cell and NKT cell (BALB/c background), while dispersing the dose of the cell number. In the case of the CD4-positive helper T cell, transfer of $1 \times 10^7$ to $3 \times 10^6$ cells caused body weight loss with severe diarrhea (FIG. 37), where the onset of acute GVHD was observed. On the other hand, when clone mouse spleen-derived NKT cells were transferred, diarrhea and body weight loss were not found even when the cells in the same number as the CD4-positive helper T cell were transferred (FIG. 38), and therefore, GVHD was considered to not have been induced. Even when NKT cells obtained by cultivating an iPS cell established from C57BL/6 background spleen-derived NKT cells by forcible expression of Oct-3/4, Sox2, Klf4 and c-Myc, in the presence of OP9/Dll-1 cell, IL-7 (1 ng/mL) and Flt3 ligand (10 ng/mL) for 25 days were transferred in the same number as above, diarrhea and body weight loss were not found (FIG. 37), and therefore, GVHD was considered to not have been induced. These results suggest that allo-NKT cells or allo-iPS cell-derived NKT cells does not develop GVHD by transplantation, unlike CD4-positive helper T cells.

Example 16

Adjuvant Effect of Allo-NKT Cell on T Cell

Figure 39:
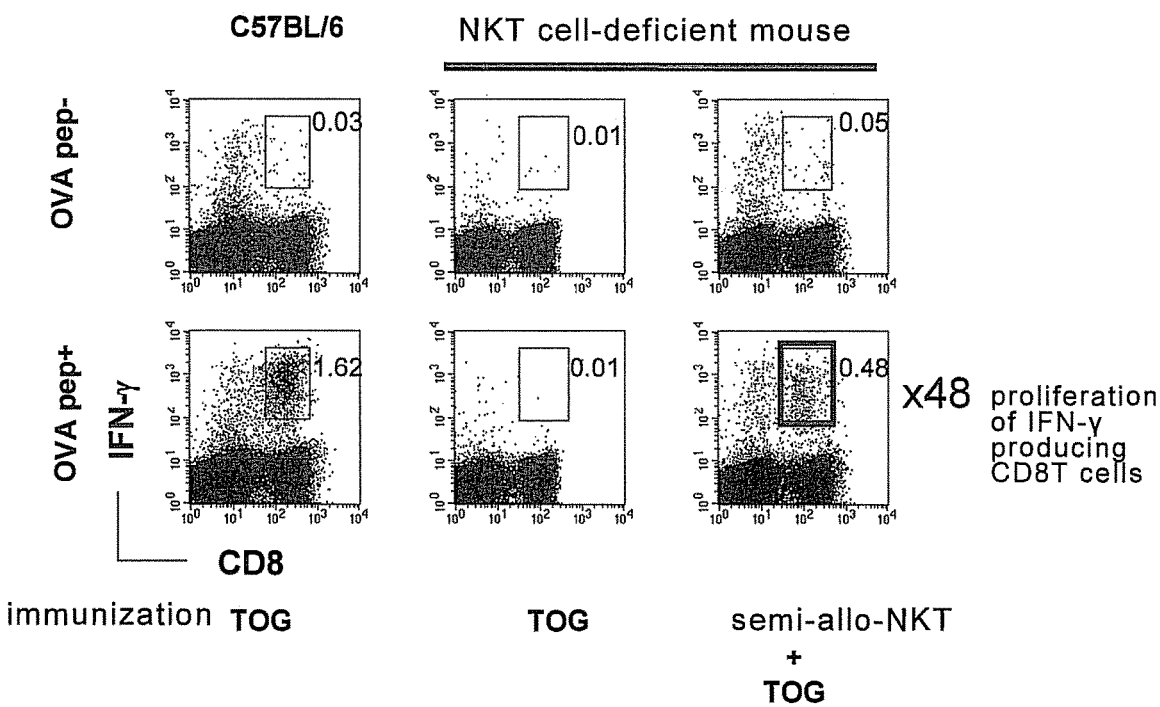
FIG. 39 is a drawing showing an adjuvant effect of semi-allo-NKT cells on CD8 T cells.

NKT cells were transfused into an NKT KO mouse (Ja18-KO mouse), and the adjuvant effect was evaluated in the co-administration system of OVA protein antigen and α-GalCer. (page 3, left figure) OVA and α-GalCer were administered to a wild-type mouse (C57BL/6 background), spleen cells were isolated one week later, re-stimulated with class I-restricted OVA peptide, which is CDBT cell epitope, and analyzed by intracellular staining. As a result, IFN-γ production by antigen-specific CDBT cells was found (FIG. 39, left). However, when OVA and α-GalCer were administered to a Ja18-KO mouse (C57BL/6 background), the adjuvant effect could not be exhibited (FIG. 39, middle). The both results mean that NKT cell shows an adjuvant effect.

On the other hand, when an NKT cells differentiated from ES cells derived from B6/129, semi allo cells, were administered to a Ja18-KO mouse (C57BL/6 background), and OVA and α-GalCer were administered, an immune response of CDBT cell was found (FIG. 39, right). This result means that ES cell-derived NKT cells show an adjuvant effect even though it is allo.

Example 17

Antitumor Effect of Allo NKT Cell

Figure 40:
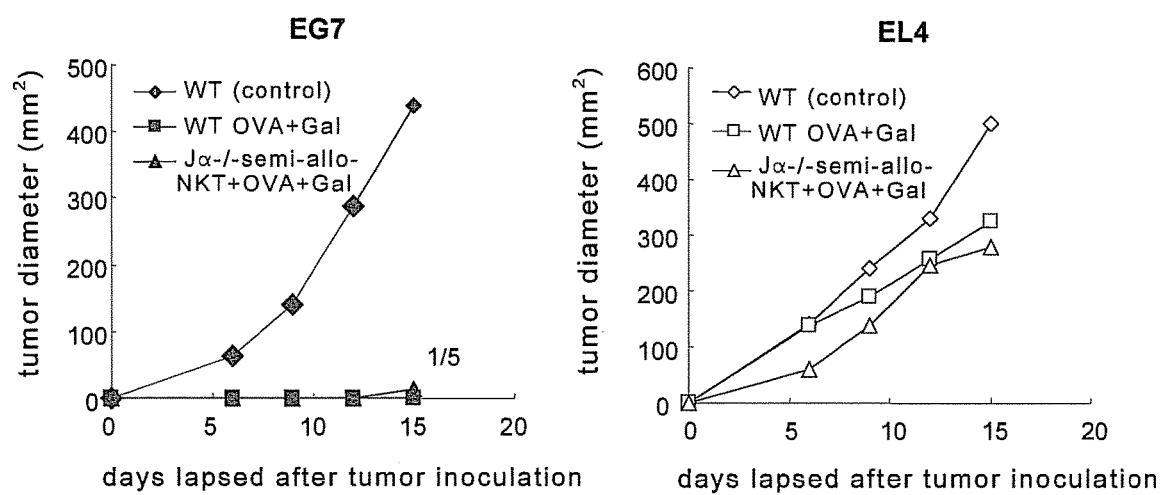
FIG. 40 is a drawing showing an adjuvant effect of semi-allo-NKT cells on an antigen specific antitumor action.

Since it has been clarified above that the allo NKT cell exhibits an adjuvant effect on OVA antigen-specific CD8-positive T cell, the effect of the allo-NKT cell on the removal of the tumor cell was confirmed using OVA as a simulated antigen. EL4 which is a mouse lymphoma cell line and EG7 which is a cell line obtained by forcibly expressing OVA in EL4 were inoculated to a mouse. The following three groups were measured for the tumor diameter after administration of tumor cell: (i) C57BL/6 wild-type mouse, (ii) C57BL/6 wild-type mouse administered with OVA and α-GalCer 1 week before inoculation of the tumor cells, and (iii) Ja18 KO mouse (C57BL/6 background) administered with NKT cells differentiated from ES cells derived from semi-allo cell B6/129, OVA and α-GalCer 1 week before inoculation of the tumor cells. Since similar tumor growth over time was confirmed in the three groups of EL4 inoculation group (FIG. 40, right graph), this experiment system was confirmed to have been working. Under this condition, tumor growth could not be observed in groups (ii) and (iii) in the EG7 transfer group (FIG. 40, left graph). The result shows that an antigen-specific adjuvant effect is induced in an NKT cell-dependent manner (system of (ii)), and an antigen-specific adjuvant effect is induced by transfer even in semi-allo-NKT cell (system of (iii)).

INDUSTRIAL APPLICABILITY

Provision of the NKT cell therapy of the present invention and a human NKT-derived cell or said cell NKT cell bank therefor is extremely useful for an immunocyte treatment which has been performed in a manual industry-like manner heretofore, since it can provide a more rapid, universal technique superior in quality management.

By the achievement in the commercialization of the present banking system, the foundation of cooperative medicine between the development of a human immunocyte iPS fundamental technique that stands practicalization and the development of an application technique with clear target disease treatment, and the bedside is constructed, and the establishment of this pipeline is expected to be utilized as a prototype foundation of an advanced immunotherapy technique utilizing the iPS technique for other disease areas, and afford a large ripple effect on the health-care in not only our country but also all the countries of the world.

This application is based on an U.S. provisional application No. 61/419,064 (filing date: Dec. 2, 2010), the contents of which are incorporated in full herein.

The invention claimed is:

1. A method for inducing an immune response to cancer cells comprising administering (i) an effective amount of NKT cells having Th1 dominant cytokine production capacity and (ii) an effective amount of an NKT cell receptor ligand or dendritic cells pulsed with the NKT cell receptor ligand to an allogeneic subject with cancer,
   wherein the NKT cells have been obtained by differentiating in vitro induced pluripotent stem (iPS) cells having the α-chain region of a T cell antigen receptor gene rearranged to uniform Vα-Jα in an NKT cell receptor-specific manner, and
   wherein the allogeneic subject has at least one different genotype of a locus from that of NKT cells in WIC gene loci,
   thereby inducing an immune response to cancer cells in the subject.

2. The method according to claim 1, wherein the iPS cells are human iPS cells.

3. The method according to claim 1, wherein the iPS cells are derived from an NKT cell.

4. The method according to claim 3, wherein the NKT cell is a human NKT cell.

5. The method according to claim 4, wherein the allogeneic subject has at least one different genotype of a locus from that of the human NKT cell in the HLA gene loci.

6. The method according to claim 5, wherein the HLA gene locus includes HLA-A, HLA-B and HLA-C.

7. The method according to claim 1, wherein the NKT cell receptor ligand is α-galactosylceramide.

8. The method according to claim 1, wherein the NKT cells to be administered produce IFN-γ by stimulation with an NKT cell receptor ligand.

9. The method according to claim 1, wherein the NKT cell is CD3ε+, Sca1+, CD44+, CD69+, CD34−, and Flt3−.

* * * * *

UNITED STATES PATENT AND TRADEMARK OFFICE
CERTIFICATE OF CORRECTION

PATENT NO. : 10,813,950 B2  
APPLICATION NO. : 13/991059  
DATED : October 27, 2020  
INVENTOR(S) : Masaru Taniguchi et al.

Page 1 of 1

It is certified that error appears in the above-identified patent and that said Letters Patent is hereby corrected as shown below:

In the Claims

Claim 1, at Column 49, Line 66, "WIC" should read "MHC"

Signed and Sealed this  
Ninth Day of March, 2021

Drew Hirshfeld  
*Performing the Functions and Duties of the*  
*Under Secretary of Commerce for Intellectual Property and*  
*Director of the United States Patent and Trademark Office*